United States Patent
Goldstein et al.

(10) Patent No.: US 7,501,410 B2
(45) Date of Patent: Mar. 10, 2009

(54) METHODS OF INHIBITING BTK AND SYK PROTEIN KINASES

(75) Inventors: David Michael Goldstein, San Jose, CA (US); Matthias Rueth, Penzberg (DE)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/725,752

(22) Filed: Mar. 20, 2007

(65) Prior Publication Data

US 2007/0219195 A1    Sep. 20, 2007

Related U.S. Application Data

(60) Provisional application No. 60/784,134, filed on Mar. 20, 2006.

(51) Int. Cl.
  *A61K 31/5377* (2006.01)
  *A61K 31/502* (2006.01)
(52) U.S. Cl. .................. 514/232.8; 514/234.5; 514/248
(58) Field of Classification Search .................. None
  See application file for complete search history.

(56) References Cited

U.S. PATENT DOCUMENTS

| | | | |
|---|---|---|---|
| 7,282,588 B2* | 10/2007 | Dhanak et al. | 546/133 |
| 2005/0256102 A1* | 11/2005 | Claiborne et al. | 514/215 |
| 2006/0035908 A1* | 2/2006 | Lew et al. | 514/260.1 |
| 2006/0089359 A1* | 4/2006 | Boyd et al. | 514/248 |

| | | | |
|---|---|---|---|
| 2007/0185111 A1* | 8/2007 | Cee et al. | 514/241 |

FOREIGN PATENT DOCUMENTS

| | | |
|---|---|---|
| WO | WO 03/015785 A1 | 2/2003 |
| WO | WO 03/055491 A1 | 7/2003 |
| WO | WO 2004/072033 A2 | 8/2004 |
| WO | WO 2004/072033 A3 | 8/2004 |
| WO | WO 2006/032518 A1 | 3/2006 |
| WO | WO 2006070195 A1 * | 7/2006 |

* cited by examiner

*Primary Examiner*—Brian-Yong S Kwon
(74) *Attorney, Agent, or Firm*—Brian L. Buckwalter

(57) ABSTRACT

Methods of inhibiting a tyrosine kinase wherein said tyrosine kinase is BTK or SYK comprising administering to a patient in need thereof a therapeutically effective amount of a compound according to formula I are disclosed. The compounds are useful for treating auto-immune and inflammatory diseases.

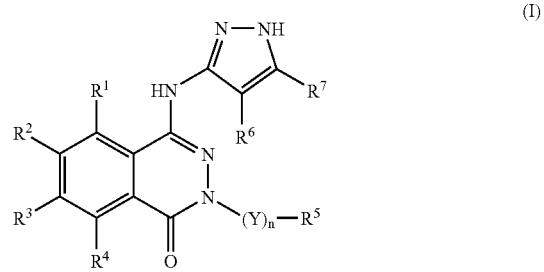

(I)

1 Claim, No Drawings

METHODS OF INHIBITING BTK AND SYK PROTEIN KINASES

CROSS REFERENCE TO PRIOR APPLICATIONS

This application claims the benefit of priority to U.S. Ser. No. 60/784,134 filed Mar. 20, 2006 the contents of which are hereby incorporated in their entirety by reference.

FIELD OF THE INVENTION

The present invention relates to the use of novel phthalazinone derivatives for the treatment of auto-immune and inflammatory diseases caused by aberrant B-cell activation. The novel phthalazinone are useful for the treatment of asthma, rheumatoid arthritis, systemic lupus erythematosus or multiple sclerosis.

BACKGROUND OF THE INVENTION

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. *Annu Rev Med* 2004 55:477). Therefore inhibitors of the protein kinases that play a role in B-cell activation should be useful therapeutics for B-cell mediated disease pathology such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause disregulated B-cell proliferation and formation of pathogenic autoantibodies that lead to multiple autoimmune and/or inflammatory diseases. Two non-receptor tyrosine kinases that are membrane proximal and immediately downstream from BCR are Spleen Tyrosine Kinase (SYK) and Bruton's Tyrosine Kinase (BTK). Lack of either one of these kinases has been shown to block BCR signaling and therefore it is proposed that inhibition of either one or both of these targets would be a useful therapeutic approach to block B-cell mediated disease processes.

BTK is a member of the Tec family of tyrosine kinases, and has been shown to be a critical regulator of early B-cell development and mature B-cell activation and survival (Khan et al. *Immunity* 1995 3:283; Ellmeier et al. J. Exp. Med. 2000 192:1611). Mutation of BTK in humans leads to the condition X-linked agammaglobulinemia (XLA) (reviewed in Rosen et al. *New Eng. J. Med.* 1995 333:431 and Lindvall et al. *Immunol. Rev.* 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for BTK in autoimmune and inflammatory diseases has also been provided by BTK-deficient mouse models. In preclinical murine models of systemic lupus erythematosus (SLE), BTK-deficient mice show marked amelioration of disease progression. In addition, BTK-deficient mice are resistant to collagen-induced arthritis (Jansson and Holmdahl *Clin. Exp. Immunol.* 1993 94:459).

BTK is also expressed by cells other than B-cells that may be involved in disease processes. For example, BTK is expressed by mast cells and BTK-deficient bone marrow derived mast cells demonstrate impaired antigen induced degranulation (Iwaki et al. *J. Biol. Chem.* 2005 280:40261). This shows BTK could be useful to treat pathological mast cell responses such as allergy and asthma. Also monocytes from XLA patients, in which BTK activity is absent, show decreased TNF alpha production following stimulation (Horwood et al. J Exp Med 197:1603, 2003). Therefore, TNF alpha medated inflammation could be inhibited by small molecule inhibitors of BTK. Also, BTK has been reported to play a role in apoptosis (Islam and Smith Immunol Rev 178:49, 2000) and thus BTK inhibitors would be useful for the treatment of certain B-cell lymphomas and leukemias (Feldhahn et al. J Exp Med 201:1837, 2005).

SYK is another non-receptor tyrosine kinase that is essential for B-cell activation through BCR signaling. SYK become activated upon binding to phosphoryated BCR and thus initiates the early signling events following BCR activation. Mice deficient in SYK exhibit an early block in B-cell development (Cheng et al. Nature 378:303, 1995; Turner et al. Nature 378:298, 1995). Therefore inhibition of SYK enzymatic activity in cells is proposed as a treatment for autoimmune disease through its effects on autoantibody production.

In addition to the role of SYK in BCR signaling and B-cell activation, it also plays a key role in FcεRI mediated mast cell degranulation and eosinophil activation. Thus, SYK is implicated in allergic disorders including asthma (reviewed in Wong et al. Expert Opin Investig Drugs 13:743, 2004). SYK binds to the phosphorylated gamma chain of FcεRI via its SH2 domains and is essential for downstream signaling (Taylor et al. Mol. Cell. Biol. 15:4149, 1995). SYK deficient mast cells demonstrate defective degranulation, arachidonic acid and cytokine secretion (Costello et al. Oncogene 13:2595, 1996). This also has been shown for pharmacologic agents that inhibit SYK activity in mast cells (Yamamoto et al. J Pharmacol Exp Ther 306:1174, 2003). Treatment with SYK antisense oligonucleotides inhibits antigen-induced infiltration of eosinophils and neutrophils in an animal model of asthma (Stenton et al. J Immunol 169:1028, 2002). SYK deficient eosinophils also show impaired activation in response to FcεR stimulation (Lach-Trifilieffe et al. Blood 96:2506, 2000). Therefore, small molecule inhibitors of SYK will be useful for treatment of allergy-induced inflammatory diseases including asthma.

SYK kinase inhibitors have be shown to inhbit mast cell degranulation in cell based assays. (Lai et al., *Bioorg. Med. Chem. Lett.* 2003 13:3111-3114; Moriya et al. *Proc. Natl. Acad. Sci. USA* 1997 94:12539-12544; Yamamoto et al. *J. Pharmacol. Exp Ther.* 2003 306(3):1174-1181. A SYK inhibitor also was shown to inhibit antigen-induced passive cutaneous anaphylaxsis, bronchoconstriction and bronchial edema in rats (Yamamoto sypra).

In WO2006/032518, published Mar. 30, 2006, Boyd et al. teach some examples of the phthalazinone compounds disclosed herein as inhibitors of Aurora kinase which are useful for treating cancer and particularly colorectal, breast, lung, prostate, pancreatic, gastric, bladder, cranial, neuroblastoma, cervical, kidney or renal cancer and melanoma.

SUMMARY OF THE INVENTION

The present invention relates to methods of treating a disease mediated by a tyrosine kinase wherein said tyrosine kinase is BTK or SYK comprising administering to a patient in need thereof a therapeutically effective amount of a compound according to formula I

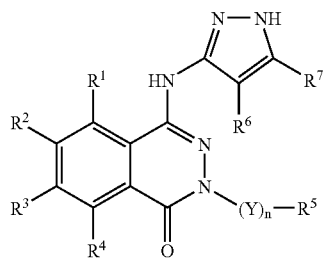

wherein
$R^1$, $R^2$ and $R^4$ independently represent $R^8$—X—, $C_{3-7}$cycloalkyl-$T^1$-, heterocyclyl-$T^2$-, hydrogen, halogen, nitro, cyano, —OH, —$NH_2$, —NH—C(O)H, —C(O)OH, —C(O)$NH_2$, —S(O)$_2NH_2$, —NHC(O)$NH_2$, —C(O)NH—O—$C_{1-6}$alkyl, —C(O)N($C_{1-6}$alkyl)-O—$C_{1-6}$alkyl, —NHC(O)NH—O—$C_{1-6}$alkyl, —NHC(O)N($C_{1-6}$alkyl)-O—$C_{1-6}$alkyl, —S(O)$_2$NH—O—$C_{1-6}$alkyl, —S(O)$_2$N($C_{1-6}$alkyl)-O—$C_{1-6}$alkyl, or $C_{1-6}$alkyl optionally substituted one or three times by halogen, hydroxy or alkoxy;
$R^3$ is $R^8$—X—, $R^9$—$X^1$—, $R^8$—$X^1(CH_2)_m$—, $R^9$—$X^1(CH_2)_m$—, $C_{3-7}$cycloalkyl-$T^1$-, heterocyclyl-$T^2$-, hydrogen, halogen, nitro, cyano, —OH, —$NH_2$, —NH—C(O)H, —C(O)OH, —C(O)$NH_2$, —S(O)$_2NH_2$, —NHC(O)$NH_2$, —C(O)NH—O—$C_{1-6}$alkyl, —C(O)N($C_{1-6}$alkyl)-O—$C_{1-6}$alkyl, —NHC(O)NH—O—$C_{1-6}$alkyl, —NHC(O)N($C_{1-6}$alkyl)-O—$C_{1-6}$alkyl, —S(O)$_2$NH—O—$C_{1-6}$alkyl, —S(O)$_2$N($C_{1-6}$alkyl)-O—$C_{1-6}$alkyl, or $C_{1-6}$alkyl optionally substituted one or three times by halogen, hydroxy or alkoxy;
$R^8$ is $C_{3-7}$cycloalkyl-$T^1$-, heterocyclyl-$T^2$-, aryl-$T^3$-, heteroaryl-$T^4$-, or $C_{1-6}$alkyl optionally substituted one to five times by halogen;
$R^9$ is $C_{1-6}$alkyl wherein said alkyl is substituted one to three times by hydroxy, alkoxy, amino, $C_{1-6}$alkylamino, $C_{1-6}$dialkylamino, $C_{1-6}$alkylsulfanyl, $C_{1-6}$alkylsulfinyl, $C_{1-6}$alkylsulfonyl, $C_{1-6}$alkylsulfamoyl, $C_{1-6}$dialkylsulfamoyl, $C_{1-6}$alkylsulfonylamino or heterocyclylsulfonyl;
X is —C(O)NH—, —C(O)N(alkyl)-, —N(alkyl)C(O)—, —NHC(O)—, —NHC(O)NH—, —NHC(O)N(alkyl)-, —OC(O)N(alkyl)-, —NHS(O)$_2$—, —S(O)$_2$NH—, —S(O)$_2$N(alkyl)-, —S(O)$_2$—, —S(O)—, —C(O)O—, —OC(O)—, —C(O)—, —NH—, —N(alkyl)-, —O— or —S—;
$X^1$ is —S(O)$_2$—, —S(O)—, —OC(O)—, —C(O)—, —NH—, —N(alkyl)-, —O— or —S—;
$T^1$, $T^2$, $T^3$ and $T^4$ independently represent a single bond or alkylene optionally substituted one or two times by hydroxy;
$R^5$ is hydrogen, $C_{1-6}$alkyl being optionally substituted one or several times by halogen or alkoxy, heteroaryl, or phenyl, which is optionally substituted one or two times by halogen, —$NO_2$, —OH, —C(O)OH, —C(O)NH-aryl, —C(O)$NH_2$, —C(O)NH—$C_{1-6}$alkyl, —C(O)N($C_{1-6}$alkyl)$_2$, —C(O)-heterocyclyl, —$NH_2$, —NHC(O)-aryl, —NHC(O)—$C_{3-7}$cycloalkyl, —NHC(O)—$C_{1-6}$alkyl, —N($C_{1-6}$alkyl)C(O)—$C_{1-6}$alkyl, —NHC(O)O—$C_{1-6}$alkyl, —N($C_{1-6}$alkyl)C(O)O—$C_{1-6}$alkyl, —NHC(O)—$C_{1-6}$alkoxyalkyl, —NH—S(O)$_2$-aryl, —NH—S(O)$_2$—$C_{1-6}$alkyl, —C(O)NH—S(O)$_2$-aryl, —C(O)NH—S(O)$_2$—$C_{1-6}$alkyl, —S(O)$_2$-alkyl, —NH-aryl, —O-aryl, —S(O)-aryl, aryl, heterocyclyl, $C_{3-7}$cycloalkyl, $C_{1-6}$alkyl, $C_{1-6}$alkoxy or $C_{1-6}$alkylsulfanyl, said alkyl, alkoxy and alkylsulfanyl groups being optionally substituted one or three times by halogen; naphthyl optionally independently substituted with one to three halogens, phenyl independently substituted with three halogens; 1,3-dihydro-isobenzofuranyl, benzo[1,3]dioxol-5-yl, $C_{3-7}$cycloalkyl or $C_{1-6}$alkenyl;
Y is alkylene, alkylene-C(O)— or alkylene-CH(OH)—;
m is 1 to 5;
n is 0 or 1;
$R^6$ is hydrogen, $C_{1-6}$alkyl, cyano or halogen; and
$R^7$ is hydrogen, $C_{1-6}$alkyl or $C_{3-7}$cycloalkyl;
or a pharmaceutically acceptable salt thereof.

DETAILED DESCRIPTION OF THE INVENTION

Tyrosine kinase inhibitors of formula I are useful in the treatment of allergy-induced inflammatory disease. Among the diseases that can be alleviated by administration of a therapeutically effective amount of a compound of formula I are allergy-induced inflammatory diseases including asthma, systemic lupus erythematosis and multiple sclerosis. Compounds of the present invention also are beneficial in the treatment of rheumatoid arthritis The compounds according to this invention show activity as protein kinase inhibitors. Many diseases are associated with abnormal cellular responses triggered by protein kinase mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

The compounds according to this invention in particular show activity as BTK and SYK inhibitors, and may therefore be useful for the treatment of diseases mediated by these kinases. Inhibition of BTK and/or SYK blocks B-cell receptor (BCR) signaling and resulting B-cell maturation and activation. This indicates BTK and SYK inhibitors will be useful in the treatment of autoimmune diseases such as rheumatoid arthritis, multiple sclerosis and systemic lupus erythematosus. In addition, inhibitors of SYK in particular have utility as treatments of allergic inflammation including asthma. Both kinases have been linked to regulation of apoptosis and may be useful treatments for lymphomas or leukemias. In particular, BTK has recently been implicated in certain Philadelphia positive cases of acute myelogenous leukemia (AML) and thus may be an effective treatment for certain subsets of AML patients.

The present invention includes methods of treating inflammatory and auto-immune diseases with compounds of formula I and all tautomers, pharmaceutically acceptable salts, enantiomeric forms, diastereoisomers and racemates thereof, their use as BTK and SYK inhibitors. For example, the pyrazole ring of formula I can exist in two tautomeric forms as shown here below and the present invention contemplates treating inflammatory and auto-immune with all tautomers:

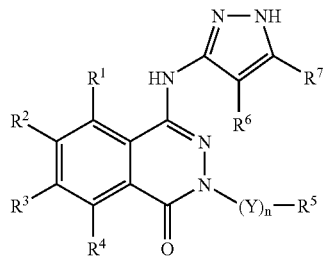 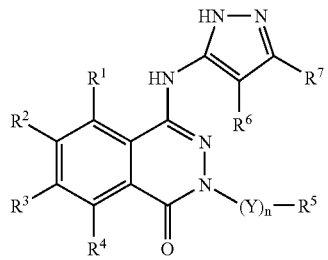

The phrase "as defined herein above" refers to the broadest definition for each group as provided in the broadest claim. In all other embodiments provided below, substituents which can be present in each embodiment and which are not explicitly defined retain the broadest definition provided in the Summary of the Invention.

The phrase "a" or "an" entity as used herein refers to one or more of that entity; e.g., a compound refers to one or more compounds or at least one compound. As such, the terms "a" (or "an"), "one or more", and "at least one" can be used interchangeably herein.

In one embodiment of the present invention there is provided a method for treating a disease mediated by the tyrosine kinases BTK and/or SYK comprising administering to a patient in need thereof a therapeutically effective amount of a compound according to formula I wherein $R^1$, $R^2$, $R^3$, $R^4$, $R^5$, $R^6$, $R^7$, $R^8$, $R^9$, $T^1$, $T^2$, $T^3$, $T^4$, X, $X^1$, Y, m and n are as defined herein above.

In another embodiment of the present invention there is provided a method for treating a disease mediated by the tyrosine kinases BTK and/or SYK comprising administering to a patient in need thereof a therapeutically effective amount of a compound according to formula I wherein $R^1$, $R^2$, $R^4$ and $R^6$ are hydrogen; $R^3$ is heterocyclyl-$T^2$, $R^8$—X—, $R^9$—$X^1$—, H(O)CNH— or $C_{1-6}$alkyl optionally substituted by hydroxyl; $R^8$ is heterocyclyl-$T^2$; heterocyclyl is piperidine, piperazine, N-methylpiperazine or morpholine; $T^2$ is a single bond; X is —O—, —N($C_{1-6}$alkyl)-, —C(O)NH— or —C(O)N($C_{1-6}$alkyl)-; either n is 0 and $R^5$ is $C_{1-6}$alkyl, or n is 1, Y is $C_{1-6}$alkylene and $R^5$ is optionally substituted phenyl; $R^7$ is $C_{1-3}$alkyl.

In another embodiment of the present invention there is provided a method for treating a disease mediated by BTK comprising administering to a patient in need thereof a therapeutically effective amount of a compound according to formula I wherein $R^1$, $R^2$, $R^3$, $R^4$, $R^5$, $R^6$, $R^7$, $R^8$, $R^9$, $T^1$, $T^2$, $T^3$, $T^4$, X, $X^1$, Y, m and n are as defined herein above.

In another embodiment of the present invention there is provided a method for treating a disease mediated by SYK comprising administering to a patient in need thereof a therapeutically effective amount of a compound according to formula I wherein $R^1$, $R^2$, $R^3$, $R^4$, $R^5$, $R^6$, $R^7$, $R^8$, $R^9$, $T^1$, $T^2$, $T^3$, $T^4$, X, $X^1$, Y, m and n are as defined herein above.

In yet another embodiment of the present invention there is provided a method for treating an allergy-induced inflammatory disease comprising administering to a patient in need thereof a therapeutically effective amount of a compound according to formula I wherein $R^1$, $R^2$, $R^3$, $R^4$, $R^5$, $R^6$, $R^7$, $R^8$, $R^9$, $T^1$, $T^2$, $T^3$, $T^4$, X, $X^1$, Y, m and n are as defined herein above.

In yet another embodiment of the present invention there is provided a method for treating asthma comprising administering to a patient in need thereof a therapeutically effective amount of a compound according to formula I wherein $R^1$, $R^2$, $R^3$, $R^4$, $R^5$, $R^6$, $R^7$, $R^8$, $R^9$, $T^1$, $T^2$, $T^3$, $T^4$, X, $X^1$, Y, m and n are as defined herein above.

In yet another embodiment of the present invention there is provided a method for treating systemic lupus erythematosis or multiple sclerosis comprising administering to a patient in need thereof a therapeutically effective amount of a compound according to formula I wherein $R^1$, $R^2$, $R^3$, $R^4$, $R^5$, $R^6$, $R^7$, $R^8$, $R^9$, $T^1$, $T^2$, $T^3$, $T^4$, X, $X^1$, Y, m and n are as defined herein above.

In yet another embodiment of the present invention there is provided a method for treating rheumatoid arthritis comprising administering to a patient in need thereof a therapeutically effective amount of a compound according to formula I wherein $R^1$, $R^2$, $R^3$, $R^4$, $R^5$, $R^6$, $R^7$, $R^8$, $R^9$, $T^1$, $T^2$, $T^3$, $T^4$, X, $X^1$, Y, m and n are as defined herein above.

As used herein, the term "alkyl" means a saturated, straight-chain or branched-chain hydrocarbon containing from 1 to 6, preferably from 1 to 4, more preferred 1 or 2, carbon atoms, such as methyl, ethyl, n-propyl, isopropyl, n-butyl, 2-butyl, t-butyl.

As used herein, the term "alkoxy" means an alkyl group as defined above which is connected via an oxygen atom.

As used herein, the term "alkylsulfanyl" means an alkyl group as defined above which is connected via a sulfur atom.

If said alkyl, alkoxy or alkylsulfanyl group is substituted one or several times by halogen, it is substituted one to five, preferably one to three times by chlorine or fluorine, preferably by fluorine. Examples are difluoromethyl, trifluoromethyl, 2,2,2-trifluoroethyl, perfluoro-ethyl, 2,2,2-trichloroethyl, 2-chloro-ethyl, 3-chloro-propyl and the like, preferably difluoromethyl, trifluoromethyl, 2,2,2-trifluoroethyl or perfluoroethyl. The term "haloalkyl" as used herein refers to an alkyl group as defined herein substituted by 1 to 5 halogens.

If said alkyl is substituted one or several times by hydroxy or alkoxy it is substituted one to three, preferably one to two times by hydroxy or alkoxy. Examples are e.g. hydroxy-methyl, 2-hydroxy-butyl, 2-hydroxy-ethyl, 1-hydroxy-ethyl, 2-hydroxy-propyl, 3-hydroxy-butyl, 2,3-dihydroxy-propyl, 2,3-dihydroxy-butyl, 1,2,3-trihydroxy-propyl, 2-hydroxy-pentyl, methoxy-methyl, ethoxy-methyl, 2-methoxy-ethyl, 2-ethoxy-ethyl, 4-methoxy-butyl, 2-methoxy-butyl, 2-ethoxy-propyl, 3-propoxy-butyl, 2,3-dimethoxy-propyl, 2-ethoxy-3-methoxy-propyl, 2,3-diethoxy-butyl, 1,2,3-trimethoxy-propyl, 2-methoxy-pentyl and the like. The term "hydroxyalkyl" as used herein refers to an alkyl group as herein defined substituted with 1 to 3 hydroxy groups.

As used herein, the term "alkylene" means a saturated, straight-chain or branched-chain, preferably straight-chain hydrocarbon containing from 1 to 5, preferably from 1 to 3, carbon atoms, such as methylene, ethylene, trimethylene (1,3-propylene); tetramethylene (butylene), pentamethylene, methyl-methylene, methyl-ethylene (1,2-propylene), ethyl-ethylene, propyl-ethylene, 1-methyl-trimethylene, 2-methyl-trimethylene, 1-ethyl-trimethylene, 2-ethyl-trimethylene.

Preferably Y represents methylene or ethylene and more preferred methylene.

As used herein, the term "alkenyl" means an unsaturated, straight-chain or branched-chain, preferably straight-chain hydrocarbon containing from 2 to 6, preferably from 2 to 4, carbon atoms. Examples of such "alkenyl" are vinyl (ethenyl), allyl, isopropenyl, 2-butenyl, 3-butenylene, 3-methyl-2-butenyl, 2-pentenyl, 3-pentenyl, 4-pentenyl, 4-methyl-3-pentenyl, 2-hexenyl, 3-hexenyl, 4-hexenyl and 5-hexenylene, preferably allyl.

The term "halogen" as used herein means fluorine, chlorine, bromine and iodine, preferably fluorine, chlorine or bromine and more preferred fluorine and chlorine.

The term "aryl" as used herein means a phenyl or naphthyl, e.g. 1-naphthyl, 2-naphthyl or 3-naphthyl and preferably a phenyl group. Such aryl group can be optionally substituted one to three, preferably one or two times by a) alkyl, b) halogenated alkyl, c) halogen, preferably by chlorine or fluorine, d) cyano, e) alkoxy, f) halogenated alkoxy, g) —C(O)-alkyl, preferably acetyl, h) alkylsulfonyl, i) hydroxy, j) amino or k) nitro. Preferably the aryl is optionally substituted by a) alkyl, b) halogenated alkyl, c) halogen, d) cyano, e) alkoxy, f) halogenated alkoxy or i) hydroxy. More preferred the aryl is optionally substituted by a) alkyl, b) halogenated alkyl, c) halogen, d) cyano, e) alkoxy, f) halogenated alkoxy or i) hydroxy. In one embodiment of the invention the aryl group as defined in $R^8$ is optionally substituted one to three times as described above while the aryl groups in $R^5$ are unsubstituted. Even more preferably all aryl groups are unsubstituted. Examples of substituted aryl groups are e.g. 4-methyl-phenyl, 3-methyl-phenyl, 2-methyl-phenyl, 4-chloro-phenyl, 3-chloro-phenyl, 2-chloro-phenyl, 4-fluoro-phenyl, 2-fluoro-phenyl, 4-trifluoromethyl-phenyl, 4-trifluoromethyl-2-fluoro-phenyl, 3-trifluoromethyl-phenyl, 4-trifluoromethoxy-phenyl, 3- trifluoromethoxy-phenyl, 4-cyano-phenyl, 3-cyano-phenyl, 4-amino-phenyl, 3-hydroxy-phenyl, 4-acetyl-phenyl, 4-acetyl-2-methyl-phenyl and the like.

The term "heteroaryl" means a mono- or bicyclic aromatic ring with 5 to 10 ring atoms, which contains up to 3, preferably 1 or 2 heteroatoms selected independently from N, O or S and the remaining ring atoms being carbon atoms. Such heteroaryl group can be optionally substituted one to three, preferably one or two times by a) alkyl, which is defined as above, preferably by methyl, b) halogenated alkyl, c) halogen, preferably by chlorine or fluorine, d) cyano, e) alkoxy, f) halogenated alkoxy. Preferably the heteroaryl is optionally substituted by a) alkyl, b) halogenated alkyl, c) halogen, d) cyano, e) alkoxy, f) halogenated alkoxy or i) hydroxy. More preferred the heteroaryl is optionally substituted by a) alkyl, b) halogenated alkyl, c) halogen, d) cyano, e) alkoxy, f) halogenated alkoxy or i) hydroxy. Even more preferred the heteroaryl is optionally substituted by alkyl. Examples of such heteroaryl groups are thiophenyl, methylthiophenyl, pyrazolyl, dimethylisoxazolyl, pyridyl, benzothiophenyl, indolyl, furyl, pyrrolyl, imidazolyl, pyrimidyl, pyrazinyl, pyridazinyl, triazinyl, oxazolyl, isoxazolyl, thiazolyl, methylthiazolyl, isothiazolyl, thiadiazolyl, oxadiazolyl, triazolyl, quinolyl, isoquinolyl, benzofuranyl and the like, preferably thiazolyl, methylthiazolyl, pyridyl, methylpyridyl, trifluoromethyl-pyridyl, pyrimidyl, triazolyl, methyltriazolyl or thiadiazolyl, more preferred pyridyl or methylthiazolyl.

The term "cycloalkyl" means a monocyclic saturated hydrocarbon ring with 3 to 7, preferably 3 to 5, ring atoms. Such monocyclic saturated hydrocarbon ring can be optionally substituted one to three, preferably one or two times by alkyl, preferably by methyl. Preferably the cycloalkyl is unsubstituted. Examples of such saturated carbocyclic groups are cyclopropyl, 1-methyl-cycloprop-1-yl, cyclobutyl, cyclopentyl, cyclohexyl, 3,3-dimethyl-cyclohex-1-yl, and cycloheptyl, preferably cyclopropyl, preferably cyclopropyl, cyclobutyl, and cycloheptyl, more preferred cyclopropyl.

The term "heterocyclyl" means a saturated, monocyclic ring with 5 to 6 ring atoms which contains up to 3, preferably 1 or 2 heteroatoms selected independently from N, O or S and the remaining ring atoms being carbon atoms. Such saturated heterocyclic group can be optionally substituted one to three, preferably one or two times by a) alkyl, which is defined as above, preferably by methyl, b) —C(O)-alkyl, preferably acetyl, c) oxo or d) —S(O)2-alkyl. Preferably the heterocyclic group can be optionally substituted by alkyl. Examples of such saturated heterocyclic groups are pyrrolidinyl, morpholinyl, thiomorpholinyl, 1,1-dioxo-1$\lambda^6$-thiomorpholin-4-yl (or 1,1-dioxido-thiomorpholin-4-yl), piperazinyl, N-methyl-piperazinyl, N-acetyl-piperazinyl, 3-oxo-piperazin-1-yl, 2-oxo-piperazin-1-yl, piperidyl, oxazolidinyl, thiazolidinyl and the like, preferably morpholinyl, piperazinyl, N-methyl-piperazinyl or N-acetyl-piperazinyl, and especially morpholinyl, N-methyl-piperazinyl or piperidyl.

Commonly used abbreviations herein include: N,N'-dicyclohexylcarbodiimide (DCC), 1,2-dichloroethane (DCE), dichloromethane (DCM), di-iso-propylethylamine (DIPEA), N,N-dimethylformamide (DMF), dimethyl sulfoxide (DMSO), 1-(3-dimethylaminopropyl)-3-ethylcarbodiimide hydrochloride (EDCI), ethyl (Et), ethyl acetate (EtOAc), ethanol (EtOH), acetic acid (HOAc), iso-propanol (IPA), methanol (MeOH), melting point (mp), acetonitrile (MeCN), mass spectrum (ms or MS), N-methylpyrrolidone (NMP), positive electrospray ionization mode (ESI+), room temperature (RT), triethylamine (TEA or Et$_3$N), trifluoroacetic acid (TFA), tetrahydrofuran (THF). Conventional nomenclature including the prefixes normal (n), iso (i-), secondary (sec-), tertiary (tert-) and neo have their customary meaning when used with an alkyl moiety. (Rigaudy and Klesney, *Nomenclature in Organic Chemistry*, IUPAC 1979 Pergamon Press, Oxford.).

The term "pharmaceutically acceptable salt" is as used below.

The term "therapeutically effective" or "therapeutically effective amount" as used herein means an amount of at least one compound of Formula 1, or a pharmaceutically acceptable salt thereof that significantly inhibits proliferation and/or prevents differentiation of B-cells.

As used herein, in relation to nuclear magnetic resonance (NMR) the term "D$_6$-DMSO" refers to deuterated dimethylsulfoxide; the term "CDCl$_3$" refers to deuterated chloroform; the term "C$_6$D$_6$" refers to deuterated benzene; and the term "CD$_3$OD" refers to deuterated MeOH.

The amino pyrazole derivatives of the general formula I, or a pharmaceutically acceptable salt thereof, may be prepared by any process known to be applicable for the preparation of chemically-related compounds by one skilled in the art. Such processes, when used to prepare the amino pyrazole deriva tives of formula I, or a pharmaceutically-acceptable salt thereof, are provided as a further feature of the invention and are illustrated by the following schemes 1, 2, 3, 4, 5 and 6 in which, unless otherwise stated, $R^1$, $R^2$, $R^3$, $R^4$, $R^5$, $R^6$, $R^7$, $R^8$, $R^9$, $T^1$, $T^2$, $T^3$, $T^4$, X, $X^1$, Y, n, have the significance given herein before. Necessary starting materials may be obtained by standard procedures of organic chemistry. The preparation of such starting materials is described within the accompanying non-limiting examples. Alternatively necessary starting materials are obtainable by analogous procedures to those illustrated which are within the ordinary skill of an organic chemist.

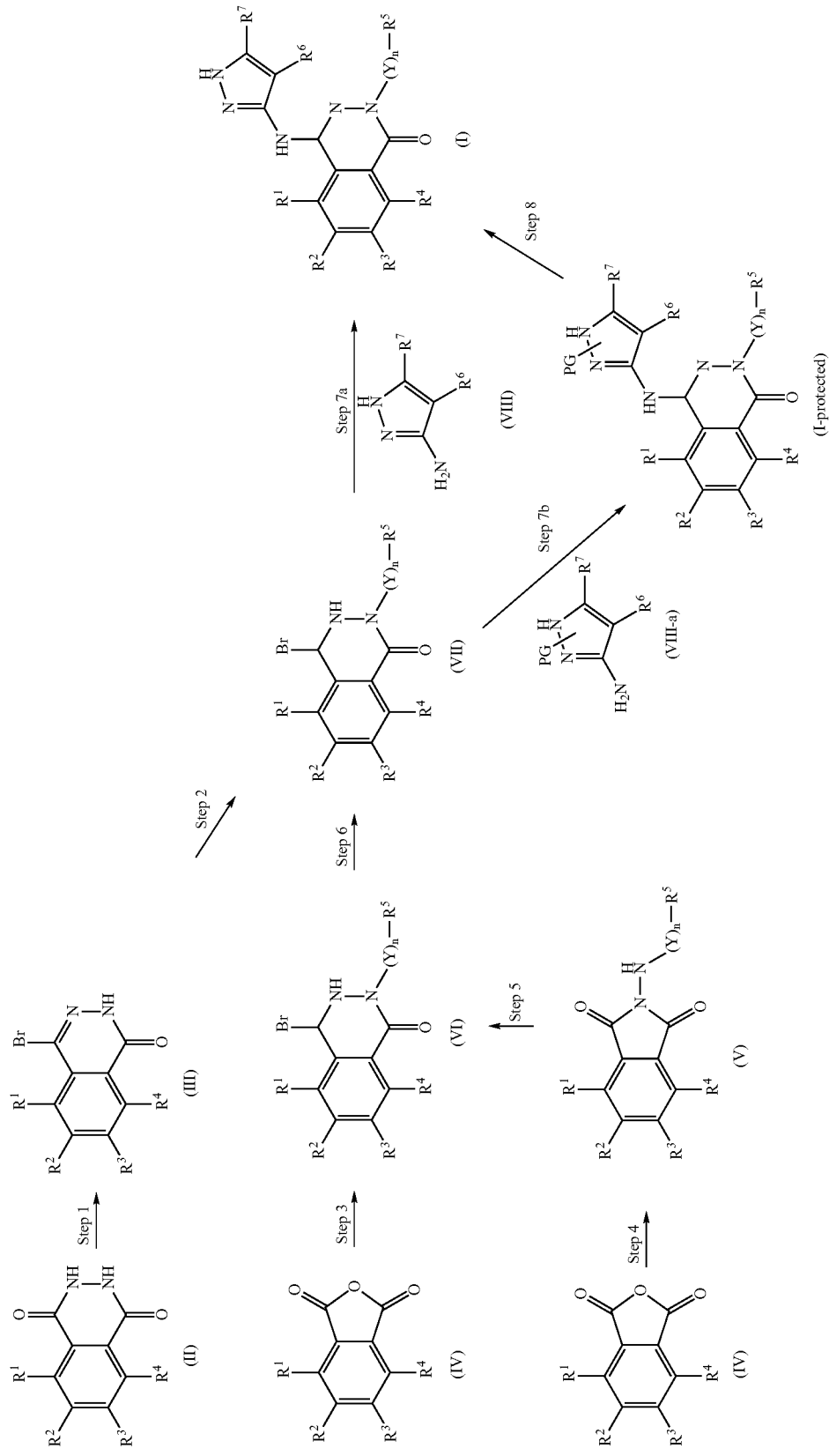
Scheme 1

A method for the synthesis of the compounds of formula I starts from the corresponding phthalazine diones of formula II. Step 1 of the reaction sequence (scheme 1) is a two step process in which a dibromination is followed by a monohydrolysis, yielding the 4-bromo-phthalazinone derivatives of formula III. The first step (dibromination) is typically carried out without solvent, or in solvents like dichloromethane (DCM), dichloroethane (DCE), anisole, and mixtures thereof, at temperatures between 30° C. and 150° C. Typically used brominating reagents are phosphorus oxybromide, phosphorus pentabromide and phosphorus tribromide. The second step (monohydrolysis of the dibromide) is typically carried out in aqueous or anhydrous conditions in solvents such as water, aqueous lithium hydroxide, aqueous sodium hydroxide, aqueous potassium hydroxide, aqueous sodium hydrogen carbonate, aqueous sodium carbonate, aqueous potassium hydrogen carbonate, aqueous potassium carbonate, aqueous methanol (MeOH), glacial acetic acid (HOAc) at temperatures between 20° C. and 110° C.

In step 2, scheme 1 the obtained compounds of formula III are converted into their corresponding tertiary amides of formula VII, using methods well known to someone skilled in the art, e.g. alkylation under basic conditions. The reaction is typically carried out in aprotic solvents such as tetrahydrofuran (THF), N,N-dimethylformamide (DMF), dimethyl sulfoxide (DMSO), N-methylpyrrolidinone (NMP) and mixtures thereof at temperatures between −78° C. and 100° C. Typically used bases are sodium hydride, potassium hydride, sodium methoxide, potassium tert-butoxide, lithium hexamethyldisilazide, sodium hexamethyldisilazide, potassium hexamethyldisilazide in conjunction with alkylating agents such as alkyl halides, alkyl mesylates and alkyl triflates. Instead of an alkylating agent, also alcohols can be applied in step 2 under the conditions of the Mitsunobu reaction, e.g. in the presence of diethyl azodicarboxylate and triphenylphosphine, typically in solvents like THF or DCM at room temperature (RT).

In step 3, scheme 1 the phthalic anhydride derivatives of formula IV are converted with the appropriate hydrazine derivatives into their corresponding phthalazinones of formula VI, using methods well known to someone skilled in the art. The reaction is typically carried out in aprotic solvents such as THF, DMF, NMP or protic solvents such as HOAc, ethanol (EtOH), MeOH and isopropanol (IPA) and mixtures thereof at temperatures between 0° C. and 120° C. Typically used hydrazine derivatives are aliphatic hydrazines or aromatic hydrazines, and salts thereof such as phenyl hydrazine hydrochloride, methyl hydrazine hydrochloride, benzyl hydrazine and isopropyl hydrazine hydrochloride which can be prepared readily by someone skilled in the art.

In step 4, scheme 1 the phthalic anhydride derivatives of formula IV are converted with the appropriate hydrazine derivatives into their corresponding N-aminophthalimides of formula V, using methods well known to someone skilled in the art. The reaction is typically carried out in aprotic solvents such as THF, DMF, NMP or protic solvents such as HOAc, EtOH, MeOH and IPA and mixtures thereof at temperatures between 0° C. and 120° C. Typically used hydrazine derivatives are aromatic hydrazines, and salts thereof such as 2-chlorophenyl hydrazine, 3-nitrophenyl hydrazine, 4-nitrophenyl hydrazine and 4-carboxyethylphenyl hydrazine which can be prepared readily by someone skilled in the art.

In step 5, scheme 1 the obtained compounds of formula V are converted into their corresponding phthalazinones of formula VI, using methods well known to someone skilled in the art, e.g. ring expansion. The reaction is typically carried out in protic solvents such as glycerol, sulphuric acid and HCl at temperatures between 100° C. and 160° C.

In step 6, scheme 1 the obtained compounds of formula VI are converted into their corresponding phthalazinones of formula VII, using methods well known to someone skilled in the art, e.g. iminobromide formation from secondary amides using the methods described for step 1 of scheme 1.

In step 7a, scheme 1 the obtained compounds of formula VII are converted into their corresponding aminopyrazole I, using methods well known to someone skilled in the art, e.g. palladium-mediated amination of iminobromides, vinylbromide or aryl bromides. The reaction is typically carried out in solvents such as THF, dioxane, toluene, alkanols such as MeOH, EtOH, IPA, and mixtures thereof at temperatures between 40° C. and 110° C. Typically used bases are cesium carbonate, triethylamine (TEA), sodium tert-butoxide and appropriate ligated palladium (0) species can be generated using reagents such as palladium acetate, palladium dichloride, tris(dibenzylideneacetone)dipalladium, palladium tetrakis-triphenylphospine, bis-triphenylphosphinepalladium dichloride in conjunction with phosphine based ligands such as 2,2'-bis(diphenylphosphino)-1,1'-binaphthyl, 4,5-bis(diphenylphosphino)-9,9-dimethylxanthene and 2-(di-tert-butylphosphino)biphenyl.

Alternatively, compounds of formula I are obtained from compounds VII in a two step procedure:

In step 7b, scheme 1, the compounds of formula VII are converted into the corresponding protected aminopyrazoles I-protected, by coupling with an aminopyrazole derivative of formula VIII-a, using the same methods as described for step 7a. In formulas I-protected and VIII-a PG stands for a protecting group like tert.-butyl or para-methoxybenzyl or tert.-butoxycarbonyl, which is attached to the pyrazole ring either via N-1 or N-2.

In step 8, scheme 1, the protecting group PG in compounds of formula I-protected is cleaved to give the aminopyrazole I. This can be done by standard deprotecting methods like heating in the presence of an acid like formic acid or HCl. If the protecting group PG is a tert.-butoxycarbonyl group, the cleavage may already occur during the work-up of reaction step 7b.

A preferred method for the synthesis of the derivatives of formula I, wherein $R^5$ is phenyl which is substituted at the para- or meta-position with —$NH_2$ or —NH—R' and R' is —C(O)-aryl, —C(O)-cycloalkyl, —C(O)-alkyl, —C(O)-alkoxyalkyl, —S(O)$_2$-aryl, —S(O)$_2$-alkyl, is described in scheme 2. The derivatives of formula I, wherein $R^5$ is phenyl which is substituted at the para- or meta- position with —NH-R' and R' is —C(O)-aryl, —C(O)-cycloalkyl, —C(O)-alkyl, —C(O)-alkoxyalkyl, —S(O)$_2$-aryl, —S(O)$_2$-alkyl, are named I-a in scheme 2.

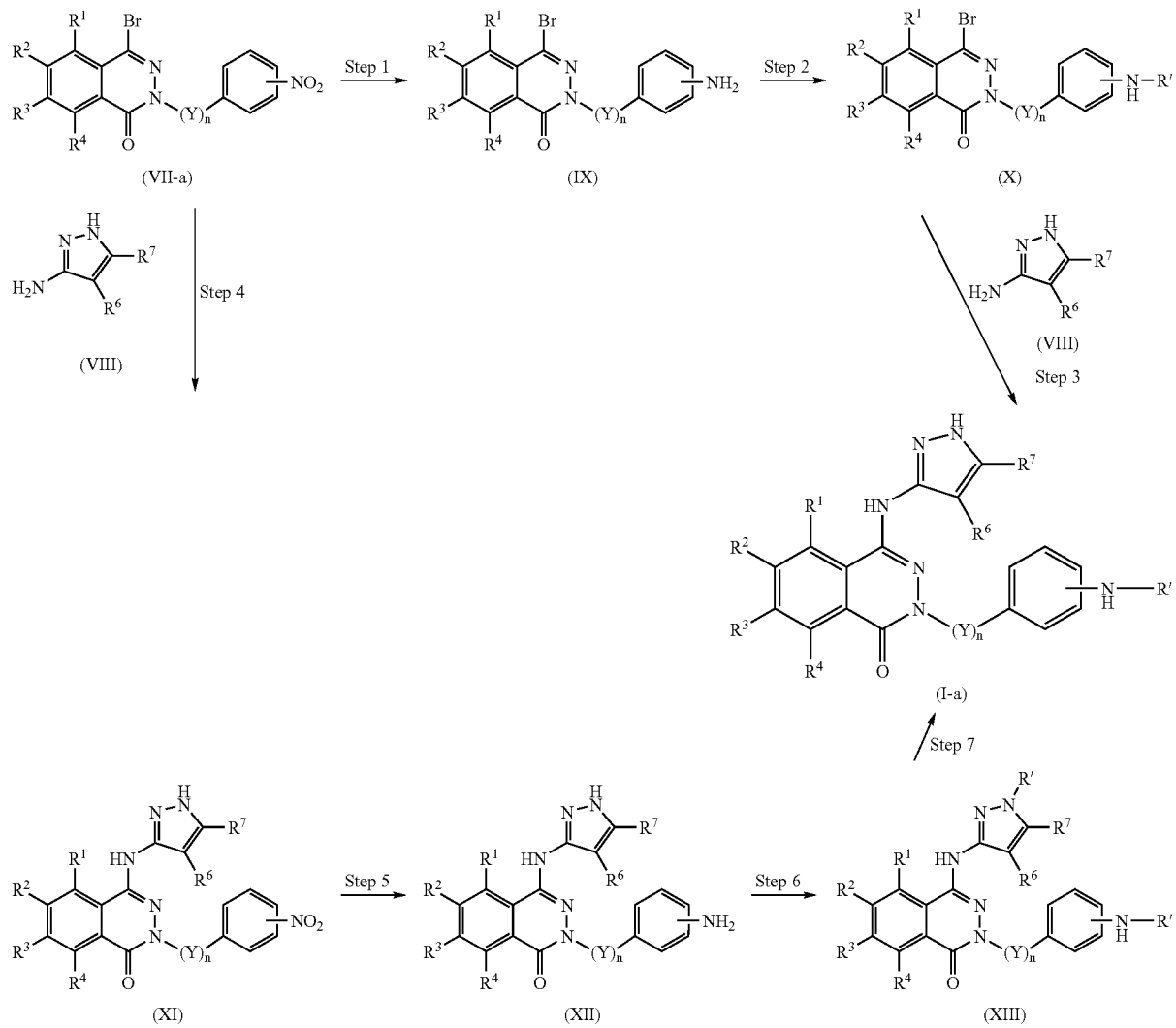

The method for the synthesis of the compounds of formula I-a starts from the corresponding nitrophenyl derivative of formula VII-a. In step 1, scheme 2 the obtained compounds of formula VII-a (see scheme 1) are converted into their corresponding anilines of formula IX, using methods well known to someone skilled in the art, e.g. aniline formation by the reduction of nitrobenzenes. The reaction is typically carried out in solvents like DMF, NMP, acetonitrile (MeCN), HOAc, EtOH and MeOH, and mixtures thereof, at temperatures between 20° C. and 100° C. Typically used reducing reagents are tin(II) chloride, tin(II) chloride monohydrate, iron trichloride.

In step 2, scheme 2 the obtained compounds of formula IX are converted into their corresponding amides, sulfonamides or ureas of formula X, using methods well known to someone skilled in the art, e.g. sulfonylation, acylation or aminocarboxylation of anilines. The reaction is typically carried out in aprotic solvents such as DCM, EtOH, THF, DMF, DMSO, NMP and mixtures thereof at temperatures between 0° C. and 80° C. Typically used bases are TEA, DIPEA, pyridine, potassium carbonate and 4-(dimethylamino)pyridine (DMAP).

In step 3, scheme 2 the obtained compounds of formula X are converted into their corresponding aminopyrazole Ia, using methods described for step 7a of scheme 1.

In step 4, scheme 2 the bromophthalazinone compounds of formula VII-a are converted into their corresponding aminopyrazole XI, using methods well known to someone skilled in the art using the methods described for step 7a of scheme 1.

In step 5, scheme 2 the obtained compounds of formula XI are converted into their corresponding anilines of formula XII, using methods well known to someone skilled in the art as described for step 1 of scheme 2.

In step 6, scheme 2 the obtained compounds of formula XII are converted into their corresponding bis-amides, -sulfonamides or -ureas of formula XIII using the methods described for step 2 of scheme 2.

In step 7, scheme 2 the obtained compounds of formula XIII are converted into their corresponding amides, sulfonamides or ureas of formula Ia, using methods well known to someone skilled in the art, e.g. hydrolysis of pyrazoloamides, pyrazolosulfonamides and pyrazoloureas. The reaction is typically carried out in protic solvents such as water, MeOH and EtOH or aprotic solvents such as MeCN, DCM, THF, DMF, NMP and mixtures thereof at temperatures between 0° C. and 80° C. Typically used bases are ammonia, potassium hydroxide, sodium hydroxide and lithium hydroxide.

A preferred method for the synthesis of the derivatives of formula I, wherein $R^5$ is phenyl which is substituted at the para- or meta-position with —COOH or —C(O)—R" and R" is —NH-aryl, —NH$_2$, —NH-alkyl, —N(alkyl)$_2$, -heterocyclyl, —NH—S(O)$_2$-aryl, —NH—S(O)$_2$-alkyl, is described in scheme 3. The derivatives of formula I, wherein $R^5$ is phenyl which is substituted at the para- or meta-position with —C(O)-R' and R' is —NH-aryl, —NH$_2$, —NH-alkyl, —N(alkyl)$_2$, -heterocyclyl, —NH—S(O)$_2$-aryl, —NH—S(O)$_2$-alkyl, are named I-b in scheme 3.

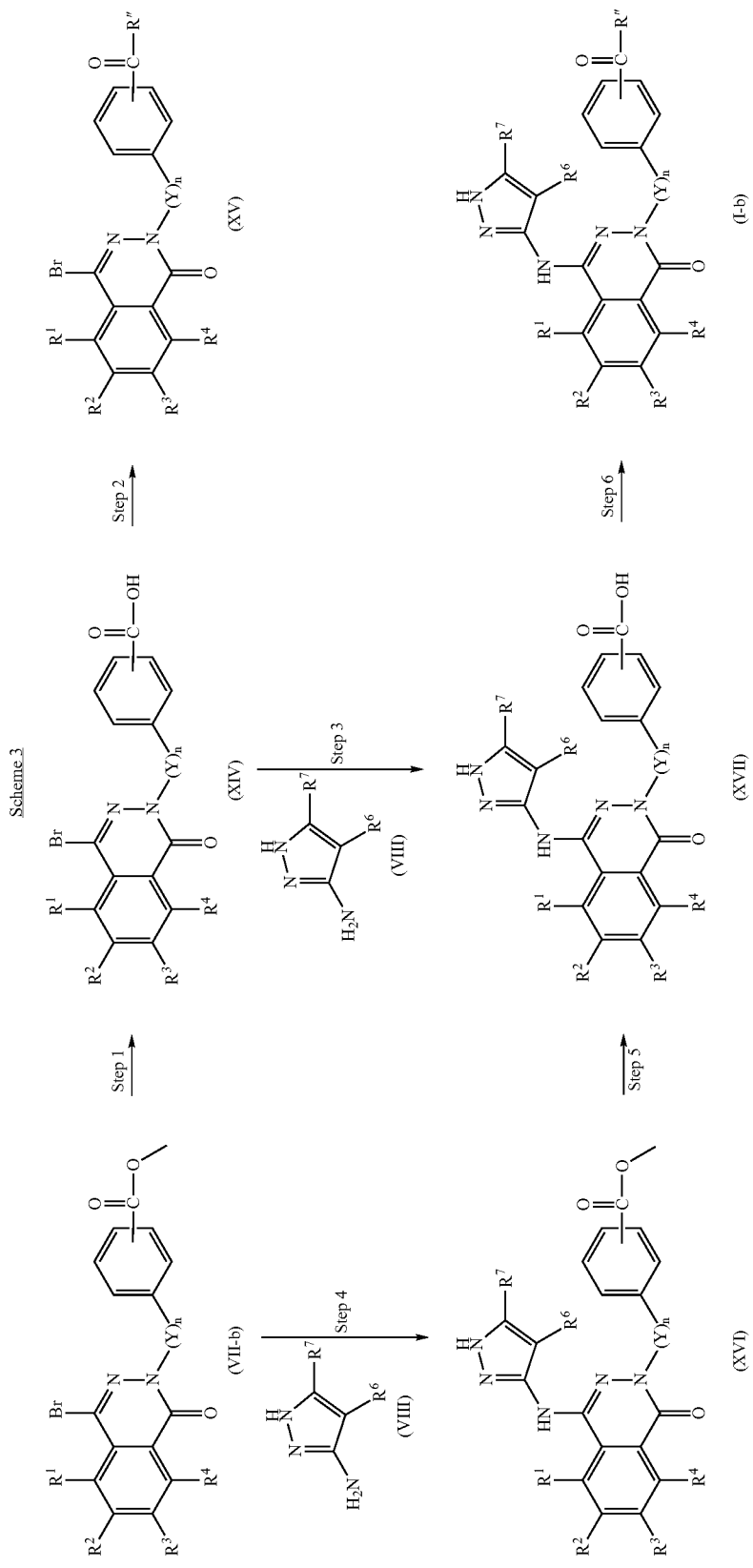

The method for the synthesis of the compounds of formula I-b starts from the corresponding carboxyalkyl derivative of formula VII-b. In step 1, scheme 3 the obtained compounds of formula VII-b (see scheme I) are converted into their corresponding carboxylic acids of formula XIV, using methods well known to someone skilled in the art, e.g. carboxylic acid formation by hydrolysis of alkyl carboxylates. The reaction is typically carried out in solvents like THF, EtOH and MeOH, water and mixtures thereof, at temperatures between 20° C. and 60° C. Typically used hydrolysis reagents are lithium hydroxide, sodium hydroxide and potassium hydroxide.

In step 2, scheme 3 the obtained compounds of formula XIV are converted into their corresponding carboxamide or acylsulfonamides of formula XV, using methods well known to someone skilled in the art, e.g. acylation of amines and sulfonamides. The reaction is typically carried out in aprotic solvents such as DCM, EtOH, THF, DMF, DMSO, NMP and mixtures thereof at temperatures between 0° C. and 80° C. Typically used coupling agents are N,N'-dicyclohexylcarbodiimide (DCC), 1-(3-dimethylaminopropyl)-3-ethylcarbodiimide hydrochloride (EDCl), O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate. The reaction can be performed in the absence of a base or in the presence of a base. Typically used bases are TEA, DIPEA, pyridine, potassium carbonate and DMAP.

In step 3, scheme 3 the obtained compounds of formula XV are converted into their corresponding aminopyrazole Ib, using methods well known to someone skilled in the art as described for step 7a of scheme 1.

In step 4, scheme 3 the bromophthalazinone compounds of formula VIIb are converted into their corresponding aminopyrazole XVI, using methods well known to someone skilled in the art as described for step 7a of scheme 1.

In step 5, scheme 3 the obtained compounds of formula XVI are converted into their corresponding carboxylic acids of formula XVII, using methods well known to someone skilled in the art as described for step 1 of scheme 3.

In step 6, scheme 3 the obtained compounds of formula XVII are converted into their corresponding carboxamide or acylsulfonamides of formula Ib, using methods well known to someone skilled in the art, e.g. acylation of amines and sulfonamides as described for step 2 of scheme 3.

A preferred method for the synthesis of the derivatives of formula I, wherein one of $R^1$ to $R^4$ is —$NH_2$ or $R^8$—$X^I$—, with $X^I$ being —NH— or —NH(alkyl)-, one of $R^1$ to $R^4$ is R''', with R''' being defined as $R^1$ to $R^4$ above for formula I and the remaining two of $R^1$ to $R^4$ are hydrogen, is described in scheme 4. The derivatives of formula (I), wherein one of $R^1$ to $R^4$ is $R^8$—$X^I$—, with $X^I$ being —NH— or —NH(alkyl)-, one of $R^1$ to $R^4$ is R''', with R''' being defined as $R^1$ to $R^4$ above for formula I and the remaining two of $R^1$ to $R^4$ are hydrogen, are named I-c in scheme 4.

Scheme 4

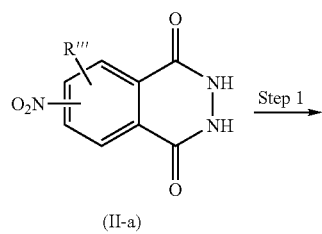

(II-a)

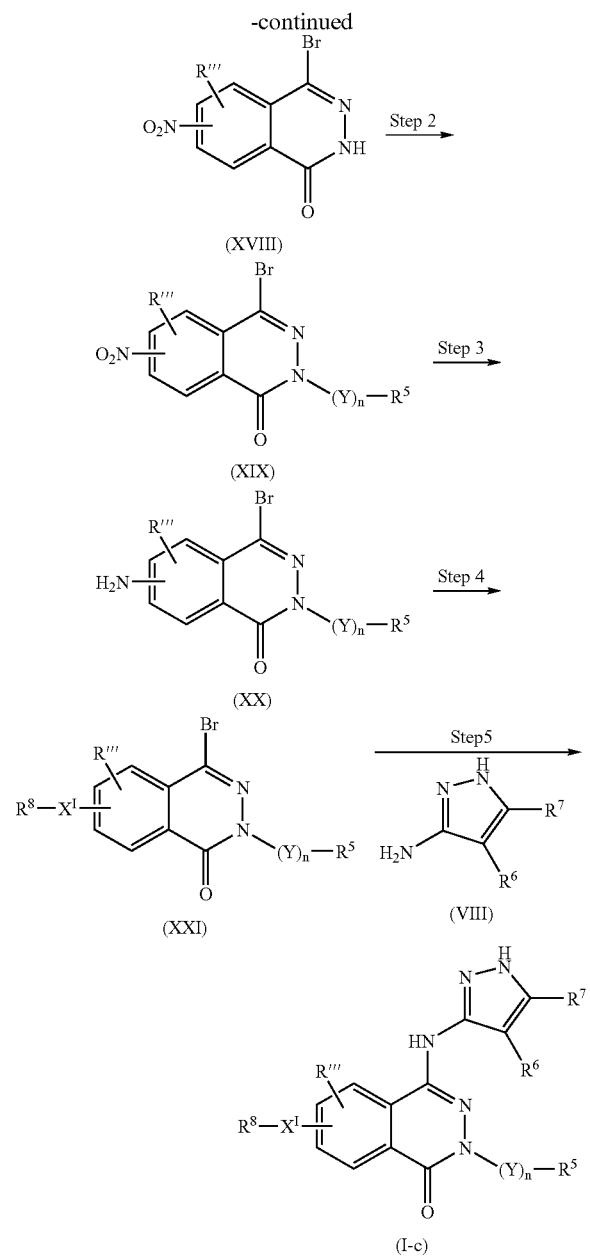

The method for the synthesis of the compounds of formula I-c starts from the corresponding phthalazine diones of formula II-a. Step 1 of the reaction sequence (scheme 4) is a two step process in which a dibromination is followed by a mono-hydrolysis, yielding the 4-bromo-nitrophthalazinone derivatives of formula XVIII.

The steps are carried out as described in step 1 of scheme 1.

In step 2, scheme 4 the obtained compounds of formula XVIII are converted into their corresponding tertiary amides of formula XIX, using methods well known to someone skilled in the art, e.g. alkylation under basic conditions as described in step 2 of scheme 1.

In step 3, scheme 4 the obtained compounds of formula XIX are converted into their corresponding anilines of formula XX, using methods well known to someone skilled in the art, e.g. aniline formation by the reduction of nitrobenzenes as described in step 1 of scheme 2.

In step 4, scheme 4 the obtained compounds of formula XX are converted into their corresponding secondary or tertiary amines of formula XXI, using methods well known to someone skilled in the art, e.g. alkylation of amines. The reaction is typically carried out in aprotic solvents such as THF, DMF, DMSO, NMP and mixtures thereof at temperatures between −78° C. and 100° C. Typically used bases are potassium carbonate, sodium hydride, potassium hydride, lithium hexamethyldisilazide, sodium hexamethyldisilazide, potassium hexamethyl-disilazide.

Eventually it is necessary to introduce an intermediary N-protecting group like t-butyloxycarbonyl (BOC), which is cleaved after the alkylation step, to obtain the monoalkylated amines. These monoalkylated amines can be used, if desired, as educts for a second alkylation step (for introduction/deprotection of the BOC-group see also schemes 7 and 8).

In step 5, scheme 4 the bromophthalazinone compounds of formula XXI are converted into their corresponding aminopyrazole Ic, using methods well known to someone skilled in the art, e.g. palladium-mediated amination of iminobromides, vinylbromide or aryl bromides as described for step 7a of scheme 1.

A method for the synthesis of the derivatives of formula I, wherein one of $R^1$ to $R^4$ is $R^8$—$X^{II}$—, with $X^{II}$ being —C(O)NH—, —NHC(O)NH— or —S(O)$_2$NH—, one of $R^1$ to $R^4$ is R''', with R''' being defined as $R^1$ to $R^4$ above for formula I and the remaining two of $R^1$ to $R^4$ are hydrogen, is described in scheme 5. The derivatives of formula I, wherein one of $R^1$ to $R^4$ is $R^8$—$X^{II}$—, with $X^{II}$ being —C(O)NH—, —NHC(O)NH— or —S(O)$_2$NH—, one of $R^1$ to $R^4$ is R''', with R''' being defined as $R^1$ to $R^4$ above for formula I and the remaining two of $R^1$ to $R^4$ are hydrogen, are named I-d in scheme 5.

Scheme 5

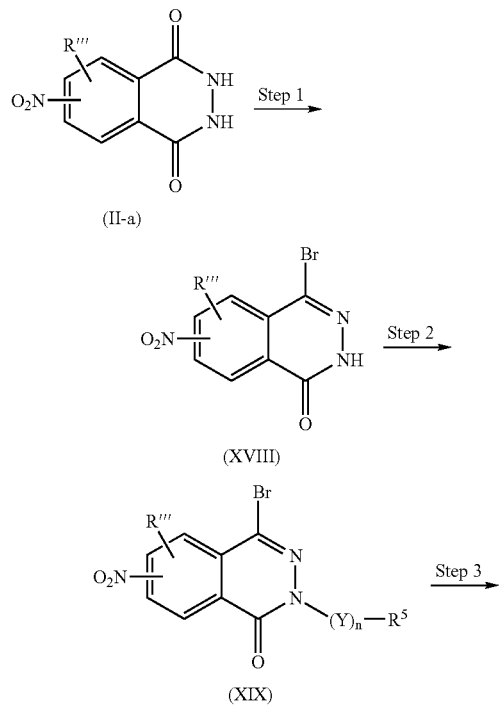

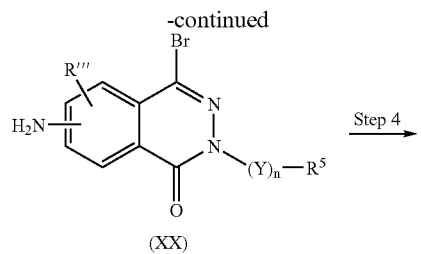

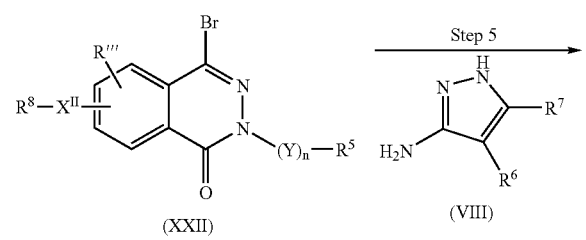

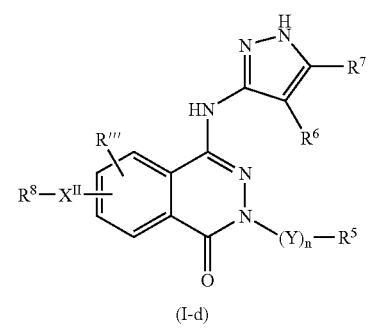

The method for the synthesis of the compounds of formula I-d starts from the corresponding phthalazine diones of formula II-a. Step 1 to step 3 are the same as described for scheme 4 yielding the corresponding amines of formula XX.

In step 4, scheme 5 the obtained compounds of formula XX are converted into their corresponding amides, sulfonamides or ureas of formula XXII, using methods well known to someone skilled in the art, e.g. sulfonylation, acylation or aminocarboxylation of anilines as described in step 2 of scheme 2.

In step 5, scheme 5 the bromophthalazinone compounds of formula XXII are converted into their corresponding aminopyrazole Id, using methods well known to someone skilled in the art, e.g. palladium-mediated amination of iminobromides, vinylbromide or aryl bromides as described in step 7a of scheme 1.

A preferred method for the synthesis of the derivatives of formula I, wherein one of $R^1$ to $R^4$ is —C(O)OH or $R^8$—X'''—, with X''' being —NHC(O)—, —N(alkyl)C(O)— or —OC(O)—, one of $R^1$ to $R^4$ is R''', with R''' being defined as $R^1$ to $R^4$ above for formula I and the remaining two of $R^1$ to $R^4$ are hydrogen, is described in scheme 6. The derivatives of formula I, wherein one of $R^1$ to $R^4$ is $R^8$—X'''—, with X''' being —NHC(O)—, —N(alkyl)C(O)— or —OC(O)—, one of $R^1$ to $R^4$ is R''', with R''' being defined as $R^1$ to $R^4$ above for formula I and the remaining two of $R^1$ to $R^4$ are hydrogen, are named I-e in scheme 6.

Scheme 6

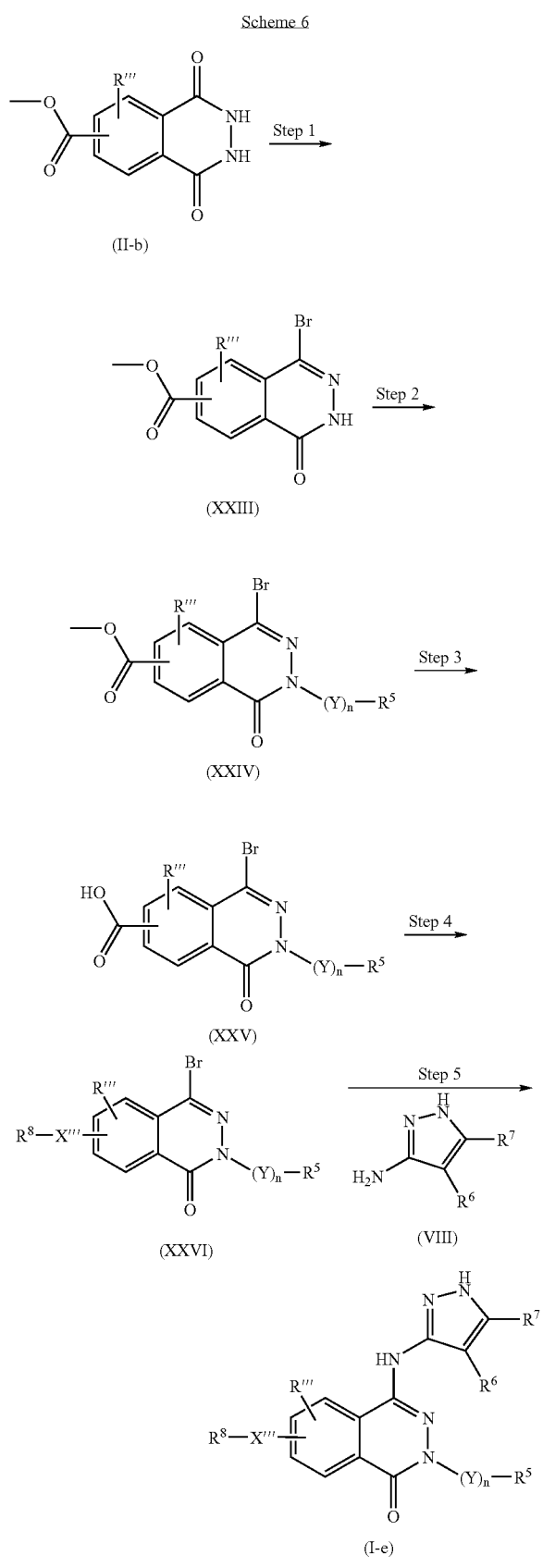

A preferred method for the synthesis of the compounds of formula I-e starts from the corresponding phthalazine diones of formula II-b. Step 1 of the reaction sequence (scheme 6) is a two step process in which a dibromination is followed by a monohydrolysis, yielding the 4-bromo-alkylcarboxyphthalazinone derivatives of formula XXIII as described in stepp 1 of scheme 1.

In step 2, scheme 6 the obtained compounds of formula XXIII are converted into their corresponding tertiary amides of formula XXIV, using methods well known to someone skilled in the art, e.g. alkylation under basic conditions as described in step 2 of scheme 1.

In step 3, scheme 6 the obtained compounds of formula XXIV are converted into their corresponding carboxylic acids of formula XXV, using methods well known to someone skilled in the art, e.g. carboxylic acid formation by hydrolysis of alkyl carboxylates as described in Step 1 of scheme 3.

In step 4, scheme 6 the obtained compounds of formula XXV are converted into their corresponding carboxamide, acylsulfonamides or carboxylic acid esters of formula XXVI, using methods well known to someone skilled in the art, e.g. acylation of amines, sulfonamides and alcohols as described in step 2 of scheme 3.

In step 5, scheme 6 the bromophthalazinone compounds of formula XXVI are converted into their corresponding aminopyrazole Ie, using methods well known to someone skilled in the art, e.g. palladium-mediated amination of iminobromides, vinylbromide or aryl bromides as described in step 7a of scheme 1.

A preferred method for the synthesis of the derivatives of formula I, wherein one of $R^1$ to $R^4$ is $R^8$—$X^{IV}$—, with $X^{IV}$ being —C(O)NH—, —NHC(O)NH— or —S(O)$_2$NH— and —C(O)N(alkyl)-, —NHC(O)N(alkyl)- or —S(O)$_2$N(alkyl)-, one of $R^1$ to $R^4$ is R''', with R''' being defined as $R^1$ to $R^4$ above for formula I, and the remaining two of $R^1$ to $R^4$ are hydrogen, $R^6$ is hydrogen and $R^7$ is methyl, is described in scheme 7. The derivatives of formula I, wherein one of $R^1$ to $R^4$ is $R^8$—$X^{IV}$—, with $X^{IV}$ being —C(O)NH—, —NHC(O)NH— or —S(O)$_2$NH— and —C(O)N(alkyl)-, —NHC(O)N(alkyl)- or —S(O)$_2$N(alkyl)-, one of $R^1$ to $R^4$ is R''', with R''' being defined as $R^1$ to $R^4$ above for formula I and the remaining two of $R^1$ to $R^4$ are hydrogen, $R^6$ is hydrogen and $R^7$ is methyl, are named I-f in scheme 7.

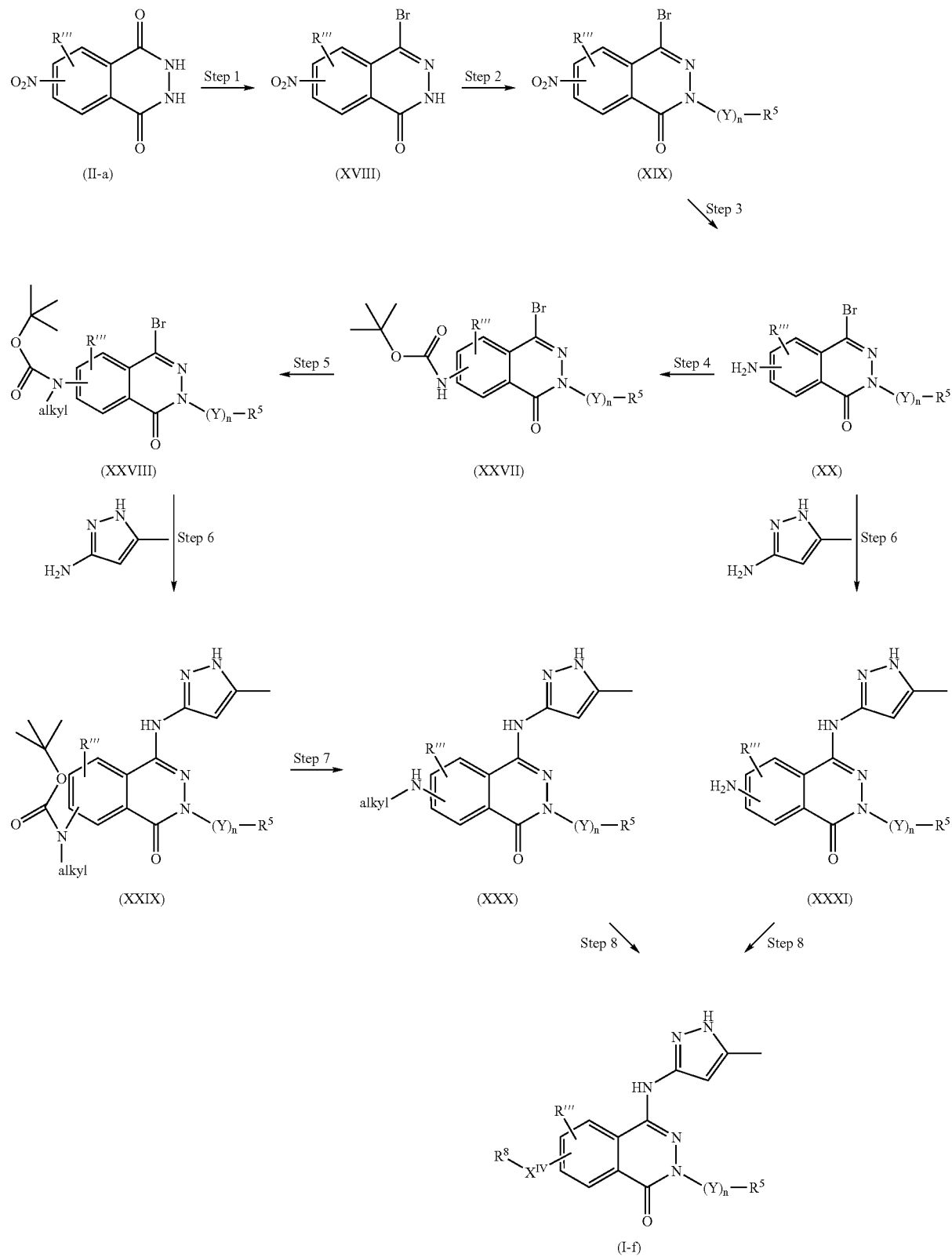

A preferred method for the synthesis of the compounds of formula I-f starts from the corresponding phthalazine diones of formula II-a. Step 1 of the reaction sequence (scheme 7) is a two step process in which a dibromination is followed by a monohydrolysis, yielding the 4-bromo-nitrophthalazinone derivatives of formula XVIII as described in step 1 of scheme 1.

In step 2, scheme 7 the obtained compounds of formula XVIII are converted into their corresponding tertiary amides of formula XIX, using methods well known to someone skilled in the art, e.g. alkylation under basic conditions as described in step 2 of scheme 1.

In step 3, scheme 7 the obtained compounds of formula XIX are converted into their corresponding anilines of formula XX, using methods well known to someone skilled in the art, e.g. aniline formation by the reduction of nitrobenzenes as described in step 1 of scheme 2.

In step 4, scheme 7 the obtained compounds of formula XX are converted into their corresponding secondary carbamates of formula XXVII, using methods well known to someone skilled in the art, e.g. tert-butyloxycarbonylation of amines. The reaction is typically carried out in solvents like DMF, NMP, MeCN, DCM and DCE, at temperatures between 0° C. and 100° C. Typically used bases are imidazole, TEA, N,N-diisopropylethylamine (DIPEA) and N,N-dimethylamino-pyridine in conjunction with reagents such as di-tert-butyl dicarbonate.

In step 5, scheme 7 the obtained compounds of formula XXVII are converted into their corresponding tertiary carbamates of formula XXVIII, using methods well known to someone skilled in the art, e.g. alkylation of secondary carbamates. The reaction is typically carried out in solvents like DMF, NMP, MeCN, DCM and DCE, at temperatures between 0° C. and 100° C. Typically used bases are potassium carbonate, sodium hydride, lithium hexamethyldisilazide, sodium hexamethyldisilazide and potassium hexamethyldisilazide in conjunction with alkylating agents such as alkyl halides, alkyl mesylates and alkyl triflates.

In step 6, scheme 7 the obtained compounds of formula XXVIII (obtained in step 5) or compounds of formula XX (obtained in step 3) are converted into their corresponding amino pyrazoles of formula XXIX or formula XXXI, using methods well known to someone skilled in the art, e.g. palladium-mediated amination of iminobromides, vinylbromides or aryl bromides as described for step 7a of scheme 1.

In step 7, scheme 7 the obtained compounds of formula XXIX are converted into their corresponding anilines of formula XXX, using methods well known to someone skilled in the art, e.g. acid mediated de-protection of a boc-protected amine. The reaction is typically carried out in solvents such as DCM, dioxane, diethyl ether, dioxane and alkyl alcohols such as MeOH, EtOH and mixtures thereof at temperatures between 0° C. and 40° C. Typically used acids are anhydrous HCl, aqueous HCl, TFA, trimethylsilyl bromide and trifluoromethanesulfonic acid.

In step 8, scheme 7 the obtained compounds of formula XXX or formula XXXI are converted into their corresponding amides, sulfonamides or ureas of formula (I-f), using a two step procedure in which a bis acylation (of the amine of formula XXX or formula XXXI and the pyrazole-NH) is followed by a monohydrolysis (of the acylated pyrazole-NH), yielding the aminopyrazole derivatives of formula I-f. The first step (bis acylation) is typically carried out in solvents such as DCM, dioxane, and THF and mixtures thereof at temperatures between 0° C. and 80° C. using capping reagents such as acid chlorides, acid anhydrides, sulfonyl chlorides and isocyanates. Typically used bases are TEA, DIPEA and DMAP, potassium carbonate, sodium hydride, lithium hexamethyldisilazide, sodium hexamethyldisilazide and potassium hexamethyldisilazide at temperatures between 0° C. and 80° C. The second step (monohydrolysis of the diamide, disulfonamide, diurea) is typically carried out in aqueous conditions in solvents such as water, aqueous lithium hydroxide, aqueous sodium hydroxide, aqueous potassium hydroxide, aqueous sodium hydrogen carbonate, aqueous sodium carbonate, aqueous potassium hydrogen carbonate, aqueous potassium carbonate at temperatures between 0° C. and 80° C.

A preferred method for the synthesis of the derivatives of formula I, wherein one of $R^1$ to $R^4$ is $R^8—X^V—$, with $X^V$ being —N(alkyl)-, one of $R^1$ to $R^4$ is R''', with R''' being defined as $R^1$ to $R^4$ above for formula I, and the remaining two of $R^1$ to $R^4$ are hydrogen, $R^6$ is hydrogen and $R^7$ is methyl, is described in scheme 7. The derivatives of formula I, wherein one of $R^1$ to $R^4$ is $R^8—X^{IV}—$, with $X^V$ being —N(alkyl)-, one of $R^1$ to $R^4$ is R''', with R''' being defined as $R^1$ to $R^4$ above for formula I and the remaining two of $R^1$ to $R^4$ are hydrogen, $R^6$ is hydrogen and $R^7$ is methyl, are named I-g in scheme 8.

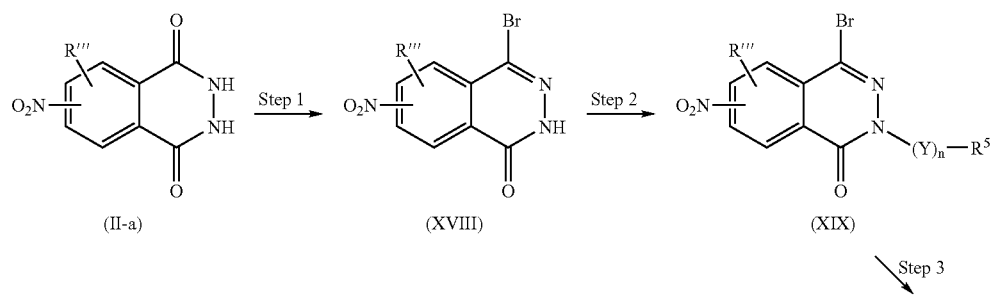

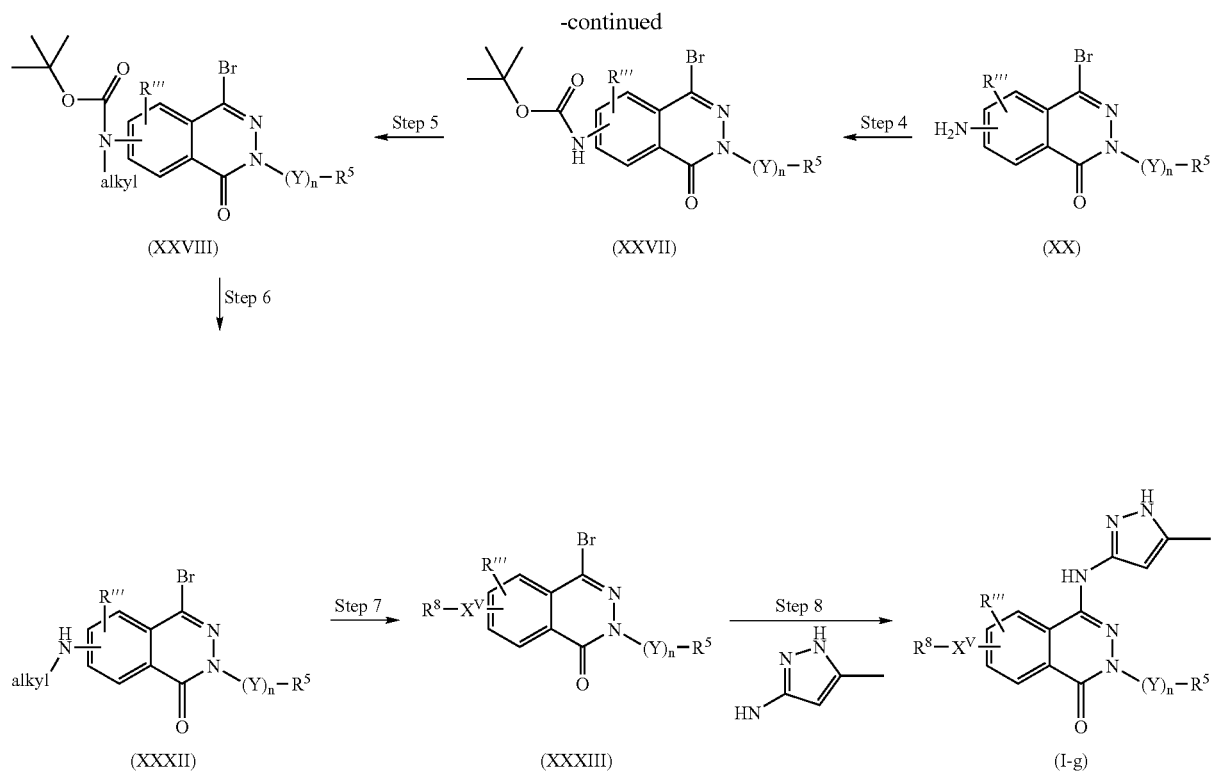

A preferred method for the synthesis of the compounds of formula I-g starts from the corresponding phthalazine diones of formula II-a. Step 1 of the reaction sequence (scheme 8) is a two step process in which a dibromination is followed by a monohydrolysis, yielding the 4-bromo-nitrophthalazinone derivatives of formula XVIII as described in step 1 of scheme 1.

In step 2, scheme 8 the obtained compounds of formula XVIII are converted into their corresponding tertiary amides of formula XIX, using methods well known to someone skilled in the art, e.g. alkylation under basic conditions as described in step 2 of scheme 1.

In step 3, scheme 8 the obtained compounds of formula XIX are converted into their corresponding anilines of formula XX, using methods well known to someone skilled in the art, e.g. aniline formation by the reduction of nitrobenzenes as described in step 1 of scheme 2.

In step 4, scheme 8 the obtained compounds of formula XX are converted into their corresponding secondary carbamates of formula XXVII, using methods well known to someone skilled in the art, e.g. tert-butyloxycarbonylation of amines as described in step 4 of scheme 7.

In step 5, scheme 8 the obtained compounds of formula XXVII are converted into their corresponding tertiary carbamates of formula XXVIII, using methods well known to someone skilled in the art, e.g. alkylation of secondary carbamates as described in step 5 of scheme 7.

In step 6, scheme 8 the obtained compounds of formula XXVIII are converted into their corresponding secondary amines of formula XXXII, using methods well known to someone skilled in the art, e.g. deprotection of acid labile protecting groups such as a tert-butyloxycarbonyl group. The reaction is typically carried out without solvent or in solvents like diethyl ether, dioxane, THF, DCM and DCE or mixtures thereof, at temperatures between 0° C. and 40° C. Typically used acids are HOAc, TFA, trifluoromethane sulfonic acid, aqueous HCl, aqueous sulfuric acid or anhydrous hydrogen chloride.

In step 7, scheme 8 the obtained compounds of formula XXXII are converted into their corresponding of formula XXXIII, using methods well known to someone skilled in the art, e.g. alkylation of secondary amines as described in step 4 of scheme 4.

In step 8, scheme 8 the obtained compounds of formula (XXXIII) are converted into their corresponding amino pyrazoles of formula I-g, using methods well known to someone skilled in the art, e.g. palladium-mediated amination of iminobromides, vinylbromides or aryl bromides as described in step 7a of scheme 1.

A preferred method for the synthesis of the derivatives of formula I, wherein one of $R^1$ to $R^4$ is —OH or $R^8$—$X^{VI}$—, with $X^{VI}$ being —O— or —C(O)O—, one of $R^1$ to $R^4$ is R''', with R''' being defined as $R^1$ to $R^4$ above for formula I, and the remaining two of $R^1$ to $R^4$ are hydrogen, $R^6$ is hydrogen and $R^7$ is methyl, is described in scheme 9. The derivatives of formula (I), wherein one of $R^1$ to $R^4$ is $R^8$—$X^{IV}$—, with $X^{IV}$ being —O— or —C(O)O—, one of $R^1$ to $R^4$ is R'''', with R'''' being defined as $R^1$ to $R^4$ above for formula I and the remaining two of $R^1$ to $R^4$ are hydrogen, $R^6$ is hydrogen and $R^7$ is methyl, are named I-h in scheme 9.

Scheme 9

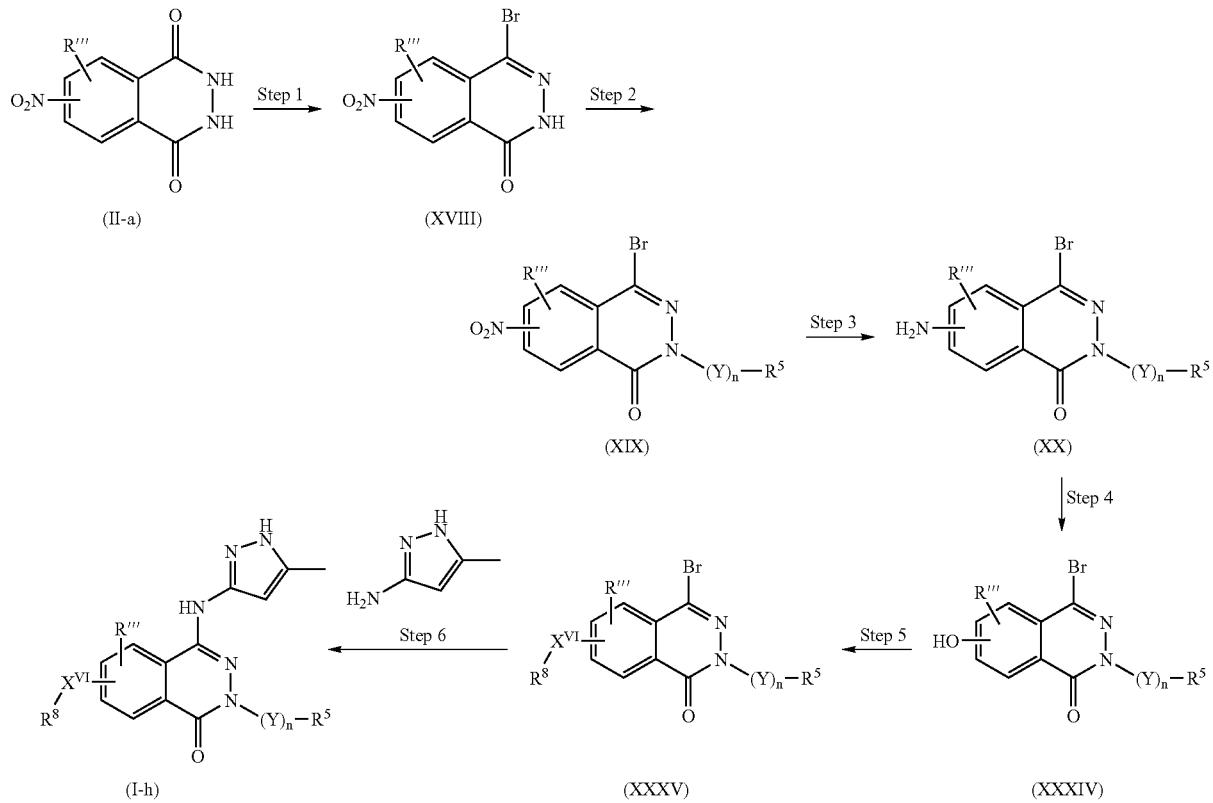

A preferred method for the synthesis of the compounds of formula I-h starts from the corresponding phthalazine diones of formula II-a. Step 1 of the reaction sequence (scheme 9) is a two step process in which a dibromination is followed by a monohydrolysis, yielding the 4-bromo-nitrophthalazinone derivatives of formula XVIII as described in step 1 of scheme 1.

In step 2, scheme 9 the obtained compounds of formula XVIII are converted into their corresponding tertiary amides of formula XIX, using methods well known to someone skilled in the art, e.g. alkylation under basic conditions as described in step 2 of scheme 1.

In step 3, scheme 9 the obtained compounds of formula XIX are converted into their corresponding anilines of formula XX, using methods well known to someone skilled in the art, e.g. aniline formation by the reduction of nitrobenzenes as described in step 1 of scheme 2.

In step 4, scheme 9 the obtained compounds of formula (XX) are converted into their corresponding alcohols of formula XXXIV, using methods well known to someone skilled in the art, e.g. diazotisation of anilines and displacement of the diazonium species with nucleophiles. The reaction is a 2 step process in which step 1 is generation of the diazonium species and step 2 is displacement of the diazonium species is carried out using a nucleophile. Step 1 of the reaction is typically carried out in solvents such as sulfuric acid, HCl or HOAc and mixtures thereof. Typically used reagents are sodium nitrite and isoamylnitrite with additional reagents such as urea. The first step of the reaction is typically carried out at temperatures between −10° C. and 30° C. Step 2 of the reaction is typically carried out in aqueous media such as aqueous HCl, aqueous sulfuric acid and aqueous HOAc. The second step of the reaction is typically carried out at temperatures between 20° C. and 130° C.

In step 5, scheme 9 the obtained compounds of formula XXXIV are converted into their corresponding ethers of formula XXXV, using methods well known to someone skilled in the art, e.g. alkylation of phenols. The reaction is typically carried out in solvents like DMF, THF, NMP, MeCN, acetone, DCM and DCE, at temperatures between 0° C. and 100° C. Typically used bases are potassium carbonate, sodium hydride, lithium hexamethyldisilazide, sodium hexamethyldisilazide and potassium hexamethyldisilazide in conjunction with alkylating agents such as alkyl halides, alkyl mesylates and alkyl triflates.

In step 6, scheme 9 the obtained compounds of formula XXXV are converted into their corresponding amino pyrazoles of formula I-h, using methods well known to someone skilled in the art, e.g. palladium-mediated amination of iminobromides, vinylbromides or aryl bromides as described in step 7a of example 1.

A preferred method for the synthesis of the derivatives of formula I, wherein one of $R^1$ to $R^4$ is $R^8$—S—, or $R^8$—$X^{VII}$—, with $X^{VII}$ being —S(O)— or —S(O)$_2$—, one of $R^1$ to $R^4$ is R''', with R''' being defined as $R^1$ to $R^4$ above for formula I, and the remaining two of $R^1$ to $R^4$ are hydrogen, $R^6$ is hydrogen and $R^7$ is methyl, is described in scheme 10. The derivatives of formula I, wherein one of $R^1$ to $R^4$ is $R^8$—S—, or $R^8$—$X^{VII}$—, with $X^{VII}$ being —S(O)— or —S(O)$_2$—, one of $R^1$ to $R^4$ is R''', with R''' being defined as $R^1$ to $R^4$ above for formula I and the remaining two of $R^1$ to $R^4$ are hydrogen, $R^6$ is hydrogen and $R^7$ is methyl, are named I-i (for one of $R^1$ to $R^4$ is $R^8$—S—) or I-j (for one of $R^1$ to $R^4$ is $R^8$—$X^{VII}$—) in scheme 10.

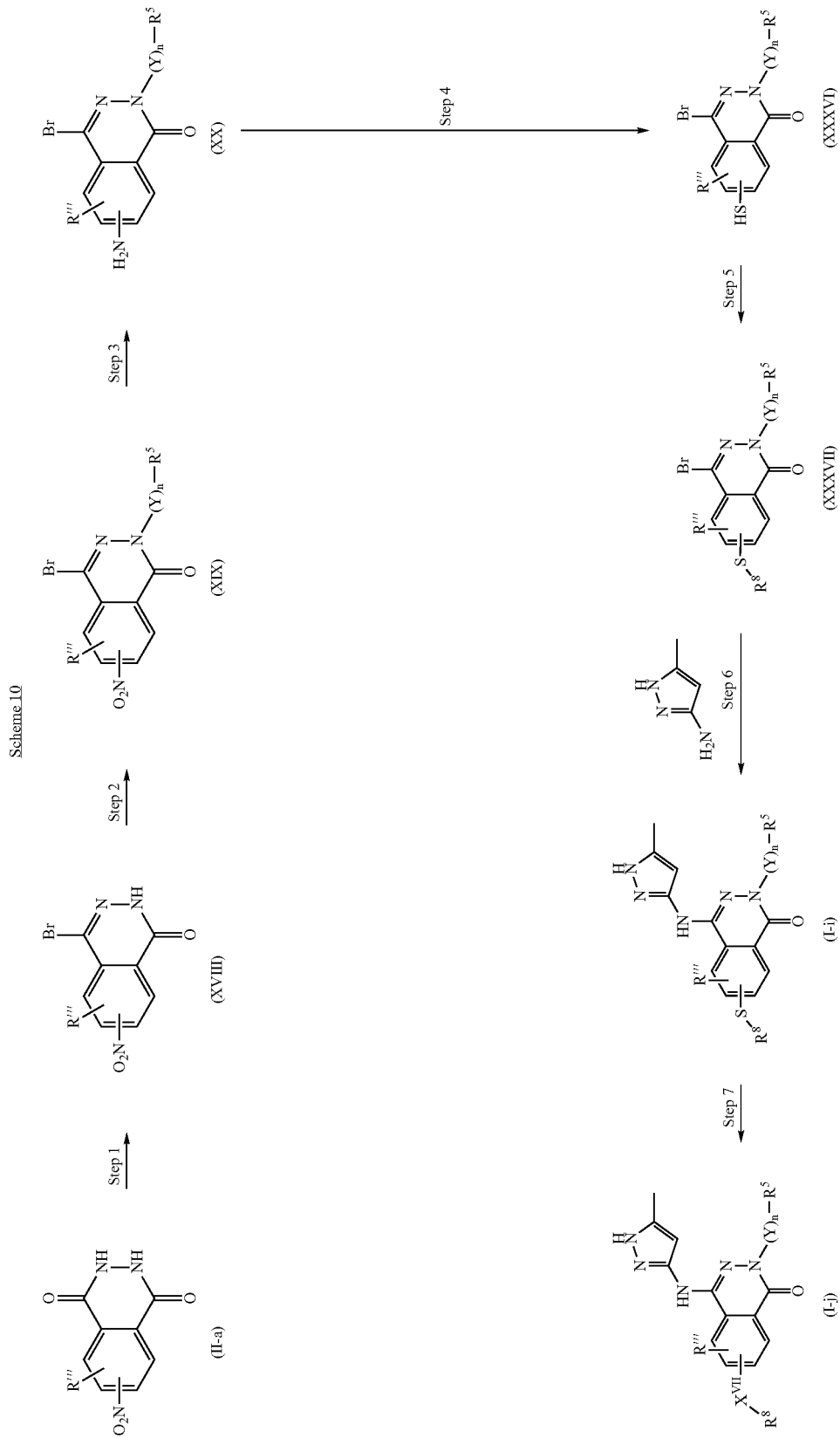

A preferred method for the synthesis of the compounds of formula I-i and I-j starts from the corresponding phthalazine diones of formula II-a. Step 1 of the reaction sequence (scheme 10) is a two step process in which a dibromination is followed by a monohydrolysis, yielding the 4-bromo-nitro-phthalazinone derivatives of formula XVIII as described in step 1 of scheme 1.

In step 2, scheme 10 the obtained compounds of formula XVIII are converted into their corresponding tertiary amides of formula XIX, using methods well known to someone skilled in the art, e.g. alkylation under basic conditions as described in step 2 of scheme 1.

In step 3, scheme 10 the obtained compounds of formula XIX are converted into their corresponding anilines of formula XX, using methods well known to someone skilled in the art, e.g. aniline formation by the reduction of nitrobenzenes as described in step 1 of scheme 2.

In step 4, scheme 10 the obtained compounds of formula XX are converted into their corresponding thiols of formula XXXVI, using methods well known to someone skilled in the art, e.g. diazotisation of anilines and displacement of the diazonium species with nucleophiles. The reaction is a 2 step process in which step 1 is generation of the diazonium species and step 2 is displacement of the diazonium species is carried out using a nucleophile. Step 1 of the reaction is typically carried out in solvents such as sulfuric acid, HCl or HOAc and mixtures thereof. Typically used reagents are sodium nitrite and isoamylnitrite with additional reagents such as urea. The first step of the reaction is typically carried out at temperatures between −10° C. and 30° C. Step 2 of the reaction is typically in aqueous acid in the presence of sulfur nucleophiles such as Na$_2$S or O-ethyl dithiocarbonic acid.

In step 5, scheme 10 the obtained compounds of formula XXXVI are converted into their corresponding ethers of formula XXXVII, using methods well known to someone skilled in the art, e.g. alkylation of thiophenols. The reaction is typically carried out in solvents like DMF, THF, NMP, MeCN, acetone, DCM and DCE, at temperatures between 0° C. and 100° C. Typically used bases are potassium carbonate, sodium hydride, lithium hexamethyldisilazide, sodium hexamethyldisilazide and potassium hexamethyldisilazide in conjunction with alkylating agents such as alkyl halides, alkyl mesylates and alkyl triflates.

In step 6, scheme 10 the obtained compounds of formula XXXVII are converted into their corresponding amino pyrazoles of formula I-i, using methods well known to someone skilled in the art, e.g. palladium-mediated amination of iminobromides, vinylbromides or aryl bromides as described in step 71 of scheme 1.

In step 7, scheme 10 the obtained compounds of formula I-i are converted into their corresponding sulfoxides or sulfones of formula I-j, using methods well known to someone skilled in the art, e.g. oxidation of thioethers to sulfoxides or sulfones. The reaction is typically carried out in solvents such as THF, toluene, alkanols such as MeOH, EtOH, IPA and water and mixtures thereof at temperatures between 0° C. and 110° C. Typically used reagents are OXONE™ and meta-chloroperbenzoic acid.

A preferred method for the synthesis of the derivatives of formula I, wherein one of R$^1$ to R$^4$ is alkyl, especially methyl, substituted with alkoxy, one of R$^1$ to R$^4$ is R''', with R''' being defined as R$^1$ to R$^4$ above for formula I, and the remaining two of R$^1$ to R$^4$ are hydrogen, is described in scheme 11. The derivatives of formula I, wherein one of R$^1$ to R$^4$ is alkyl, especially methyl, substituted with alkoxy, one of R$^1$ to R$^4$ is R''', with R''' being defined as R$^1$ to R$^4$ above for formula I and the remaining two of R$^1$ to R$^4$ are hydrogen, are named I-k in scheme 11.

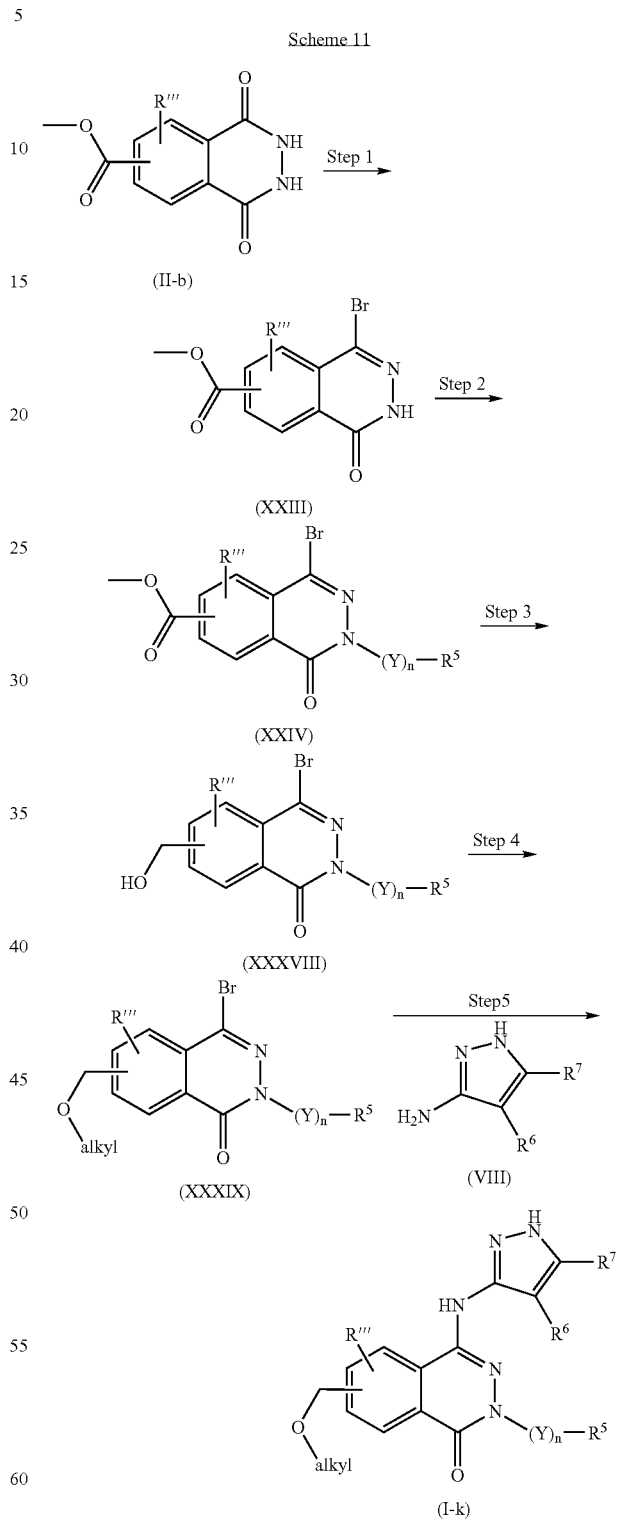

A preferred method for the synthesis of the compounds of formula I-k starts from the corresponding phthalazine diones of formula II-b. Step 1 of the reaction sequence (scheme 11) is a two step process in which a dibromination is followed by a monohydrolysis, yielding the 4-bromo-alkylcarboxyphthalazinone derivatives of formula XXIII as described in step 1 of scheme 1.

In step 2, scheme 11 the obtained compounds of formula XXIII are converted into their corresponding tertiary amides of formula XXIV, using methods well known to someone skilled in the art, e.g. alkylation under basic conditions as described in step 2 of scheme 1.

In step 3, scheme 11 the obtained compounds of formula XXIV are converted into their corresponding alcohols of formula XXXVIII, using methods well known to someone skilled in the art, e.g. reduction of esters to form alcohols. The reaction is typically carried out in solvents like THF, dioxane, DCM and mixtures thereof, at temperatures between 0° C. and 100° C. Typically used reducing reagents are lithium borohydride.

In step 4, scheme 11 the obtained compounds of formula XXXVIII are converted into their corresponding ethers of formula XXXIX, using methods well known to someone skilled in the art, e.g. alkylation of alcohols. The reaction is typically carried out in solvents like DMF, THF, NMP, MeCN, acetone, DCM and DCE, at temperatures between 0° C. and 100° C. Typically used bases are potassium carbonate, sodium hydride, lithium hexamethyldisilazide, sodium hexamethyldisilazide and potassium hexamethyldisilazide in conjunction with alkylating agents such as alkyl halides, alkyl mesylates and alkyl triflates.

In step 5, scheme 11 the obtained compounds of formula XXXIX are converted into their corresponding amino pyrazoles of formula I-k, using methods well known to someone skilled in the art, e.g. palladium-mediated amination of iminobromides, vinylbromides or aryl bromides as described in step 7a of scheme 1.

Another preferred method for the synthesis of the derivatives of formula I, wherein one of $R^1$ to $R^4$ is alkyl, especially methyl, substituted with alkoxy, one of $R^1$ to $R^4$ is $R'''$, with $R'''$ being defined as $R^1$ to $R^4$ above for formula I, and the remaining two of $R^1$ to $R^4$ are hydrogen, is described in scheme 12. The derivatives of formula I, wherein one of $R^1$ to $R^4$ is alkyl, especially methyl, substituted with alkoxy, one of $R^1$ to $R^4$ is $R'''$, with $R'''$ being defined as $R^1$ to $R^4$ above for formula I and the remaining two of $R^1$ to $R^4$ are hydrogen, are named I-k in scheme 12.

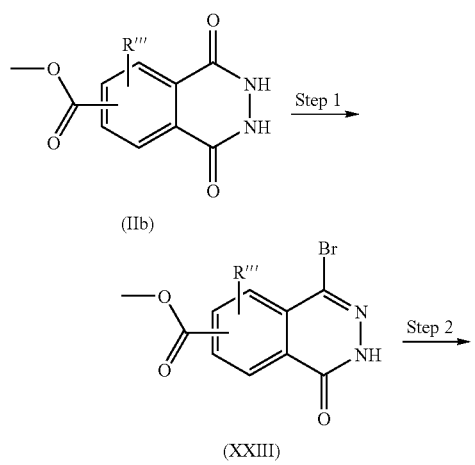

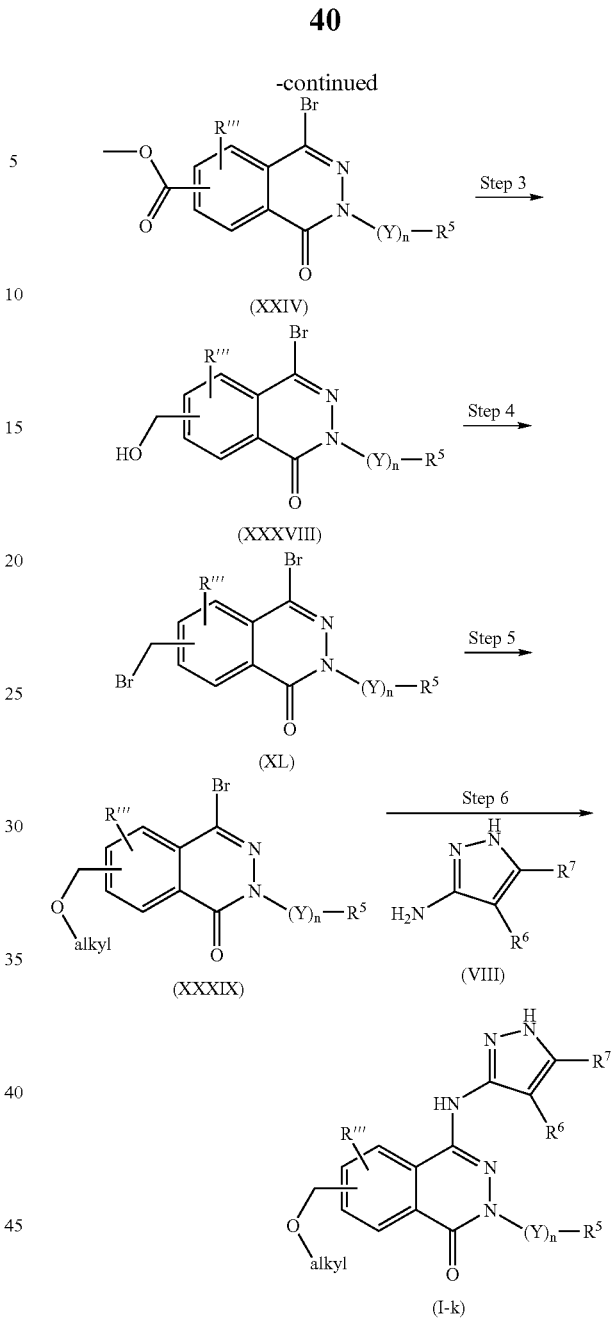

A preferred method for the synthesis of the compounds of formula I-k starts from the corresponding phthalazine diones of formula II-b. Step 1 of the reaction sequence (scheme 12) is a two step process in which a dibromination is followed by a monohydrolysis, yielding the 4-bromo-alkylcarboxyphthalazinone derivatives of formula XXIII as described in step 1 of scheme 1.

In step 2, scheme 12 the obtained compounds of formula XXIII are converted into their corresponding tertiary amides of formula XXIV, using methods well known to someone skilled in the art, e.g. alkylation under basic conditions as described in step 2 of scheme 1.

In step 3, scheme 12 the obtained compounds of formula XXIV are converted into their corresponding alcohols of formula XXXVIII, using methods well known to someone skilled in the art, e.g. reduction of esters to form alcohols as described in step 3 of scheme 11.

In step 4, scheme 12 the obtained compounds of formula XXXVIII are converted into their corresponding alkyl bromides of formula XL, using methods well known to someone skilled in the art, e.g. functional group interconversion of alcohols into bromides. The reaction is typically carried out in solvents like MeCN, THF, dioxane, DCM and mixtures thereof, at temperatures between 0° C. and 100° C. Typically used brominating reagents are trimethylsilyl chloride in conjunction with lithium bromide, trimethylsilyl bromide, phosphorous tribromide or carbon tetrabromide/triphenylphosphine.

In step 5, scheme 12 the obtained compounds of formula XL are converted into their corresponding ethers of formula XXXIX, using methods well known to someone skilled in the art, e.g. alkylation of alcohols. The reaction is typically carried out in solvents like DMF, THF, NMP, MeCN, acetone, DCM and DCE, at temperatures between 0° C. and 100° C. Typically used bases are potassium carbonate, sodium hydride, lithium hexamethyldisilazide, sodium hexamethyldisilazide and potassium hexamethyldisilazide in conjunction with nucleophiles such as alcohols.

In step 6, scheme 12 the obtained compounds of formula XXXIX are converted into their corresponding amino pyrazoles of formula I-k, using methods well known to someone skilled in the art, e.g. palladium-mediated amination of iminobromides, vinylbromides or aryl bromides as described in step 7a of scheme 1.

Alternatively to the routes described in scheme 11 and scheme 12, the compounds of formula I-k can be prepared via the N,N'-diprotected intermediate of formula XLV shown in scheme 14.

A preferred method for the synthesis of the derivatives of formula I, wherein one of $R^1$ to $R^4$ is heterocyclyl-$T^2$, wherein the heterocyclyl contains at least one nitrogen and wherein the heterocyclyl is attached via the nitrogen, and $T^2$ is an alkylene, one of $R^1$ to $R^4$ is R''', with R''' being defined as $R^1$ to $R^4$ above for formula I, and the remaining two of $R^1$ to $R^4$ are hydrogen, $R^6$ is hydrogen and $R^7$ is methyl, is described in scheme 13. The derivatives of formula (I), wherein one of $R^1$ to $R^4$ is heterocyclyl-$T^2$, wherein the heterocyclyl contains at least one nitrogen and wherein the heterocyclyl is attached via the nitrogen, and $T^2$ is an alkylene, one of $R^1$ to $R^4$ is R''', with R''' being defined as $R^1$ to $R^4$ above for formula I, and the remaining two of $R^1$ to $R^4$ are hydrogen, $R^6$ is hydrogen and $R^7$ is methyl, are named I-l in scheme 13.

Scheme 13

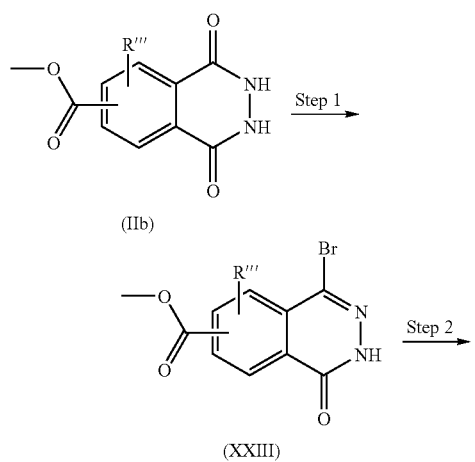
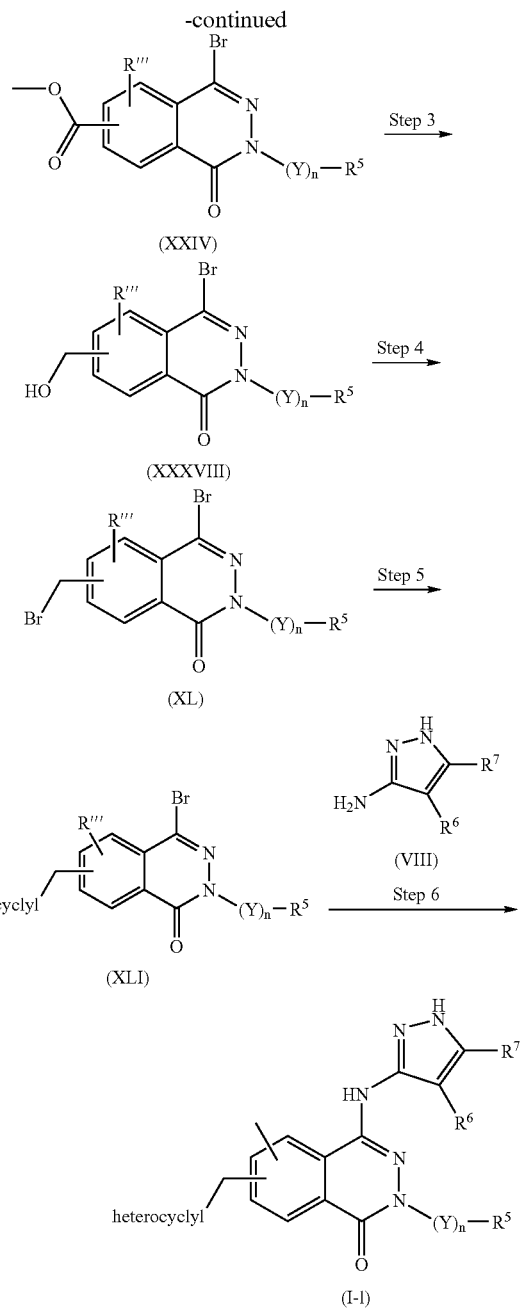

A preferred method for the synthesis of the compounds of formula I-l starts from the corresponding phthalazine diones of formula II-b. Step 1 of the reaction sequence (scheme 13) is a two step process in which a dibromination is followed by a monohydrolysis, yielding the 4-bromo-alkylcarboxyphthalazinone derivatives of formula XXIII as described in step 1 of scheme 1.

In step 2, scheme 13 the obtained compounds of formula XXIII are converted into their corresponding tertiary amides of formula XXIV, using methods well known to someone skilled in the art, e.g. alkylation under basic conditions as described in step 2 of scheme 1.

In step 3, scheme 13 the compounds of formula XXIV are converted into their corresponding alcohols of formula XXX- VIII, using methods well known to someone skilled in the art, e.g. reduction of esters to form alcohols as described in step 3 of scheme 11.

In step 4, scheme 13 the obtained compounds of formula XXXVIII are converted into their corresponding alkyl bromides of formula XL, using methods well known to someone skilled in the art, e.g. functional group interconversion of alcohols into bromides as described in step 4 of scheme 12.

In step 5, scheme 13 the obtained compounds of formula XL are converted into their corresponding heterocyclyl alkyl derivatives of formula XLI, using methods well known to someone skilled in the art, e.g. N-alkylation of nitrogen containing heterocycles. The reaction is typically carried out in solvents like DMF, THF, NMP, MeCN, acetone, DCM and DCE, at temperatures between 0° C. and 100° C. Typically used bases are potassium carbonate, sodium hydride, lithium hexamethyldisilazide, sodium hexamethyldisilazide and potassium hexamethyldisilazide in conjunction with nucleophiles such as secondary amines.

In step 6, scheme 13 the obtained compounds of formula XLI are converted into their corresponding amino pyrazoles of formula I-l, using methods well known to someone skilled in the art, e.g. palladium-mediated amination of iminobromides, vinylbromides or aryl bromides as described in step 7a of scheme 1.

A preferred method for the synthesis of the derivatives of formula I, wherein one of $R^1$ to $R^4$ is $R^8$—$X^{III}$—, with $X^{III}$ being —NHC(O)—, —N(alkyl)C(O)— or —OC(O)—, one of $R^1$ to $R^4$ is R''', with R''' being defined as $R^1$ to $R^4$ above for formula I, and the remaining two of $R^1$ to $R^4$ are hydrogen, $R^6$ is hydrogen and $R^7$ is methyl, is described in scheme 14. The derivatives of formula I, wherein one of $R^1$ to $R^4$ is $R^8$—$X^{III}$—, with $X^{III}$ being —NHC(O)—, —N(alkyl)C(O)— or —OC(O)—, one of $R^1$ to $R^4$ is R''', with R''' being defined as $R^1$ to $R^4$ above for formula I and the remaining two of $R^1$ to $R^4$ are hydrogen, are named I-m in scheme 14.

Scheme 14
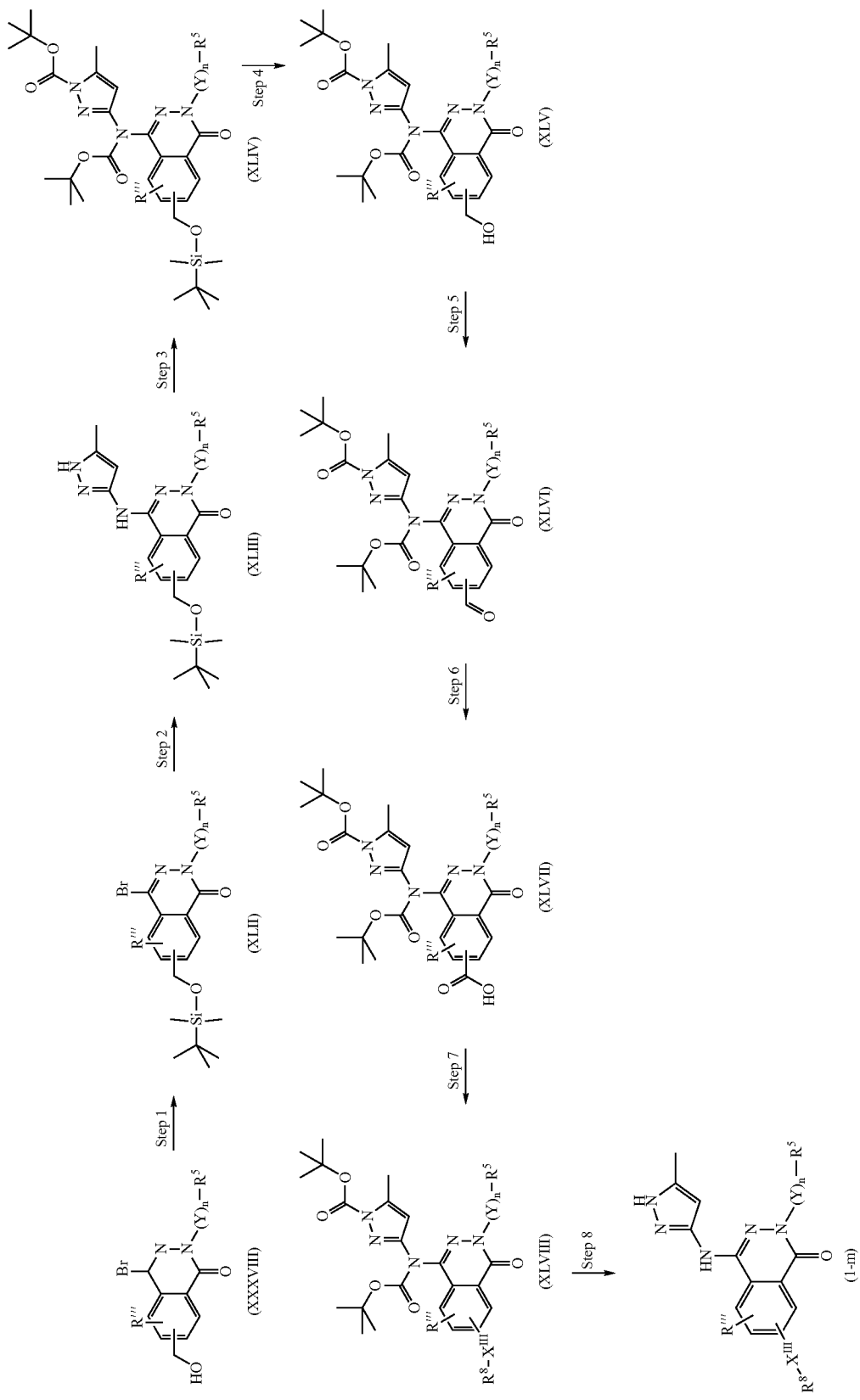

A preferred method for the synthesis of the compounds of formula I-m starts from the corresponding hydroxymethyl bromophthalazinones of formula XXXVIII (for preparation see schemes 11 and 12). In step 1, scheme 14 the obtained compounds of formula XXXVIII are converted into their corresponding silyl ethers of formula XLII, using methods well known to someone skilled in the art, e.g. silyl protection of an alcohol. The reaction is typically carried out in aprotic solvents such as DCM, THF, DMF, DMSO, NMP and mixtures thereof at temperatures between 0° C. and 40° C. Typically used reagents are silyl chlorides or silyl triflates such as tert-butyldimethylsilyl chloride and tert-butyldimethylsilyl triflates. Typically used bases are imidazole, TEA, pyridine and DMAP.

In step 2, scheme 14 the obtained compounds of formula XLII are converted into their corresponding amino pyrazoles of formula XLIII, using methods well known to someone skilled in the art, e.g. palladium-mediated amination of iminobromides, vinylbromides or aryl bromides as described reaction 7a of scheme 1.

In step 3, scheme 14 the obtained compounds of formula XLIII are converted into their corresponding protected amino pyrazoles of formula XLIV, using methods well known to someone skilled in the art, e.g. carbamate protection of amines. The reaction is typically carried out in solvents such as THF, dioxane, DCM, DMF or NMP. Typically used bases are TEA, sodium hydride, DMAP, at temperatures between 0° C. and 100° C. in conjunction with reagents such as di-tert-butyl dicarbonate.

In step 4, scheme 14 the obtained compounds of formula XLIV are converted into their corresponding alcohols of formula XLV, using methods well known to someone skilled in the art, e.g. fluoride mediated deprotection of silyl ethers. The reaction is typically carried out in solvents such as THF, dioxane, and DCM at temperatures between 0° C. and 100° C. Typically used reagents are tetrabutylammonium fluoride, potassium fluoride, hydrogen fluoride-pyridine complex and silica supported tetrabutylammonium fluoride.

In step 5, scheme 14 the obtained compounds of formula XLV are converted into their corresponding aldehydes of formula XLVI, using methods well known to someone skilled in the art, e.g. oxidation of an alcohol. The reaction is typically carried out in solvents such as DMF, NMP, DMSO, THF, dioxane and DCM at temperatures between 0° C. and 100° C. Typically used reagents are pyridine-sulfur trioxide complex, Dess-Martin periodinane (DMP) or 2-iodoxybenzoic acid (IBX).

In step 6, scheme 14 the obtained compounds of formula XLVI are converted into their corresponding carboxylic acids of formula XLVII, using methods well known to someone skilled in the art, e.g. oxidation of carboxaldehyde. The reaction is typically carried out in solvents such as DCM, THF, water and mixtures thereof at temperatures between 0° C. and 40° C. Typically used reagents are sodium chlorite, using buffering reagents such as sulfamic acid and phosphoric acid and radical trapping reagents such as isobutene.

In step 7, scheme 14 the obtained compounds of formula XLVII are converted into their corresponding carboxamides of formula XLVIII, using methods well known to someone skilled in the art, e.g. amide formation by acid-amine coupling as described in step 2 of scheme 3.

In step 8, scheme 14 the obtained compounds of formula XLVIII are converted into compounds of formula I-m, using methods well known to someone skilled in the art, e.g. acid-mediated deprotection of carbamates as described for step 7 of scheme 7.

A preferred method for the synthesis of the derivatives of formula I, wherein n is 1 and Y is -alkylene-C(O)— or -alkylene-CH(OH)—, is described in scheme 15. The derivatives of formula I, wherein n is 1 and Y is -alkylene-C(O)— are named I-n and the derivatives of formula I, wherein n is 1 and Y is -alkylene-CH(OH)— are named I-o in scheme 15.

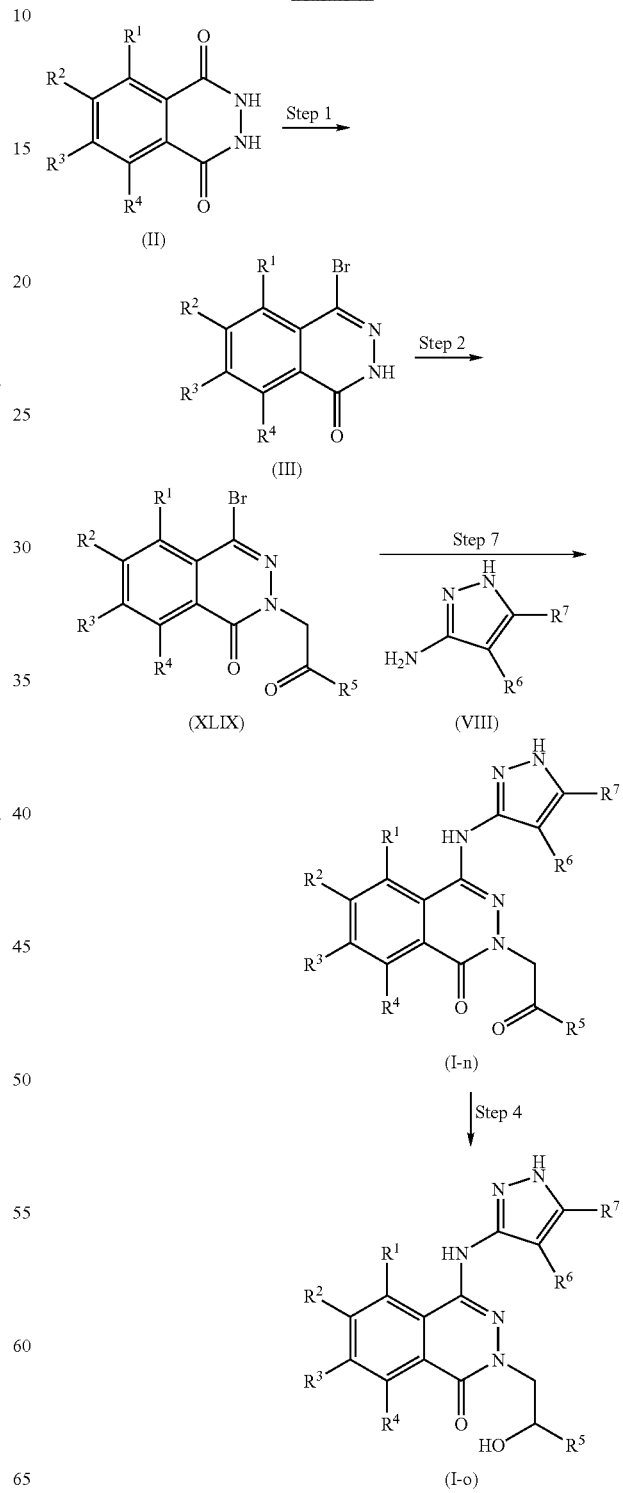

A preferred method for the synthesis of the compounds of formula I-n and I-o starts from the corresponding phthalazine diones of formula II. Step 1 of the reaction sequence (scheme 15) is a two step process in which a dibromination is followed by a monohydrolysis, yielding the 4-bromophthalazinone derivatives of formula III as described in step 1 of scheme 1.

In step 2, scheme 15 the obtained compounds of formula III are converted into their corresponding tertiary amides of formula XLIX, using methods well known to someone skilled in the art, e.g. alkylation under basic conditions with an α-halocarbonyl compound as described for step 2 of scheme 1.

In step 3, scheme 14 the obtained compounds of formula XLIX are converted into their corresponding amino pyrazoles of formula I-n, using methods well known to someone skilled in the art, e.g. palladium-mediated amination of iminobromides, vinylbromides or aryl bromides as described or step 7a of scheme 1.

In step 4, scheme 15 the obtained compounds of formula I-n are converted into their corresponding alcohols of formula I-o, using methods well known to someone skilled in the art, e.g. reduction of ketones to form alcohols. The reaction is typically carried out in solvents like THF, dioxane, DCM and mixtures thereof, at temperatures between 0° C. and 100° C. Typically used reducing reagents are lithium borohydride and other reducing agents.

A preferred method for the synthesis of the derivatives of formula I, wherein $R^5$ is phenyl which is substituted at the para- or meta- position with or —N(alkyl)-R' and R' is —C(O)-aryl, —C(O)-cycloalkyl, —C(O)-alkyl, —C(O)-alkoxyalkyl, —C(O)-alkoxy, —S(O)$_2$-aryl, —S(O)$_2$-alkyl, is described in scheme 16. The derivatives of formula I, wherein $R^5$ is phenyl which is substituted at the para- or meta- position with or —N(alkyl)-R' and R' is —C(O)-aryl, —C(O)-cycloalkyl, —C(O)-alkyl, —C(O)-alkoxyalkyl, —C(O)-alkoxy, —S(O)$_2$-aryl, —S(O)$_2$-alkyl, are named I-p in scheme 16.

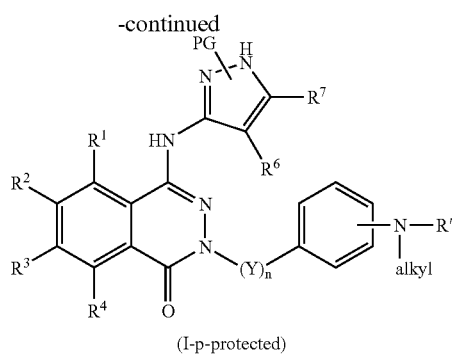

(I-p-protected)

Step 3

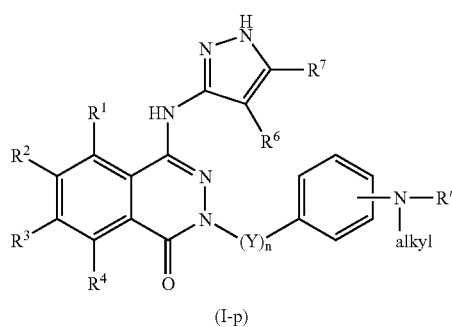

(I-p)

Scheme 16

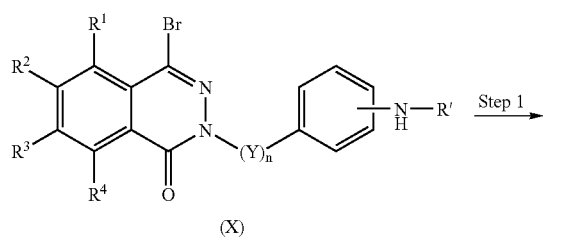

(X)

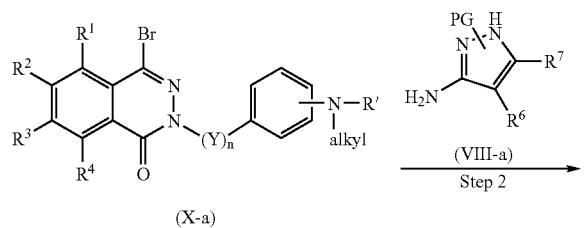

(X-a)

Step 1, scheme 16, is the alkylation of compounds of formula X (see scheme 2) by standard methods known to those skilled in the art, e.g. by alkylation with an alkyl bromide or iodide or tosylate or mesylate, in the presence of a base like sodium hydride, potassium tert.-butoxide, or DIPEA to yield the compounds of formula X-a. Suitable inert solvents are for instance DMF, DMSO, NMP or THF, and the reaction is carried out in a temperature range from −20° C. to 100° C.

Step 2, scheme 16, is the Buchwald coupling (step 7a of scheme 1) of the bromo-phthalazinones of formula X-a with a protected aminopyrazole of formula VIII-a as described in scheme 1, step 7b yielding the protected phthalazinone-aminopyrazole derivatives of formula I-p-protected Step 3, scheme 16, is the cleavage of the protecting group as described in scheme 1, step 8.

Certain derivatives of formula I wherein $R^5$ is phenyl which is substituted at the para- or meta- position with a substituent R'''', R'''' being an aryl group or a nitrogen containing heterocyclyl attached via N, a NH-alkyl, a NH-aryl or an alkylsulfanyl or an arylsulfanyl group, are preferably synthesized according to scheme 17. Such derivatives of formula I are named I-q in scheme 17.

Scheme 17

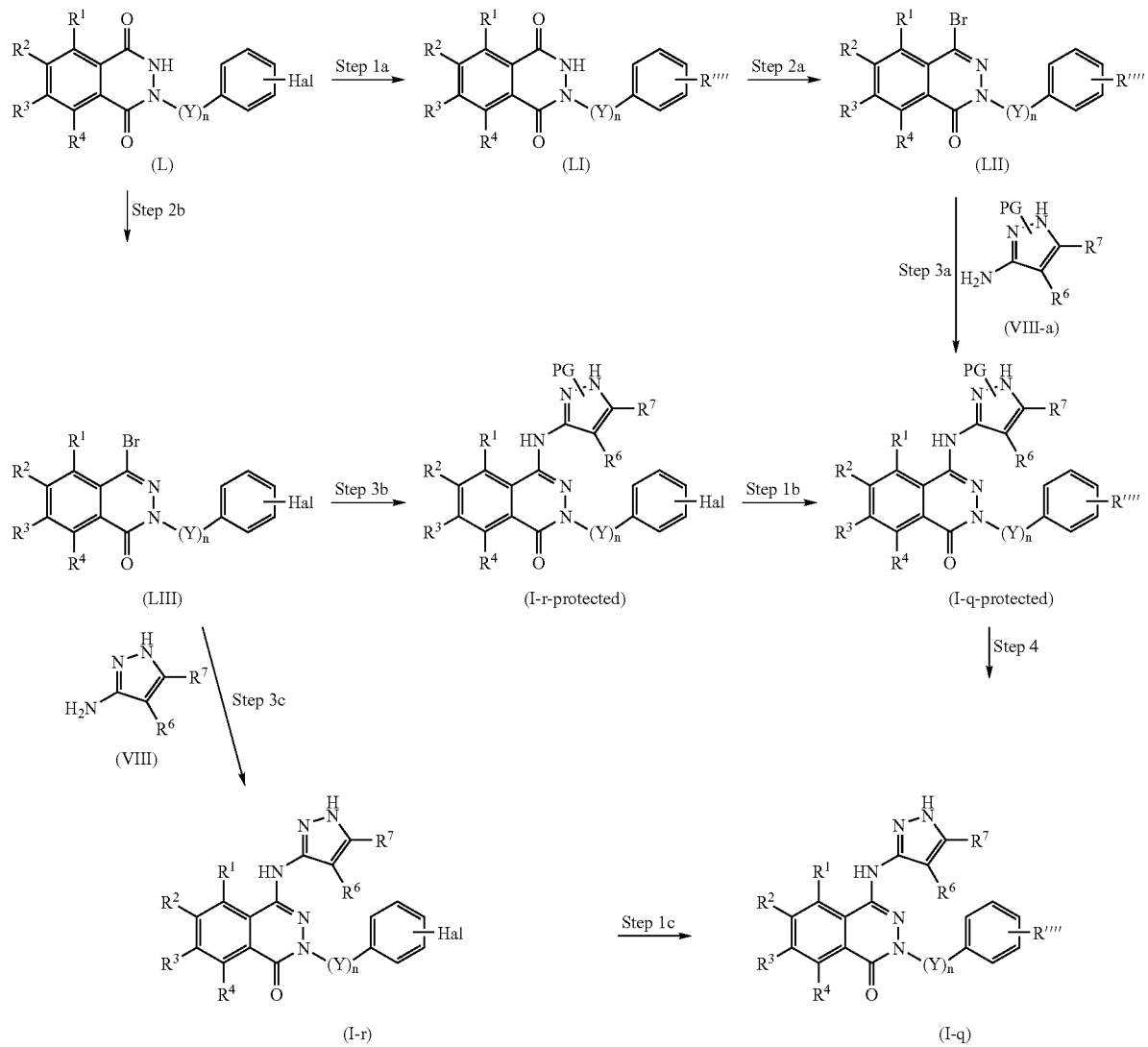

In step 1a, scheme 17, halogen-substituted phthalazinones L, with Hal being iodo or bromo or chloro or fluoro, are converted to compounds of formula LI by a substitution reaction of the aromatic halogen by a group R''''. This can be carried out directly under basic conditions, if the group R'''' comprises a strong nucleophile and the halogen is a fluorine. More preferably, Hal is iodo, bromo or chloro and R'''' is introduced under transition metal catalysis by methods known to the skilled chemist. Typical reactions for this purpose are the Buchwald reaction if R''' is a nitrogen containing heterocyclyl attached via N, a NH-alkyl, a NH-aryl, or an alkylsulfanyl or an arylsulfanyl group. The conditions for such a Buchwald reaction are the same as described for scheme 1, step 7a. If R'''' is an alkylsulfanyl or an arylsulfanyl group, the substitution reaction can also be carried out under Ullman conditions, e.g. in the presence of a Cu catalyst like copper iodide or copper powder in solvents like quinoline, NMP or ethylene glycol, optionally in the presence of e a base like pyridine. The Ullman reaction is carried out at elevated temperatures from 60° C. to 200° C. If R'''' is an aryl group, it is introduced best under the conditions of a Suzuki coupling. In a Suzuki coupling, a boronic acid derivative of R'''' is reacted with L under palladium catalysis by palladium black or a palladium phosphine complex like tetrakis-tri-phenylphosphino-palladium(0), in the presence of a base like sodium carbonate or potassium fluoride. Suitable solvents are toluene, water, dioxane, THF, MeOH, EtOH, or mixtures thereof, and the Suzuki coupling is run at temperatures from RT to 150° C.

Step 2a, scheme 17 is the bromination of a phthalazinedione derivative of formula LI to give a 4-bromophthalazinone derivative of formula LII. The same conditions apply as described for scheme 1, step 6.

Step 3a, scheme 17, is the Buchwald coupling of a bromophthalazinone derivative LII with a protected aminopyrazole VIII-a to give the final products in protected form, I-q-protected. The same methods and conditions apply as described for scheme 1, step 7b.

Step 4, scheme 17, is the deprotection of derivatives I-q-protected to give the final aminopyrazole derivatives I-q. The same conditions apply as described for scheme 1, step 8.

Step 1b, scheme 17, is the substitution reaction of the halogen atom in a protected aminopyrazole derivative of formula I-r-protected. It is carried out with the same methods and conditions as described for step 1a.

Step 2b, scheme 17, is the bromination of phtalazinedione L to give LIII and is carried out as described for scheme 1, step 6.

Step 3b, scheme 17, is the Buchwald coupling of a bromophthalazinone derivative LIII with a protected aminopyrazole VIII-a to give the aminopyrazole derivatives I-r-protected, in protected form. The same methods and conditions apply as described for scheme 1, step 7b. For this step it is preferred that Hal is chloro in order to achieve a selective replacement of only the bromo atom in LIII during the Buchwald reaction.

Step 1c, scheme 17, is the substitution reaction of the halogen atom in an unprotected aminopyrazole derivative of formula I-r. It is carried out with the same methods and conditions as described for step 1a.

Step 3c, scheme 17, is the Buchwald coupling of a bromophthalazinone derivative LIII with a aminopyrazole VIII to give the aminopyrazole derivatives I-r. The same methods and conditions apply as described for scheme 1, step 7a. For this step it is preferred that Hal is chloro in order to achieve a selective replacement of only the bromo atom in LIII during the Buchwald reaction.

If the substituent R"" is alkylsulfanyl and arylsulfanyl group, these sulfanyl groups can subsequently be oxidized to substituents —S(O)alkyl, —SO$_2$alkyl and —S(O)aryl, —SO$_2$aryl by well known reagents like meta-chloroperbenzoic acid (MCPBA) or Oxone. Such an oxidation step can optionally be carried out at a later stage of the sequence, e.g. after step 2a or after step 3a or after step 1b.

Another method for the synthesis of the derivatives of formula I, wherein one of $R^1$ to $R^4$ is NH$_2$ or NO$_2$ or $R^8$—$X^{II}$—, with $X^{II}$ being —C(O)NH—, —NHC(O)NH— or —S(O)$_2$NH—, one of $R^1$ to $R^4$ is R''', with R''' being defined as $R^1$ to $R^4$ above for formula I and the remaining two of $R^1$ to $R^4$ are hydrogen, is described in scheme 18. The derivatives of formula I, wherein one of $R^1$ to $R^4$ is $R^8$—$X^{II}$—, with $X^{II}$ being —C(O)NH—, —NHC(O)NH— or —S(O)$_2$NH—, one of $R^1$ to $R^4$ is R''', with R''' being defined as $R^1$ to $R^4$ above for formula I and the remaining two of $R^1$ to $R^4$ are hydrogen, are named I-d in scheme 18. The derivatives of formula I, wherein one of $R^1$ to $R^4$ is NO$_2$, one of $R^1$ to $R^4$ is R''', with R''' being defined as $R^1$ to $R^4$ above for formula I and the remaining two of $R^1$ to $R^4$ are hydrogen, are named I-s in scheme 18. The derivatives of formula I, wherein one of $R^1$ to $R^4$ is NH$_2$, one of $R^1$ to $R^4$ is R''', with R''' being defined as $R^1$ to $R^4$ above for formula I and the remaining two of $R^1$ to $R^4$ are hydrogen, are named I-t in scheme 18.

Scheme 18

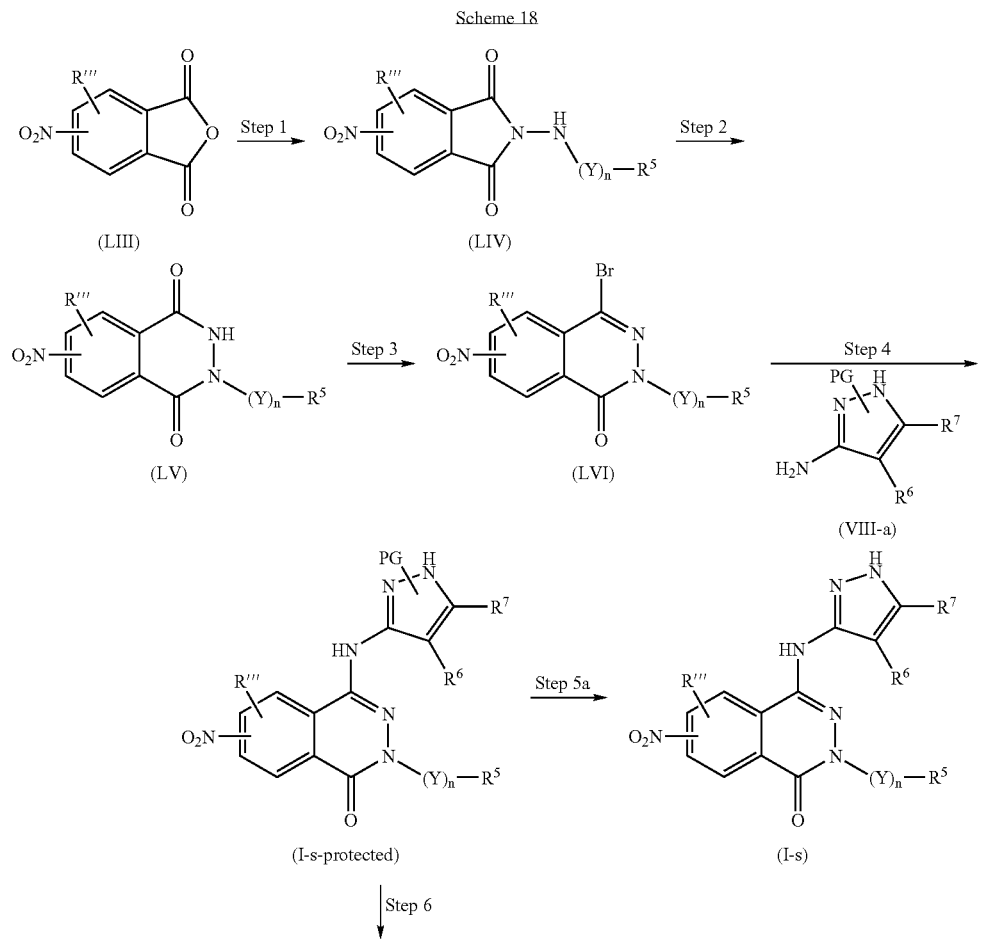

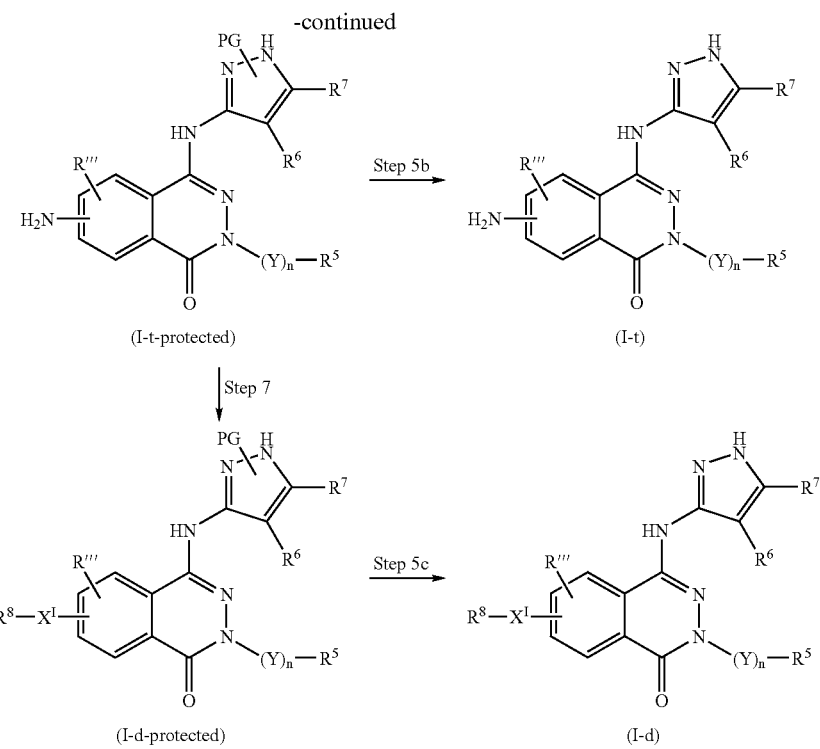

Step 1, scheme 18, is the reaction of a nitro-substituted phthalic anhydride of formula LIII with a substituted hydrazine to give compounds of formula LIV. Step 1 is carried out as described for scheme 1, step 4.

Step 2, scheme 18, is the rearrangement of compounds of formula LIV into phthalazindiones of formula LV and is carried out as described for scheme 1, step 5.

Step 3, scheme 18, is the bromination of phthalazindiones LV to give the 4-bromophthalazinones LVI, and is carried out as described for scheme 1, step 6.

Step 4, scheme 18, is the Buchwald reaction of bromophthalazinones LVI with a protected aminopyrazole derivative VIII-a to yield derivatives of formula I-s-protected and is carried out as described in scheme 1, step 7b.

Step 5a, scheme 18, is the deprotection of derivatives I-s-protected to give the nitro-substituted derivatives I-s and is carried out as described for scheme 1, step 8.

In step 6, scheme 18, the obtained compounds of formula I-s-protected are converted into their corresponding anilines of formula I-t-protected, using methods well known to someone skilled in the art, e.g. aniline formation by the reduction of nitrobenzenes as described for step 1 of scheme 2). Alternatively, the nitro group can be reduced by catalytic hydrogenation with palladium on charcoal as the catalyst in solvents like MeOH or THF, at temperatures between 20° C. and 100° C.

In step 7 scheme 18, the obtained aniline compounds of formula I-t-protected are converted into their corresponding amides, sulfonamides or ureas of formula I-d-protected, using methods well known to someone skilled in the art, e.g. sulfonylation, acylation or aminocarboxylation of anilines as described for step 6 of scheme 2.

Step 5b, scheme 18, is the deprotection of derivatives I-t-protected to give the amino-substituted derivatives I-t and is carried out as described for scheme 1, step 8.

Step 5c, scheme 18, is the deprotection of derivatives I-d-protected to give the substituted derivatives I-d and is carried out as described for scheme 1, step 8.

For a few special cases the different reaction sequences can alternatively involve the step of generating a monochloro derivative of the phthalazinedione instead of the usual monobromo derivative, followed directly or after some intermediary steps by a Buchwald reaction with the appropriate aminopyrazoles (see e.g. Scheme 19)

Another method for the synthesis of the derivatives of formula I, wherein one of $R^1$ to $R^4$ is $NO_2$, the remaining two of $R^1$ to $R^4$ are hydrogen, $R^5$ is hydrogen and n is 0, is described in scheme 19. The derivatives of formula I, wherein one of $R^1$ to $R^4$ is $NO_2$, the remaining two of $R^1$ to $R^4$ are hydrogen, $R^5$ is hydrogen and n is 0, are named I-u in scheme 19.

Scheme 19

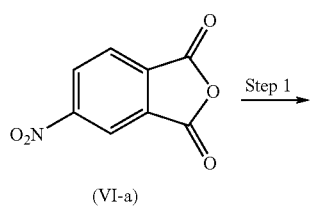

(VI-a)

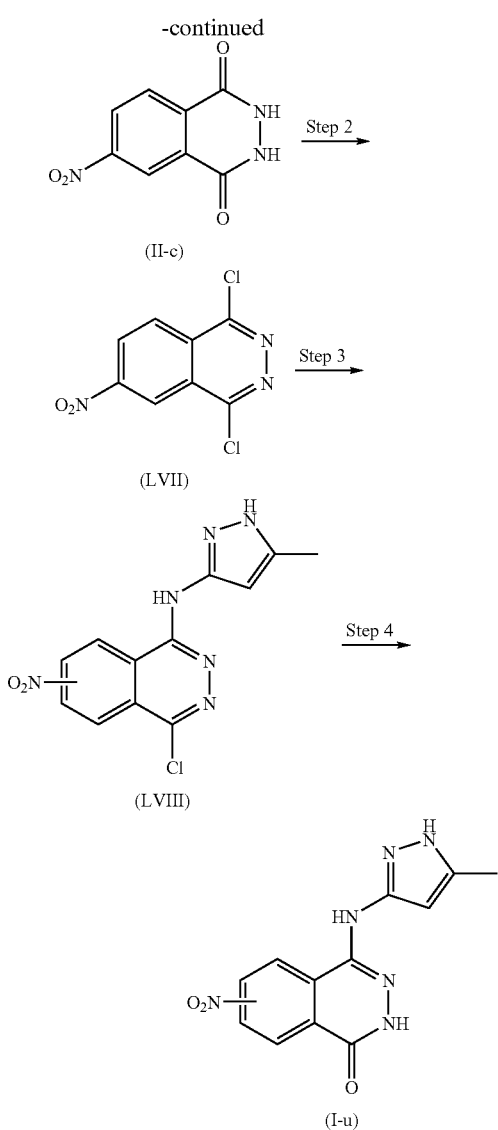

In step 1, scheme 19 the substituted phthalic anhydrides [compounds of formula (VI-a)] are converted into their corresponding Phthalazinones of formula (II-c), using methods well known to someone skilled in the art, e.g. hydrazine mediated ring expansion of phthalic anhydrides. The reaction is typically carried out in aprotic solvents such as THF, DMF, NMP or protic solvents such as HOAc, EtOH, MeOH and IPA and mixtures thereof at temperatures between 0° C. and 120° C. Typically used reagents are hydrazine, hydrazine hydrate and hydrazine hydrochloride. (This method can also be used to obtain phthalazinones of formula I wherein $R^5$ is not hydrogen, when N-substituted hydrazine, hydrazine hydrate and hydrazine hydrochloride instead and the next steps were accordingly).

In step 2, scheme 19 the obtained compounds of formula (II-c) are converted into their corresponding dichlorophthalazines of formula (LVII), using methods well known to someone skilled in the art, e.g. iminochloride formation from secondary amides. The reaction is typically carried out without solvent, or in solvents like DCM, DCE and anisole, and mixtures thereof, at temperatures between 30° C. and 150° C. Typically used chlorinating reagents are $POCl_3$, $PCl_5$ and $PCl_3$, in the presence or absence of bases such as pyridine, TEA and DIPEA.

In step 3, scheme 19 the obtained compounds of formula (LVII) are converted into their corresponding aminopyrazole (LVIII), using methods well known to someone skilled in the art, e.g. aromatic substitution displacements of iminochlorides with amines. The reaction is typically carried out in solvents such as THF, pyridine, toluene, alkanols such as IPA or tert-butanol, and mixtures thereof at temperatures between 40° C. and 150° C.

In step 4, scheme 19 the iminochlorides of formula (LVIII) are converted into their corresponding amide (I-u), using methods well known to someone skilled in the art, e.g. monohydrolyis of the iminochloride. The reaction is typically carried out under aqueous or anhydrous conditions in solvents such as water, aqueous lithium hydroxide, aqueous potassium hydroxide, aqueous sodium carbonate, aqueous potassium hydrogen carbonate, aqueous potassium carbonate, aqueous MeOH, glacial HOAc at temperatures between 20° C. and 110° C.

In the above schemes 1 to 19, certain substituents on the groups $R^1$ to $R^4$ and $R^5$ may not be inert to the conditions of the synthesis sequences described above and may require protection by standard protecting groups known in the art. For instance, an amino or hydroxyl group may be protected as an acetyl or tert.-butoxycarbonyl derivative. Alternatively, some substituents may be derived from others at the end of the reaction sequence. For instance, a compound of formula I may be synthesized bearing a nitro-, an ethoxycarbonyl, a sulfonic acid substituent on the group $R^1$ to $R^4$ and $R^5$, which substituents are finally converted to an amino-, alkylamino-, dialkylamino-, acylamino-, alkylsulfonylamino, arylsulfonylamino substituent, or to a carboxamide substituent, or to a sulfonamide substituent by standard procedures.

The compounds according to the present invention may exist in the form of their pharmaceutically acceptable salts. The term "pharmaceutically acceptable salt" refers to conventional acid-addition salts that retain the biological effectiveness and properties of the compounds of formula I and are formed from suitable non-toxic organic or inorganic bases or from organic or inorganic acids. Examples of base-addition salts include those derived from sodium, potassium, ammonium, quaternary ammonium hydroxides (such as e.g., tetramethylammonium hydroxide). Examples of acid-addition salts include those derived from inorganic acids such as HCl, hydrobromic acid, hydroiodic acid, sulfuric acid, sulfamic acid, phosphoric acid and nitric acid, and those derived from organic acids such as p-toluenesulfonic acid, naphthalenesulfonic acid, naphthalenedisulfonic acid, methanesulfonic acid, ethanesulfonic acid and the like. The chemical modification of a pharmaceutical compound (i.e. a drug) into a salt is a technique well known to pharmaceutical chemists to obtain improved physical and chemical stability, hygroscopicity, flowability and solubility of compounds. See, e.g. Stahl and Wermuth (editors), Handbook of Pharmaceutical Salts, Verlag Helvetica Chimica Acta (VHCA), Züirich, (2002) or Bastin et al., Organic Proc. Res. Dev. 4 (2000) 427-435.

The compounds of formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively separation of the enantiomers can also be achieved by using chromatography on chiral HPLC-phases which are commercially available.

Pharmacological Activity

The compounds of formula I and their pharmaceutically acceptable salts possess valuable pharmacological properties. It has been found that said compounds show activity as inhibitors of BTK and SYK and also show anti-B-cell activation activity. Consequently the compounds of the present invention are useful in the therapy and/or prevention of illnesses with known activation or over-expresssion of BTK and/or SYK, especially in the therapy and/or prevention of illnesses mentioned above. The activity of the present compounds as inhibitors of BTK and/or SYK is demonstrated by the following biological assays.

Determination of $IC_{50}$ of Bruton's Tyrosine Kinase (Btk) Inhibition

The assay is a capture of radioactive $^{33}P$ phosphorylated product through filtration. The interactions of Btk, biotinylated $SH_2$ peptide substrate (Src homology), and ATP lead to phosphorylation of the peptide substrate. Biotinylated product is bound streptavidin sepharose beads. All bound, radiolabeled products are detected by scintillation counter.

Plates assayed are 96-well polypropylene (Greiner) and 96-well 1.2 μm hydrophilic PVDF filter plates (Millipore). Concentrations reported here are final assay concentrations: 10-100 μM compounds in DMSO (Burdick and Jackson), 5-10 nM Btk enzyme (His-tagged, full-length), 30 μM peptide substrate (Biotin-Aca-AAAEEIYGEI-$NH_2$), 100 μM ATP (Sigma), 8 mM imidazole (Sigma, pH 7.2), 8 mM glycerol-2-phosphate (Sigma), 200 μM EGTA (Roche Diagnostics), 1 mM $MnCl_2$ (Sigma), 20 mM $MgCl_2$ (Sigma), 0.1 mg/ml BSA (Sigma), 2 mM DTT (Sigma), 1 μCi $^{33}P$ ATP (Amersham), 20% streptavidin sepharose beads (Amersham), 50 mM EDTA (Gibco), 2 M NaCl (Gibco), 2 M NaCl w/1% phosphoric acid (Gibco), microscint-20 (Perkin Elmer).

$IC_{50}$ determinations are calculated from 10 data points per compound utilizing data produced from a standard 96-well plate assay template. One control compound and seven unknown inhibitors were tested on each plate and each plate was run twice. Typically, compounds were diluted in half-log starting at 100 μM and ending at 3 nM. The control compound was staurosporine. Background was counted in the absence of peptide substrate. Total activity was determined in the presence of peptide substrate. The following protocol was used to determine BTK inhibition.

1) Sample preparation: The test compounds were diluted at half-log increments in assay buffer (imidazole, glycerol-2-phosphate, EGTA, $MnCl_2$, $MgCl_2$, BSA).

2) Bead preparation
   a.) rinse beads by centrifuging at 500 g
   b.) reconstitute the beads with PBS and EDTA to produce a 20% bead slurry 3) Pre-incubate reaction mix without substrate (assay buffer, DTT, ATP, $^{33}P$ ATP) and mix with substrate (assay buffer, DTT, ATP, $^{33}P$ ATP, peptide substrate) 30° C. for 15 min.

4) To start assay, pre-incubate 10 μL BTK in enzyme buffer (imidazole, glycerol-2-phosphate, BSA) and 10 μL of test compounds for 10 min at RT.

5) Add 30 μL reaction mixture without or with substrate to BTK and compounds.

6) Incubate 50 μL total assay mix for 30 min at 30° C.

7) Transfer 40 μL of assay to 150 μL bead slurry in filter plate to stop reaction.

8) Wash filter plate after 30 min, with following steps
   a. 3 ×250 μL NaCl
   b. 3×250 μL NaCl containing 1% phosphoric acid
   c. 1×250 μL $H_2O$ 9) Dry plate for 1 h at 65° C. or overnight at RT 10) Add 50 μL microscint-20 and count $^{33}P$ cpm on scintillation counter.

Calculate percent activity from raw data in cpm percent activity=(sample−bkg)/(total activity−bkg)× 100

Calculate $IC_{50}$ from percent activity, using one-site dose response sigmoidal model $$y=A+((B-A)/(1+((x/C)^D)))$$

x=cmpd conc, y=% activity, A=min, B=max, C=$IC_{50}$, D=1 (hill slope)

With compounds, of the present invention, the $IC_{50}$ for inhibition of BTK was detected in the range of 0.14-0.88 μM (13 compounds) and 1.1-65 μM (45 compounds). Representative results are in Table 1.

Determination of $IC_{50}$ of Spleen Tyrosine Kinase (SYK) Inhibition

The SYK kinase assay is a standard kinase assay adapted to a 96 well plate format. This assay is performed in 96-well format for $IC_{50}$ determination with 8 samples which represented 10 half log dilutions and a 40 μL reaction volume. The assay measures the incorporation of radiolabeled $^{33}P$ γATP into an N-terminally biotinylated peptide substrate, derived from naturally occurring phosphoacceptor consensus sequence (Biotin-11aa DY*E). Phosphorylated products were detected upon termination of reactions with EDTA and the addition of Streptavidin coated beads.

Assay plates: 96-well MultiScreen 0.65 um filter plates (Millipore Cat. No.: MADVNOB10)

Streptavidin coated beads: Streptavidin Sepharose TM, suspension 5.0 mL, in 50 mM EDTA/PBS diluted (1:100), (Amersham, Cat. No.: 17-5113-01)

Compounds: 10 mM in 100% dimethylsulfoxide (DMSO), final conc.: compound 0.003-100 uM in 10% DMSO Enzyme: SYK RPA purified, truncated construct of Spleen Tyrosine Kinase aa 360-635, stock solution 1 mg/mL, MW: 31.2 KDa, final conc.:0.0005 μM.

Peptide 1: biotinylated peptide is derived from a naturally occurring phosphor-acceptor consensus sequence (Biotin-EPEGDYEEVLE), special order from QCB, stock solution 20 mM, final conc.: 5.0 μM.

ATP: Adenosine-5'-triphosphate 20 mM, (ROCHE Cat. No.: 93202720), final concentration: 20 μM Buffer: HEPES: 2-Hydroxyethyl piperazine-2-ethanesulfonic acid (Sigma, Cat. No.: H-3375) final concentration: 50 mM HEPES pH7.5

BSA: Bovine Serum Albumin Fraction V, fatty acid free (Roche Diagnostics GmbH, Cat. No. 9100221) diluted to a final concentration of 0.1%

EDTA: EDTA stock solution 500 mM, (GIBCO, Cat. No.: 15575-038) final concentration: 0.1 mM DTT: 1,4-Dithiothreitol (Roche Diagnostics GmbH, Cat. No.: 197777), final conc.: 1 mM $MgCl_2$×6$H_2O$: MERCK, Cat. No.: 105833.1000, final concentration: 10 mM Assay Dilution Buffer (ADB): 50 mM HEPES, 0.1 mM EGTA, 0.1 mM Na Vanadate, 0.1 mM β-glycerophosphate, 10 mM $MgCl_2$, 1 mM DTT, 0,1% BSA, pH 7.5

Bead wash buffer: 10 g/L PBS (Phosphate buffered saline) with 2M NaCl+1% phosphoric acid Experimental Method:

In 40 µL volume, 26 µL of ADB diluted, purified recombinant human SYK360-635 [0.5 nM] was mixed with 4 µL of 10× concentrations of the test compounds, [usually 100 µM-0.003 µM] in [10%] DMSO and the mixture was incubated for 10 min at RT.

The kinase reaction was initiated by the addition of 10 µL 4× substrate cocktail containing the DYE peptide substrate [0 or 5 µM], ATP [20 µM] and $^{33}$PβATP [2 µCi/rxn]. After incubation at 30° C. for 15 min, the reaction was terminated by the transfer of 25 µL of the reaction sample to a 96 well 0.65 um Millipore MADVNOB membrane/plate containing 200 µL 5 mM EDTA and 20% Streptavidine coated beads in PBS.

The unbound radionucleotides were washed under vacuum with 3×250 µL 2M NaCl; 2×250 µL 2M NaCl+1% phosphoric acid; 1×250 µL H$_2$O. After the last wash membrane/plates were transferred to an adaptor plate, heat dried for 15 min at 60° C., and 50 µL scintillation cocktail was added to each well and 4 h later the amount of radioactivity was counted in a top counter.

The percent inhibition was calculated based on the uninhibited enzyme rate:

% Inhibition=$100/(1+(IC_{50}/\text{Inhibitor conc})^n)$

The IC$_{50}$ was calculated using a non-linear curve fit with XLfit software (ID Business Solution Ltd., Guilford, Surrey, UK). With claimed compounds, the IC$_{50}$ for inhibition of SYK was detected in the range of 0.04-0.96 µM (11 compounds) and 1.2-87 µM (38 compounds). Representative results are in Table 1.

Inhibition of B-cell Activation—B Cell FLIPR Assay in Ramos Cells

Inhibition of B-cell activation by compounds of the present invention was demonstrated by determining the effect of the test compounds on anti-IgM stimulated B cell responses.

The B cell FLIPR assay is a cell based functional method of determining the effect of potential inhibitors of the intracellular calcium increase from stimulation by an anti-IgM antibody. Ramos cells (human Burkitt's lymphoma cell line. ATCC-No. CRL-1596) were cultivated in Growth Media (described below). One day prior to assay, Ramos cells were resuspended in fresh growth media (same as above) and set at a concentration of 0.5×10$^6$/mL in tissue culture flasks. On day of assay, cells were counted and set at a concentration of 1×10$^6$/mL in growth media supplemented with 1 µM FLUO-3 AM(TefLabs Cat-No. 0116, prepared in anhydrous DMSO and 10% Pluronic acid) in a tissue culture flask, and incubated at 37° C. (4% CO$_2$) for 1 h. To remove extracellular dye, cells were collected by centrifugation (5 min, 1000 rpm), resuspended in FLIPR buffer (described below) at 1×10$^6$ cells/mL and then dispensed into 96-well poly-D-lysine coated black/clear plates (BD Cat-No. 356692) at 1×10$^5$ cells per well. Test compounds at seven concentrations ranging from 100 µM to 0.03 µM were added, and allowed to incubate with cells for 30 min at RT. Ramos cell Ca$^{2+}$ signaling was stimulated by the addition of 10 µg/mL anti-IgM (Southern Biotech, Cat-No. 2020-01) and measured on a FLIPR (Molecular Devices, captures images of 96 well plates using a CCD camera with an argon laser at 480 nM excitation).

Growth Medium: RPMI 1640 medium with L-glutamine (Invitrogen, Cat-No. 61870-010), 10% Fetal Bovine Serum (FBS, Summit Biotechnology Cat-No. FP-100-05); 1 mM Sodium Pyruvate (Invitrogen Cat. No. 11360-070).

FLIPR buffer: HBSS (Invitrogen, Cat-No. 141175-079),2 mM CaCl$_2$ (Sigma Cat-No. C-4901), HEPES (Invitrogen, Cat-No. 15630-080), 2.5 mM Probenecid (Sigma, Cat-No. P-8761), 0.1% BSA (Sigma, Cat-No. A-7906), 11 mM Glucose (Sigma, Cat-No. G-7528).

In order to achieve the highest final assay concentration of 100 µM, 24 µL of 10 mM compound stock solution (made in DMSO) is added directly to 576 µL of FLIPR buffer. The test compounds are diluted in FLIPR Buffer (using Biomek 2000 robotic pipettor) resulting in the following dilution scheme: vehicle, 1.00×10$^{-4}$ M, 1.00×10$^{-5}$, 3.16×10$^{-6}$, 1.00×10$^{-6}$, 3.16×10$^{-7}$, 1.00×10$^{-7}$, 3.16×10$^{-8}$.

Intracellular increases in calcium were reported using a max-min statistic (subtracting the resting baseline from the peak caused by addition of the stimulatory antibody using a Molecular Devices FLIPR control and statistic exporting software. The IC$_{50}$ was determined using a non-linear curve fit (GraphPad Prism software). Representative results are in Table 1.

Assay Results

TABLE 1

| Compound No. | IC$_{50}$ (µM) BTK Assay | IC$_{50}$ (µM) SYK Assay | IC$_{50}$ (µM) B cell FLIPR |
|---|---|---|---|
| A-1 | 1.248 | | |
| A-3 | 70.474 | | |
| A-4 | 11.424 | | |
| A-5 | 8.223 | 7.68 | |
| A-6 | 38.165 | | |
| A-7 | 6.301 | | |
| A-8 | 29.967 | 0.552 | |
| A-9 | 5.873 | | |
| A-10 | 16.627 | | |
| A-11 | 9.791 | 49.2 | |
| A-13 | 38.648 | 22.9 | |
| A-16 | 25.239 | 87.9 | |
| A-18 | | 6.53 | |
| A-21 | 14.586 | >10 | |
| A-22 | | 78.1 | |
| A-23 | 50.918 | | |
| A-24 | 1.751 | 24.9 | |
| A-25 | | 0.525 | |
| B-1 | 5.034 | 1.186 | |
| E-1 | >100 | | |
| E-2 | 9.533 | 7.61 | |
| E-3 | 58.162 | 87.5 | |
| E-9 | 10.367 | 7.665 | |
| F-1 | 0.275 | 0.565, 2.31, 0.526 | 1.2 |
| F-2 | 100 | 36.4 | |
| F-5 | 0.102 | 0.37, 0.7, 0.536 | 0.41 |
| F-6 | 0.468 | 4.77, 0.465 | 1.13 |
| F-7 | 14.615 | 37.4 | |
| F-10 | 0.608 | 0.551, 4.295, 3.57 | |
| G-1 | 0.724 | 0.793 | |
| G-6 | 1.278 | 2.52 | |
| H-1 | 4.325 | 1.57 | |
| H-2 | 1.106 | 4.29 | |
| I-2 | 0.231 | 0.392 | |
| I-8 | 2.227 | 5.62 | |
| K-1 | | 1.25 | |
| M-5 | 0.769 | 2.16 | |
| M-6 | 67.661 | 9.99 | |
| M-9 | 0.782 | 0.666 | |
| M-10 | | 56.9 | |
| ZD-3 | 0.86 | 3.02 | |
| ZD5 | 0.186 | 1.86 | 0.575 |
| ZI-2 | 0.44 | 0.894 | |

Dosage and Administration

The compounds utilized in the present invention as medicaments may be formulated in a wide variety of oral administration dosage forms and carriers. Oral administration can be in the form of tablets, coated tablets, dragees, hard and soft gelatine capsules, solutions, emulsions, syrups, or suspensions. Compounds utilized herein are efficacious when administered by other routes of administration including continuous (intravenous drip) topical parenteral, intramuscular, intravenous and suppository administration, among other routes of administration. The preferred manner of administration is generally oral using a convenient daily dosing regimen which can be adjusted according to the degree of affliction and the patient's response to the active ingredient.

Compounds useful as medicaments for BTK and SYK-mediated diseases, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds disclosed herein can be administered alone but will generally be administered in admixture with one or more suitable pharmaceutical excipients, diluents or carriers selected with regard to the intended route of administration and standard pharmaceutical practice.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as HCl, hydrobromic acid, sulfuric acid, nitric acid, phosphoric acid, and the like; or formed with organic acids such as HOAc, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxy-ethanesulfonic acid, benzenesulfonic acid, 4-chlorobenzenesulfonic acid, 2-naphthalene-sulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylHOAc, tertiary butyl-HOAc, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as EtOHamine, diEtOHamine, triEtOHamine, tromethamine, N-methylglucamine, and the like. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, e.g., in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, e.g. bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, e.g. solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

Medicaments disclosed herein may be formulated for administration as suppositories. A low melting wax, such as a mixture of fatty acid glycerides or cocoa butter is first melted and the active component is dispersed homogeneously, e.g., by stirring. The molten homogeneous mixture is then poured into convenient sized molds, allowed to cool, and to solidify.

Medicaments disclosed herein may be formulated for vaginal administration. Pessaries, tampons, creams, gels, pastes, foams or sprays containing in addition to the active ingredient such carriers as are known in the art to be appropriate.

When desired, formulations can be prepared with enteric coatings adapted for sustained or controlled release administration of the active ingredient. For example, the medicaments disclosed herein can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a bio-degradable polymer, e.g., polyactic acid.

Suitable formulations along with pharmaceutical carriers, diluents and expcipients are described in *Remington: The Science and Practice of Pharmacy* 1995, edited by Martin, Mack Publishing Company, 19th edition, Easton, Pa. A skilled formulation scientist may modify the formulations within the teachings of the specification to provide numerous formulations for a particular route of administration without rendering the medicaments disclosed herein unstable or compromising their therapeutic activity.

The modification of the medicaments disclosed herein to render them more soluble in water or other vehicle, e.g., may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in mono-therapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

EXAMPLES

Generic Experimental for the Synthesis of Phthalazinone Derivatives:

Method A

Example A-1

4-(5-Methyl-2H-pyrazole-3-ylamino)-phenyl-2H-phthalazin-1-one

2-Phenyl-2,3-dihydro-phthalazine-1,4-dione: Phenyl hydrazine (59.4 g, 0.55 mol) was added in one portion to a stirred mixture of phthalic anhydride (74.0 g, 0.5 mmol), in HOAc (500 ml) at RT. The reaction mixture was heated to 125° C. for 2 hours, and then allowed to cool to RT. The resultant suspension was poured into water (500 ml) and the solid was isolated by filtration. The solid was then stirred in 1M $Na_2CO_3$ (400 ml), and the remaining undissolved solid removed by filtration. This solid was washed with two further 400 ml portions of 1M $Na_2CO_3$.

The basic solutions were combined and acidified by dropwise addition of concentrated HCl until gas evolution ceased. The precipitate formed was isolated by filtration and dried for 18 hours in a vacuum oven (50° C.) to give the phthalazinone as a white solid (46.3 g, 39% yield). $^1$H-NMR: (400 MHz; $D_6$-DMSO); 11.7 (1H, br. s), 8.30 (1H, d), 8.03 (1H, d), 7.93 (2H, m), 7.67 (1H, d), 7.51 (1H, t), 7.4 (1H, t); MS (ESI$^+$)= (M+H)$^+$ 239

4-Bromo-2-phenyl-2H-phthalazin-1-one (Bromination): Phosphorus oxybromide (3.13 g, 10.9 mmol) was added to a stirred suspension of 2-phenyl-2,3-dihydro-phthalazine-1,4-dione (1.30 g, 5.4 mmol) in 1,2 DCE (15.0 ml). The reaction was heated to 100° C. for 18 hours and then cooled and poured into water.

The aqueous layer was made basic with 1M $Na_2CO_3$, then extracted into DCM (3×100 ml). The organic layers were combined, dried ($MgSO_4$) and concentrated under vacuum. The residue was purified by silica column chromatography (20% EtOAc: hexane) to give the bromophthalazinone as a white solid (0.770 g, 2.6 mmol, 48% yield). $^1$H-NMR: (400 MHz; $D_6$-DMSO); 8.20 (1H, dd), 7.91 (1H, td), 7.89 (1H, td), 7.35-7.55 (5H, m); MS (ESI$^+$)=(M+H)$^+$ 301, 303

4-(5-Methyl-2H-pyrazole-3-ylamino)-phenyl-2H-phthalazin-1-one (A-1) (Typical procedure for the Buchwald Reaction): Degassed toluene (6 ml) and EtOH (3 ml) were added in one portion to a mixture of 4-bromo-2-phenyl-2H-phthalazin-1-one (0.750 g, 2.5 mmol), sodium t-butoxide (0.337 g, 3.5 mmol), 3-amino-5-methyl pyrazole (0.291 g, 3 mmol), tris-(dibenzylideneacetone)-dipalladium (0.115 g, 0.125 mmol) and 2-(di-t-butylphosphino)-biphenyl (0.075 g, 0.25 mmol) under nitrogen. The reaction mixture was heated to 100° C. for 20 hours with stirring and then cooled to RT. Diethyl ether (10 ml) was added and the precipitated solid was filtered to give the crude product as a grey solid (0.6 g, 76% yield). A 0.06 g portion of the crude product was triturated with MeCN (2 ml) and water (2 ml) to give the target compound (0.045 g, 58% yield based on recovered materials). $^1$H-NMR: (400 MHz, $D_6$-DMSO) 11.96 (1H, s), 9.33 (1H, s), 8.53 (1H, d), 8.38 (1H, d), 7.92-7.99 (2H, m), 7.88 (2H, d), 7.77 (2H, t) 7.34 (1H, t) 6.24 (1H, s) 2.18 (3H, s) MS (ESI$^+$)=(M+H)$^+$ 318.29.

Using the experimental conditions reported above (Method A) and the appropriate starting materials, the following derivatives were prepared:

| Example No. | Systematic name | ¹H-NMR | MS (ESI+, M + H) |
|---|---|---|---|
| A-2 | 2-benzyl-4-(5-methyl-1H-pyrazol-3-yl-amino)-2H-phthalazin-1-one | (400MHz, $D_6$-DMSO) 11.86(1H, s), 9.25(1H, s), 8.46(1H, d), 8.32(1H, d), 7.84-.7.94(2H, m), 7.25-7.38(5H m), 6.10(1H, s), 5.24(2H, s) 2.17(3H, s) | 332.08 |
| A-3 | 2-methyl-4-(5-methyl-1H-pyrazol-3-yl-amino)-2H-phthalazin-1-one | (400MHz, $D_6$-DMSO) 11.70(1H, s), 9.00(1H, s), 8.23(1H, d), 8.10(1H d), 7.73-7.64(2H, m), 6.13(1H, S), 3.44(3H S), 2.04(3H, s) | 389.27 |
| A-4 | 2-isobutyl-4-(5-methyl-1H-pyrazol-3-ylamino)-2H-phthalazin-1-one | (400MHz, $D_6$-DMSO) 11.76(1H, s), 9.00(1H, s), 8.2(1H, d), 8.15(1H d), 7.77-7.67(2H, m), 6.17(1H, S), 3.71(2H d), 2.10-2.07(4H, m), 0.75(6H, d) | 298.33 |
| A-5 | 4-(5-methyl-1H-pyrazol-3-ylamino)-2-(2,2,2-trifluoro-ethyl)-2H-phthalazin-1-one | (400MHz, $D_6$-DMSO) 9.58(1H, s), 8.47(1H, d), 8.34(1H, d), 8.01-7.83(2H m), 6.34(1H, S), 4.93(2H q), 2.25(3H, s) | 323.10 |
| A-6 | 4-(5-methyl-1H-pyrazol-3-ylamino)-2-p-tolyl-2H-phthalazin-1-one | (400MHz, $D_6$-DMSO) 11.70(1H s), 9.04(1H, s), 8.26(1H, d), 8.11(1H, d), 7.74-7.64(2H m), 7.34(2H, d), 7.05(2H d), 6.01(1H, s), 2.14(3H, s), 1.94(3H, s) | 332.34 |
| A-7 | 2-(4-fluoro-phenyl)-4-(5-methyl-1H-pyrazol-3-ylamino)-2H-phthalazin-1-one | (400MHz, $D_6$-DMSO) 12.17(1H s), 9.51(1H, s), 8.73(1H, d), 8.59(1H, d), 8.20-8.10(2H, m), 7.99-7.95(2H, m), 7.55(2H t), 6.45(1H, s), 2.40(3H, s) | 336.31 |
| A-8 | 2-(4-tert-butyl-phenyl)-4-(5-methyl-1H-pyrazol-3-ylamino)-2H-phthalazin-1-one | (400MHz, $D_6$-DMSO) 9.36(1H, s), 8.46(1H, d), 8.38(1H, d), 8.00-7.89(2H m), 7.62(2H, d), 7.50(2H, d) 6.24(1H, s), 2.21(3H, s), 1.34(9H, s) | 374.40 |
| A-9 | 2-(4-methoxy-phenyl)-4-(5-methyl-1H-pyrazol-3-ylamino)-2H-phthalazin-1-one | (400MHz, $D_6$-DMSO) 11.72(1H, s) 9.05(1H, s), 8.28(1H, d), 8.15(1H, d), 7.76-7.66(2H m), 7.40(2H, d), 6.84(2H, d) 6.03(1H, s), 3.61(3H, s), 1.97(3H, s) | 348.34 |
| A-10 | 4-(1H-pyrazol-3-yl-amino)-2-p-tolyl-2H-phthalazin-1-one | (400MHz, $D_6$-DMSO) 12.05(1H, s) 9.22(1H, s), 8.33(1H, d), 8.15(1H, d), 7.78-7.68(2H m), 7.39-7.37(3H, m), 7.09(2H, d) 6.29(1H, s), 2.16(3H, s) | 318.32 |
| A-11 | 2-(4-methoxy-benzyl)-4-(5-methyl-1H-pyrazol-3-ylamino)-2H-phthalazin-1-one | (400MHz, $D_6$-DMSO) 11.91(1H, s), 9.28(1H, s), 8.47(1H, d), 8.36(1H, d), 7.97-7.89(2H, m), 7.37(2H, d), 6.18(1H, d), 5.21(2H, s), 3.76(3H, s), 2.24(3H, s) | 362.36 |
| A-12 | 2-(3-methoxy-benzyl)-4-(5-methyl-1H-pyrazol-3-ylamino)-2H-phthalazin-1-one | (400MHz, $D_6$-DMSO) 11.88(1H, s), 9.23(1H, s), 8.44(1H, d), 8.32(1H, d), 7.92-7.86(2H, m), 7.24(1H, t), 6.96(1H, d), 6.93(1H, s), 6.84(1H, s), 6.15(1H, s), 5.21(2H, s), 3.72(3H, s), 2.18(3H, s) | 362.35 |
| A-13 | 2-(2,5-difluoro-benzyl)-4-(5-methyl-1H-pyrazol-3-yl-amino)-2H-phthalazin-1-one | (400MHz, $D_6$-DMSO) 11.88(1H, s), 9.25(1H, s), 8.32(1H, d), 7.93-7.85(2H, m), 7.32-7.21(3H, m), 5.93(1H, s), 5.29(2H, s), 2.16(3H, s) | 368.14 |
| A-14 | 2-(4-methanesulfonyl-benzyl)-4-(5-methyl-2H-pyrazol-3-ylamino)-2H-phthalazin-1-one | (400MHz, $D_6$-DMSO) 9.20(1H, s), 8.35(1H, d), 8.25(1H, d), 7.89-7.79(4H, m), 7.53(2H, d), 6.00(1H, s), 5.30(2H, s), 3.08(3H, s), 2.12(3H, s) | 410.12 |
| A-15 | 2-(3,4-difluoro-benzyl)-4-(5-methyl-1H-pyrazol-3-yl-amino)-2H-phthalazin-1-one | (400MHz, $D_6$-DMSO) 9.51(1H, s), 8.34(1H, s), 8.24(1H, d), 7.91-7.80(2H, m), 7.41-7.29(2H, m), 7.16-7.13(1H, m), 6.04(1H, s), 5.21(2H, s), 2.16(3H, s) | 368.20 |
| A-16 | 4-(5-methyl-1H-pyrazol-3-ylamino)-2-(2-methyl-thiazol-4-ylmethyl)-2H-phthalazin-1-one | (400MHz, $D_6$-DMSO) 9.82(1H, s), 8.39(1H, d), 8.33(1H, d), 7.99-7.88(2H, m), 7.36(1H, d), 6.16(1H, s), 5.34(2H, s), 2.64(3H, s), 2.26(3H, s) | 353.18 |
| A-17 | 4-(5-methyl-2H-pyrazol-3-ylamino)-2-pyridin-4-ylmethyl-2H-phthalazin-1-one | (400MHz, $D_6$-DMSO) 9.38(1H, s), 8.70(2H, d), 8.44(1H, d), 8.31(1H, d), 7.98-7.86(2H, m), 7.69(2H, d), 6.06(1H, s), 5.46(2H, s), 2.17(3H, s) | 333.21 |
| A-18 | 4-(5-methyl-2H-pyrazol-3-ylamino)-2- | (400MHz, $D_6$-DMSO) 9.38(1H, s), 8.68(2H, d), 8.54(2H, d), 8.29(2H, d), | 333.14 |

-continued

| Example No. | Systematic name | ¹H-NMR | MS (ESI+, M + H) |
|---|---|---|---|
| | pyridin-3-ylmethyl-2H-phthalazin-1-one | 8.17(2H, dd), 8.05(2H, d), 7.83-7.72(4H, m), 7.58(2H, dd), 5.95(2H, s), 5.27(3H, s), 2.07(4H, s) | |
| A-19 | 2-(2-fluoro-benzyl)-4-(5-methyl-1H-pyrazol-3-ylamino)-2H-phthalazin-1-one | (400MHz, $D_6$-DMSO) 9.45(1H, s), 8.42(1H, d), 8.31(1H, dd), 7.96-7.85(2H, m), 7.38-7.31(2H, m), 7.24-7.13(2H, m), 5.97(1H, s), 5.33(2H, s), 2.16(3H, s) | 350.11 |
| A-20 | 2-(4-fluoro-benzyl)-4-(5-methyl-1H-pyrazol-3-ylamino)-2H-phthalazin-1-one | (400MHz, $D_6$-DMSO) 9.53(1H, s), 8.40(1H, d), 8.31(1H, dd), 7.96-7.85(2H, m), 7.41(2H, dd), 7.15(2H, t), 6.11(1H, s), 5.26(2H, s), 2.22(3H, s) | 350.11 |
| A-21 | 2-(3,5-difluoro-benzyl)-4-(5-methyl-1H-pyrazol-3-yl-amino)-2H-phthalazin-1-one | (400MHz, $D_6$-DMSO) 9.59(1H, s), 8.44(1H, d), 8.33(1H, dd), 7.99-7.88(2H, m), 7.17(2H, tt), 7.08(2H, dd), 6.12(1H, s), 5.32(2H, s), 2.23(3H, s) | 368.10 |
| A-22 | 4-(5-methyl-2H-pyrazol-3-ylamino)-2-pyridin-2-ylmethyl-2H-phthalazin-1-one | (400MHz, $D_6$-DMSO) 9.23(1H, s), 8.54(1H, d), 8.47(1H, d), 8.31(1H, d), 7.97-7.85(2H, m), 7.76(1H, t), 7.32-7.24(2H, m), 5.95(1H, s), 5.36(2H, s), 2.13(3H, s) | 333.28 |
| A-23 | 2-isopropyl-4-(5-methyl-1H-pyrazol-3-ylamino)-2H-phthalazin-1-one | (400MHz, $D_6$-DMSO) 11.73(1H, br s), 8.99(1H, br s), 8.25(1H, d), 8.10(1H, d), 7.71-7.62(2H, m), 6.16(1H, t), 5.10-5.03(1H, m), 2.05(3H, s), 1.13(6H, d) | 284.34 |
| A-24 | 3-[4-(5-methyl-1H-pyrazol-3-ylamino)-1-oxo-1H-phthalazin-2-ylmethyl]-benzoic acid | (400MHz, $D_6$-DMSO) 11.94-11.76(1H, m), 9.26(1H, br s), 8.46(1H, d), 8.31(1H, d), 7.92-7.82(3H, m), 7.75(1H, d), 7.33-7.22(2H, m), 6.08(1H, s), 5.23(2H, s), 2.14(3H, s) | 376.15 |
| A-25 | 4-(5-methyl-1H-pyrazol-3-ylamino)-2-(4-trifluoromethyl-phenyl)-2H-phthalazin-1-one | (400MHz, DMSO) 9.28(1H, s), 8.41(1H, d), 8.27(1H, d), 7.96-7.73(6H, m), 6.13(1H, s), 2.05(3H, s) | 386.1 |

Example A-2 is composed as Example E-1 under Method E.

Method B:

Example B-1

2-(4-Chloro-phenyl)-4-(5-methyl-1H-pyrazol-3-ylamino)-2H-phthalazin-1-one 2-(4-chlorophenyl)-2,3-dihydro-phthalazine-1,4-dione: 4-Chlorophenyl hydrazine hydrochloride (5.00 g, 28 mmol) was added in one portion to a stirred mixture of phthalic anhydride (3.70 g, 25 mmol), in HOAc (50 ml) at RT. The mixture was heated to 125° C. for 2 hours, and then allowed to cool to RT. The suspension was poured into water (100 ml) and the precipitate was filtered. The precipitate was stirred in 1M $Na_2CO_3$ (100 ml), and the remaining undissolved solid removed by filtration. This solid was washed with a further 100 ml portion of 1M $Na_2CO_3$.

The basic aqueous solutions were combined and acidified by dropwise addition of conc. HCl until gas evolution ceased. A white precipitate formed and was filtered and dried for 18 hours in a vacuum oven (50° C.) to give the phthalazine dione (270 mg, 4% yield).

The solid insoluble in 1M $Na_2CO_3$ was stirred in glycerol (50 ml) and heated to 150° C. for 10 hrs. The reaction mixture was then diluted with water (50 ml). 4M HCl was added dropwise until a precipitate formed. This was filtered, re-suspended in MeOH (30 ml) and isolated by filtration. The product was dried under vacuum to give the desired phthalazine dione (3.6 g, 72% yield). ¹H-NMR: (400 MHz; $D_6$-DMSO); 12.1 (1H, br. s), 8.3 (1H, d), 7.9-8.0 (3H, m), 7.7 (2H, d), 7.6 (2H, d); MS (ESI⁺)=(M+H)⁺ 273, 275

This material was then brominated with phosphorus oxybromide and used in the Buchwald reaction as described in Method A. to give the corresponding 2-(4-Chloro-phenyl)-4-(5-methyl-1H-pyrazol-3-ylamino)-2H-phthalazin-1-one (example B-1).

Using the experimental conditions reported above (Method B) and the appropriate starting materials, the following derivatives were prepared:

| Example No. | Systematic name | ¹H-NMR | MS (ESI+, M + H) |
|---|---|---|---|
| B-1 | 2-(4-Chloro-phenyl)-4-(5-methyl-1H- | (400MHz, $D_6$-DMSO), 11.97(1H, s) 9.34(1H, s), 8.51(1H, d), 8.38(1H, d), | 352.30 |

-continued

| Example No. | Systematic name | ¹H-NMR | MS (ESI+, M + H) |
|---|---|---|---|
| B-2 | pyrazol-3-ylamino)-2H-phthalazin-1-one 4-(5-Methyl-1H-pyrazol-3-ylamino)-2-m-tolyl-2H-phthalazin-1-one | 7.99-7.89(2H m), 7.80(2H, d), 7.58(2H, d) 6.24(1H, s), 2.20(3H, s) (400MHz, $D_6$-DMSO) 9.45(1H s), 8.49(1H, d), 8.38(1H, d), 7.98-7.91(2H, m), 7.54-7.50(1H m), 7.38(1H, t), 7.17(1H d), 6.26(1H, s), 2.38(3H, s), 2.20(3H, s) | 332.34 |
| B-3 | 4-(5-Methyl-1H-pyrazol-3-ylamino)-2-(4-nitro-benzyl)-2H-phthalazin-1-one | (400MHz, $D_6$-DMSO) 9.32(1H, s), 8.34(2H, d), 8.21(2H, d), 8.0(2H, d), 7.49-.7.85(2H, m), 7.49(2H d), 5.93(1H, s), 5.29(2H, s), 2.04(3H, s) | 377.24 |

Method C

Example C-1

2-(4-Aminobenzyl)-4-(5-methyl-1H-pyrazol-3-ylamino)-2H-phthalazin-1-one

Tin (II) chloride dihydrate (1.3 g, 5.76 mmol) was added to a suspension of 4-(5-Methyl-1H-pyrazol-3-ylamino)-2-(4-nitro-benzyl)-2H-phthalazin-1-one (Example B-3) (600 mg, 1.6 mmol) in dimethylformamide (DMF) (10 ml). The reaction mixture was stirred at RT overnight. The DMF was evaporated under reduced pressure and the residue dissolved in DCM. A saturated solution of potassium sodium tartrate tetrahydrate in water (20 ml) was added and the mixture stirred for 30 min.

The phases were separated and the aqueous phase back-extracted with DCM (20 ml). The organic layers were combined, washed with brine, and evaporated under reduced pressure to give 2-(4-Aminobenzyl)-4-(5-methyl-1H-pyrazol-3-ylamino)-2H-phthalazin-1-one as an off-white solid (55 mg, 10% yield). ¹H-NMR: (400 MHz, $D_6$-DMSO) 9.37 (1H, s), 8.40 (2H, d), 8.28 (2H, d), 7.81-7.91 (2H, m), 7.32 (2H, d), 7.04 (2H d), 6.12 (1H, s), 5.18 (2H, s), 2.17 (3H, s), MS (ESI$^+$)=(M+H)$^+$ 347.31.

Using the experimental conditions reported above (Method C) and the appropriate starting material W-3, the following derivative was prepared:

| Example No. | Systematic name | ¹H-NMR | MS (ESI+, M + H) |
|---|---|---|---|
| C-2 | 2-(4-amino-phenyl)-4-(5-methyl-1H-pyrazol-3-ylamino)-2H-phthalazin-1-one | (400MHz, $D_6$-DMSO), 11.90(1H, s), 9.15(1H, s), 8.47(1H, d), 8.33(1H, d), 7.85-7.94(2H, m), 7.28(2H, d), 6.65(2H, d), 6.25(1H, s), 5.23(2H, s), 2.18(3H, s) | 333.3 |

Method D

Example D-1

N-{4-[4-(5-Methyl-1H-pyrazol-3-ylamino)-1-oxo-1H-phthalazin-2-yl-methyl]-phenyl}-acetamide 4-Bromo-2-(4-aminobenzyl)-2H-phthalazin-1-one: Tin (II) chloride dihydrate (68 mg, 3.6 eq) was added to a suspension of 4-bromo-2-(4-nitrobenzyl)-2H-phthalazin-1-one (30 mg, 0.09 mmol) in DMF (0.5 ml). The reaction mixture was stirred at RT overnight. The DMF was evaporated under reduced pressure and the residue dissolved in DCM (0.5 ml). A saturated solution of potassium sodium tartrate tetrahydrate in water (0.5 ml) was added and the mixture stirred for 30 min.

The phases were separated and the aqueous phase back-extracted with DCM (0.5 ml). The organic layers were combined, washed with brine, and evaporated under reduced pressure to give the desired product as an off-white solid (23 mg, 87% yield) ¹H-NMR: (400 MHz; $C_6D_6$); 8.42 (1H, d), 7.91 (1H, d), 7.83 (2H, m), 7.33 (2H, d), 6.63 (2H, d), 5.25 (2H, s). MS (ESI$^+$)=(M+H)$^+$ 330.2, 332.2.

4-Bromo-2-(4-acetylaminobenzyl)-2H-phthalazin-1-one: Acetic anhydride (0.43 ml, 4.5 mmol) was added to a mixture of 4-bromo-2-(4-aminobenzyl)-2H-phthalazin-1-one (500 mg, 1.5 mmol) and pyridine (0.49 ml, 6 mmol) in MeCN (5 ml). The reaction mixture was stirred at RT overnight. The solvent was removed under reduced pressure. 1M ammonia in MeOH (2 ml) was added and the reaction mixture stirred for 1 hr. The solvent was removed under reduced pressure. The residue was triturated with DCM to give the product as an off-white solid (398 mg, 71% yield) MS (ESI$^+$)=(M+H)$^+$ 372.2, 374.2.

This material was then used in the Buchwald reaction as described in Method A. to give the corresponding N-{4-[4-(5-Methyl-1H-pyrazol-3-ylamino)-1-oxo-1H-phthalazin-2-yl-methyl]-phenyl}-acetamide (example D-1).

Using the experimental conditions reported above (Method D) and the appropriate starting materials, the following derivatives were prepared:

| Example No. | Systematic name | ¹H-NMR | MS (ESI+, M + H) |
|---|---|---|---|
| D-1 | N-{4-[4-(5-Methyl-1H-pyrazol-3-ylamino)-1-oxo-1H-phthalazin-2-ylmethyl]-phenyl}-acetamide | (400MHz, D$_6$-DMSO) 9.94(1H, s), 9.26(1H, s), 8.42(2H, d), 8.32(2H d), 7.85-7.94(2H, m), 7.52(2H, d), 7.31(2H d), 6.10(1H, s), 5.18(2H, s), 2.19(3H, s), 2.17(3H, s) | 389.27 |
| D-2 | N-{4-[1-Oxo-4-(1H-pyrazol-3-ylamino)-1H-phthalazin-2-ylmethyl]-phenyl}-acetamide | (400MHz, D$_6$-DMSO) 12.16(1H, s) 9.84(1H, s), 8.38(1H, d), 8.25(1H, d), 7.87-7.78(2H m), 7.50(1H, d), 7.45(2H, d) 7.23(2H, d), 6.40(1H, s), 5.10(2H, s), 1.93(3H, s) | 375.29 |

Method E

Example E-1

2-Benzyl-4-(5-methyl-1H-pyrazol-3-ylamino)-2H-phthalazin-1-one

4-Bromo-2H-phthalazin-1-one: 2,3-Dihydro-1,4-phthalazinedione (12.5 g, 78 mmol) was suspended in DCE (200 ml) and phosphorous pentabromide (50.0 g, 116 mmol) was added in one portion and the reaction heated to reflux for 24 hours. A further portion of phosphorous pentabromide (20.0 g, 70 mol) was added and the reaction heated for a further 24 hours. The reaction was cooled to RT and poured into ice water. The resulting precipitate was filtered and washed with water to give a crude mixture of mono and dibrominated product (22.8 g).

This crude material was suspended in HOAc (230.0 mL) and heated to 120° C. for 2 hrs. The reaction was cooled to RT and poured into ice water and the resulting precipitate filtered. The solid was washed with water and dried to give the title compound (10.4 g, 60% yield) as a white solid. ¹H-NMR: (400 MHz, D$_6$-DMSO), 12.95 (1H, s), 8.25 (1H, dd), 8.03 (1H, ddd), 7.96-7.90-(2H, m); MS (ESI$^+$)=(M+H)$^+$ 225 & 227

2-Benzyl-4-bromo-2H-phthalazin-1-one: 4-Bromo-2H-phthalazin-1-one (10.38 g, 46 mmol) was dissolved in dimethylformamide (DMF) (60 ml). To this was added NaH (60%, 1.55 g, 46.2 mmol) as a DMF suspension (20 ml). The mixture was stirred at RT for 30 mins then benzyl bromide (13.82 g, 50.8 mmol) was added in one portion as a solution in DMF (20 ml). The reaction mixture was stirred for 2 hours then the DMF was removed under reduced pressure and the resulting crude material purified by column chromatography (gradient elution: 100% heptane to 20% EtOAc: heptane) to give the title compound (8.16 g, 56% yield) as a white solid. ¹H-NMR: (400 MHz, D$_6$-DMSO), 8.30 (1H, dd), 8.03 (1H, ddd), 7.97-7.91 (2 H, m), 7.34-7.27 (5H, m), 5.31 (2H, s); MS (ESI$^+$)=(M+H)$^+$ 315 & 317

This material was then used in the Buchwald reaction as described in Method A. to give the corresponding 2-Benzyl-4-(5-methyl-1H-pyrazol-3-ylamino)-2H-phthalazin-1-one (example E-1).

Using the experimental conditions reported above (Method E) and the appropriate starting materials, the following derivatives were prepared:

| Example No. | Systematic name | ¹H-NMR | MS (ESI+, M + H) |
|---|---|---|---|
| E-1 | 2-benzyl-4-(5-methyl-1H-pyrazol-3-yl-amino)-2H-phthalazin-1-one | (400MHz, D$_6$-DMSO) 11.86(1H, s), 9.25(1H, s), 8.46(1H, d), 8.32(1H, d), 7.84-.7.94(2H, m), 7.25-7.38(5H m), 6.10(1H, s), 5.24(2H, s) 2.17(3H, s) | 332.08 |
| E-2 | 7-Fluoro-2-isopropyl-4-(5-methyl-1H-pyrazol-3-ylamino)-2H-phthalazin-1-one | (400MHz, D$_6$-DMSO) 9.35(1H, s), 8.53(1H, dd), 7.95(1H, dd), 7.82(1H, ddd), 6.35(1H, s), 5.27-5.19(1H, m), 2.26(3H, s), 1.32(6H, s) | 302.29 |
| E-3 | 6-Fluoro-2-isopropyl-4-(5-methyl-1H-pyrazol-3-ylamino)-2H-phthalazin-1-one | (400MHz, D$_6$-DMSO) 9.09(1H, s), 8.19-8.14(2H, m), 7.56-7.50(1H, m), 6.18(1H, s), 5.09-5.00(1H, m), 2.07(3H, s), 1.14(6H, d) | 302.29 |
| E-4 | 2-[2-(4-Methoxy-phenyl)-2-oxo-ethyl]-4-(5-methyl-1H-pyrazol-3-ylamino)-2H-phthalazin-1-one | (400MHz, D$_6$-DMSO) 9.43(1H, s), 8.40(1H, d), 8.22(1H, d), 8.00(2H, d), 7.93-7.81(2H, m), 7.04(2H, d), 6.12(1H, s), 5.54(2H, s), 3.80(3H, s), 2.11(3H, s) | 390.14 |
| E-5 | 2-[2-(3-Methoxy-phenyl)-2-oxo-ethyl]-4-(5-methyl-1H-pyrazol-3-ylamino)-2H-phthalazin-1-one | (400MHz, D$_6$-DMSO) 9.38(1H, s), 8.43(1H, d), 8.21(1H, d), 7.92-7.80(2H, m), 7.61(1H, d), 7.49-7.42(2H, m), 7.21(1H, d), 6.11(1H, s), 5.57(2H, s), 3.77(3H, s), 2.09(3H, s) | 390.15 |
| E-6 | 4-(5-methyl-1H-pyrazol-3-ylamino)-2-[2-oxo-2-(4-trifluoromethoxy- | (400MHz, D$_6$-DMSO) 12.06(1H, br s), 9.41(1H, br s), 8.64(1H, d), 8.45-8.36(3H, m), 8.14-8.02(2H, m), 7.75(2H, | 444.23 |

-continued

| Example No. | Systematic name | $^1$H-NMR | MS (ESI+, M + H) |
|---|---|---|---|
| | phenyl)-ethyl]-2H-phthalazin-1-one | d), 6.38(1H, s), 5.79(2H, s), 2.30(3H, s) | |
| E-7 | 2-(2-Benzo[1,3]dioxol-5-yl-2-oxo-ethyl)-4-(5-methyl-1H-pyrazol-3-ylamino)-2H-phthalazin-1-one | (400MHz, D$_6$-DMSO) 9.26(1H, br s), 8.48(1H, d), 8.30(1H, d), 7.97-7.88(2H, m), 7.75(1H, d), 7.56(1H, s), 7.12(1H, d), 6.18(2H, s), 5.55(2H, s), 2.16(3H, s) | 404.18 |
| E-8 | 4-(5-methyl-1H-pyrazol-3-ylamino)-2-[2-oxo-2-(4-trifluoromethyl-phenyl)-ethyl]-2H-phthalazin-1-one | (400MHz, D$_6$-DMSO) 11.84(1H, br s), 9.26(1H, br s), 8.42(1H, d), 8.22-8.20(3H, m), 7.91-7.80(4H, m), 6.12(1H, s), 5.61(2H, s), 2.08(3H, s) | 428.09 |
| E-9 | 4-(5-methyl-1H-pyrazol-3-ylamino)-2-(2-oxo-2-phenyl-ethyl)-2H-phthalazin-1-one | (400MHz, DMSO) 11.91(1H, br s), 9.31(1H, br s), 8.48(1H, d), 8.30(1H, d), 8.09(2H, d), 7.98-7.87(2H, m), 7.74-7.70(1H, m), 7.62-7.58(2H, m), 6.21(1H, s), 5.63(2H, s), 2.15(3H, s) | 360.10 |
| E-10 | 2-allyl-4-(5-methyl-1H-pyrazol-3-yl-amino)-2H-phthalazin-1-one | (400MHz, D$_6$-DMSO) 11.90(1H, s), 9.20(1H, s), 8.45(1H, d,), 8.29(1H, d), 7.98-7.81(2H, m), 6.36(1H, s), 6.06-5.94(1H, m), 5.23-5.15(2H, m), 4.69-4.61(2H, m), 2.21(3H, s) | 282.09 |
| E-11 | 2-Cyclopropylmethyl-4-(5-methyl-1H-pyrazol-3-ylamino)-2H-phthalazin-1-one | (400MHz, D$_6$-DMSO) 11.91(1H, s), 9.16(1H, s), 8.44(1H, d), 8.29(1H, dd), 7.94-7.82(2H, m), 6.36(1H, s), 3.91(2H, d), 2.23(3H, s), 1.34-1.25(1H, m), 0.52-0.46(2H, m), 0.43-0.37(2H, m) Tr=1.54min, m/z(ES$^+$) (M+H)$^+$ 296.12 | |
| E-12 | 4-(5-Methyl-1H-pyrazol-3-ylamino)-2-(4-methylsulfanyl-benzyl)-2H-phthalazin-1-one | (400MHz, D$_6$-DMSO) 11.88(1H, s), 9.21(1H, s), 8.44(1H, d), 8.31(1H, dd), 7.94-7.84(2H, m), 7.34-7.30(2H, m), 7.25-7.21(2H, m), 6.11(1H, s), 5.19(2H, s), 2.43(3H, s), 2.19(3H, s) Tr=1.87min, m/z(ES$^+$) (M+H)$^+$ 378.08 | |

Example E-13

2-(2-Hydroxy-2-phenyl-ethyl)-4-(5-methyl-1H-pyrazol-3-ylamino)-2H-phthalazin-1-one Sodium borohydride (6 mg, 0.15 mmol) was added in one portion to a stirred solution of 4-(5-Methyl-1H-pyrazol-3-ylamino)-2-(2-oxo-2-phenyl-ethyl)-2H-phthalazin-1-one (17 mg, 0.05 mmol) (Example E-9) in THF (1 ml). The reaction mixture was stirred at RT for two hours. After this time LC-MS indicated complete consumption of starting material, MeOH (0.5 ml) was added and the reaction mixture was concentrated under vacuum. The resulting residue was purified by flash column chromatography (elution: 97% DCM, 3% MeOH) to give the title compound (2.2 mg, 12% yield) as a white solid. MS (ESI$^+$)=(M+H)$^+$ 361.98.

Method F:

Example F-1

2-Isopropyl-4-(5-methyl-1H-pyrazol-3-ylamino)-7-morpholino-2H-phthalazin-1-one 7-Nitro-2,3-dihydro-phthalazine-1,4-dione: Hydrazine hydrate (26.6 g, 0.53 mol) was added in one portion to a stirred mixture of 4-nitrophthalic anhydride (100 g, 0.52 mol), in HOAc (1.0 L) at RT. The mixture was heated to 120° C. for 2 hours and then allowed to cool to RT. The solid was filtered, washed with water (250 ml) and dried in the vacuum oven at 50° C. for 20 hours to give the nitrophthalazinone (95 g, 88% yield). MS (ESI$^+$)=(M+H$^+$) 208.

7-Nitro-4-bromo-2H-phthalazin-1-one: 7-Nitro-2,3-dihydro-phthalazine-1,4-dione (95.0 g, 0.46 mol) was suspended in DCE (1.0 L) and phosphorus pentabromide (789.0 g, 1.83 mol) was added in three portions and the reaction heated to reflux for 24 hours. The reaction was cooled to RT and poured onto ice (2.5 kg) and the resulting precipitate filtered and washed with water to give the crude product (160 g).

This crude material was suspended in HOAc (1.60 L) and heated to 125° C. for 2 hours. The reaction was cooled to RT and poured onto ice (1.5 kg) and the resulting precipitate filtered. The solid was washed with water and dried to give the title compound (84 g, 68% yield) as a yellow solid.

$^1$H-NMR: (400 MHz, D$_6$-DMSO), 13.29 (1H,), 8.83 (1H, d), 8.79 (1H, dd), 8.61 (1H, dd), 8.54 (1H, d), 8.46 (1H, d), 8.16 (d) MS (ESI$^+$)=(M+H)$^+$ 269 & 271

7-Nitro-2-Isopropyl-4-bromo-2H-phthalazin-1-one: 7-Nitro-4-bromo-2H-phthalazin-1-one (84 g, 0.31 mol) was dissolved in dimethylformamide (DMF) (400 ml). To this was added NaH (60%, 7.5 g, 0.31 mol) as a DMF suspension (200 ml). The mixture was stirred at RT for 30 min then 2-bromo-propanol (7.7 g, 62 mmol) was added in one portion as a solution in DMF (250 ml). The reaction mixture was stirred for 24 hours whereupon LC-MS showed 40% starting material remaining. To this was added NaH (3.75 g 0.15 mol) and the reaction stirred for a further 24 hours. The DMF was removed under vacuum and the resulting crude material purified by successive column chromatography (elution: 92% heptane to 8% EtOAc) to give the title compound (38.8 g, 40% yield) as a light yellow solid. $^1$H-NMR: (400 MHz, D$_6$-DMSO), 8.88 (1H, d), 8.87 (1H, dd), 8.16 (1 H, d), 5.19 (1H, m), 1.13 (6H, d).

7-Amino-2-Isopropyl-4-bromo-2H-phthalazin-1-one:
7-Nitro-2-Isopropyl-4-bromo-2H-phthalazin-1-one (4.6 g, 0.015 mol) was dissolved in a 5:1 mixture of EtOH and water (150 ml). To this solution was added iron powder (2.14 g, 0.039 mol) and concentrated HCl (1 ml), the mixture was heated to 80° C. for three hours. After this time, the reaction mixture was cooled to RT and filtered through a pad of celite, the celite was washed with EtOH (100 ml), and the solution was concentrated under vacuum to give the title compound (4.2 g, 98% yield) as a white solid. $^1$H-NMR: (400 MHz, D$_6$-DMSO), 7.56 (1H, d), 7.28 (1H, s), 7.13 (1 H, d), 6.47 (2H, s), 5.24-5.09 (1H, m), 1.23 (6H, d); MS (ESI$^+$)=(M+H)$^+$ 282, 284

7-Morpholino-2-Isopropyl-4-bromo-2H-phthalazin-1-one: To a solution of 7-Amino-2-Isopropyl-4-bromo-2H-phthalazin-1-one (0.8 g, 0.0028 mol) in DMF (8 ml), was added potassium carbonate (2 g, 0.014 mol). After 5 min, bis (2-chloroethyl) ether (0.41 g, 0.0028 mol) was added and the solution was heated to 140° C. for 24 hours. After this time LC-MS indicated the complete consumption of starting material and the mixture was cooled, concentrated under vacuum and purified by flash column chromatography (elution: 70% heptane, 30% EtOAc) to give the title compound (0.2 g, 20% yield) as a white solid.

This material was then used in the Buchwald reaction as described in Method A. to give the corresponding 2-Isopropyl-4-(5-methyl-1H-pyrazol-3-ylamino)-7-morpholino-2H-phthalazin-1-one (example F-1)

Using the experimental conditions reported above (Method F) and the appropriate starting materials, the following derivatives were prepared:

| Example No. | Systematic name | $^1$H-NMR | MS (ESI+, M + H) |
|---|---|---|---|
| F-1 | 2-isopropyl-4-(5-methyl-1H-pyrazol-3-ylamino)-7-morpholino-2H-phthalazin-1-one | (400MHz, D$_6$-DMSO) 11.86(1H, s), 8.97(1H, s), 8.29(1H, d), 7.57(1H, d), 7.52(1H, d), 6.35(1H, br s), 5.28-5.20(1H, m), 3.79-3.74(4H, m), 3.21(4H, obscured), 2.23(3H, s), 1.30(6H, d) | 368.15 |
| F-2 | 2-Isopropyl-4-(5-methyl-1H-pyrazol-3-ylamino)-6-morpholino-2H-phthalazin-1-one | (400MHz, D$_6$-DMSO) 11.88(1H, s), 9.19(1H, s), 8.07(1H, d), 7.65(1H, s), 7.41(1H, dd), 6.37(1H, s), 5.25-5.16(1H, m), 3.80-3.73(4H, m), 3.44-3.35(4H, m), 1.28(6H, d) | 369.37 |
| F-3 | 2-Isopropyl-4-(5-methyl-1H-pyrazol-3-ylamino)-8-morpholino-2H-phthalazin-1-one | (400MHz, DMSO) 9.45(1H, br s), 8.35(1H, br s), 8.03(1H, br s), 6.33(1H, s), 5.31-5.17(1H, m), 3.96(4H, br s), 3.51(4H, br s), 2.26(3H, s), 1.35(6H, d) | 369.30 |
| F-4 | 2-Benzyl-4-(5-methyl-1H-pyrazol-3-yl-amino)-7-morpholino-2H-phthalazin-1-one | (400MHz, D$_6$-DMSO) 9.50(1H, s), 8.10(1H, d), 7.61(1H, d), 7.46(1H, dd), 7.34-7.23(5H, m), 6.14(1H, s), 5.22(2H, s), 3.83-3.72(4H, m), 3.42-3.40(4H, m), 2.20(3H, s) | 417.30 |
| F-5 | 2-Isopropyl-7-(4-methyl-piperazin-1-yl)-4-(5-methyl-2H-pyrazol-3-ylamino)-2H-phthalazin-1-one | (400MHz, CDCl$_3$) 7.83(1H, d), 7.61(1H, d), 7.31(1H, dd), 7.15(1H, s), 6.33(1H, s), 5.49-5.41(1H, m), 3.46-3.41(4H, m), 2.61-2.55(4H, m), 2.37(3H, s), 2.35(3H, s), 1.43(6H, d) | 382.33 |
| F-6 | 2-Isopropyl-4-(5-methyl-1H-pyrazol-3-ylamino)-7-dimethylamino-2H-phthalazin-1-one | (400MHz, D$_6$-DMSO) 9.21(1H, s), 8.27(1H, d), 7.41(1H, d), 7.35(1H, dd), 6.42(1H, s), 5.36-5.29(1H, m), 3.16(6H, s), 2.34(3H, s), 1.39(6H, d) | 327.36 |
| F-7 | 2-Isopropyl-4-(5-methyl-1H-pyrazol-3-ylamino)-6-dimethylamino-2H-phthalazin-1-one | | 327.30 |
| F-8 | 2-Isopropyl-4-(5-methyl-1H-pyrazol-3-ylamino)-8-dimethylamino-2H-phthalazin-1-one | (400MHz, D$_6$-DMSO) 11.82(1H, br s), 8.77(1H, br s), 7.67-7.56(2H, m), 7.20(1H, d), 6.26(1H, br s), 5.26-5.15(1H, m), 2.84(6H, s), 2.22(3H, s), 1.27(6H, d) | 327.18 |
| F-9 | 4-(5-Cyclopropyl-2H-pyrazol-3-yl-amino)-7-dimethyl-amino-2-isopropyl-2H-phthalazin-1-one | (400MHz, DMSO) 11.89(1H, br s), 8.90(1H, br s), 8.23(1H, br s), 7.32(1H, d), 7.24(1H, d), 6.25(1H, br s), 5.29-5.18(1H, m), 3.07(6H, s), 1.92-1.84(1H, m), 1.29(6H, d), 0.98-0.88(2H, m), 0.65(2H, dd) | 353.41 |
| F-10 | 2-Isopropyl-4-(5-methyl-1H-pyrazol-3-ylamino)-7-piperidin-1-yl-2H-phthalazin-1-one | (400MHz, DMSO) 9.04(1H, s), 8.32(1H, d), 7.63(1H, d), 7.57(1H, dd), 6.42(1H, s), 5.40-5.25(1H, m), 3.49(4H, s), 2.32(3H, s), 1.70(6H, br s), 1.39(6H, d) | 367.22 |

-continued

| Example No. | Systematic name | ¹H-NMR | MS (ESI+, M + H) |
|---|---|---|---|
| F-11 | 2-Isopropyl-4-(5-methyl-1H-pyrazol-3-ylamino)-7-pyrrolidin-1-yl-2H-phthalazin-1-one | (250MHz, DMSO) 8.88(1H, s), 8.23(1H, d), 7.18(1H, d), 7.11-7.03(1H, m), 6.35(1H, s), 5.33-5.18(1H, m), 3.39(4H, br s), 2.24(3H, s), 2.02(4H, br s), 1.31(6H, d) | 353.18 |

Method G:

Example G-1

2-Isopropyl-4-(5-methyl-1H-pyrazol-3-ylamino)-7-methoxy-2H-phthalazin-1-one

7-Hydroxy-2-Isopropyl-4-bromo-2H-phthalazin-1-one: Concentrated sulfuric acid (17 ml) was added slowly to a solution of 7-Amino-2-Isopropyl-4-bromo-2H-phthalazin-1-one (4.6 g, 0.016 mol) in HOAc (50 ml). The reaction mixture was cooled to 0° C. and a solution of NaNO₂ (1.52 g, 0.022 mol) in water (10 ml) was added dropwise. The reaction mixture was stirred for a further 20 min at 0° C. prior to the addition of urea (0.55 g, 0.009 mol) and cold water (50 ml). The reaction mixture was then added carefully to a refluxing mixture of sulfuric acid (28 ml) in water (115 ml) and the reaction was stirred for a further 10 min at reflux before being allowed to cool to RT. Upon standing, an orange precipitate was observed, which was collected by filtration and washed with water to give the title compound (4.22 g, 93% yield) as an orange powder.

7-Methoxy-2-Isopropyl-4-bromo-2H-phthalazin-1-one: To a stirred solution of 7-hydroxy-2-Isopropyl-4-bromo-2H-phthalazin-1-one (0.4 g, 1.4 mmol) in THF (5 ml) were added successively, K₂CO₃ (0.59 g, 4.3 mmol) and methyl iodide (0.22 g, 1.55 mmol) and the mixture was heated to reflux for 24 hours. After this time, LC-MS indicated complete consumption of starting material, and the reaction mixture was concentrated under vacuum. The residue was re-dissolved in EtOAc (50 ml) and washed with water (2×30 ml), the organic layer was dried (MgSO₄), filtered and concentrated under vacuum to give the title compound (0.32 g, 76% yield) as an orange powder.

This material was then used in the Buchwald reaction as described in Method A. to give the corresponding 2-Isopropyl-4-(5-methyl-1H-pyrazol-3-ylamino)-7-methoxy-2H-phthalazin-1-one (example G-1)

Using the experimental conditions reported above (Method G) and the appropriate starting materials, the following derivatives were prepared:

| Example No. | Systematic name | ¹H-NMR | MS (ESI+, M + H) |
|---|---|---|---|
| G-1 | 2-Isopropyl-4-(5-methyl-1H-pyrazol-3-ylamino)-7-methoxy-2H-phthalazin-1-one | (400MHz, D₆-DMSO) 12.07(1H, s), 9.27(1H, s), 8.56(1H, d), 7.85(1H, s), 7.63(1H, d), 6.52(1H, s), 5.46-5.39(1H, m), 4.10(3H, s), 2.86(3H, s), 1.50(6H, d) | 314.32 |
| G-2 | 2-Isopropyl-4-(5-methyl-1H-pyrazol-3-ylamino)-7-(pyridin-2-ylmethoxy)-2H-phthalazin-1-one | (250MHz, D₆-DMSO) 9.12(1H, br s), 8.62-8.58(1H, m), 8.40(1H, d), 7.89-7.81(1H, m), 7.74(1H, d), 7.59-7.52(2H, m), 7.40-7.33(1H, m), 6.32(1H, s), 5.38(2H, s), 5.29-5.13(1H, m), 2.23(3H, s), 1.31(6H, d) | 391 |
| G-3 | 2-Isopropyl-4-(5-methyl-1H-pyrazol-3-ylamino)-7-(pyridin-3-ylmethoxy)-2H-phthalazin-1-one | (250MHz, D₆-DMSO) 9.13(1H, br s), 8.73(1H, d), 8.57(1H, dd), 8.41(1H, d), 7.96-7.89(1H, m), 7.80(1H, d), 7.55(1H, dd), 7.49-7.41(1H, m), 6.33(1H, s), 5.36(2H, s), 5.31-5.19(1H, m), 2.24(3H, s), 1.32(6H, d) | 391 |
| G-4 | 2-Isopropyl-4-(5-methyl-1H-pyrazol-3-ylamino)-7-(pyridin-4-ylmethoxy)-2H-phthalazin-1-one | (250MHz, D₆-DMSO) 9.13(1H, br s), 8.64-8.58(2H, m), 8.42(1H, d), 7.76(1H, d), 7.58(1H, dd), 7.52-7.46(2H, m), 6.34(1H, s), 5.41(2H, s), 5.32-5.18(1H, m), 2.24(3H, s), 1.32(6H, d) | 391.21 |
| G-5 | 2-isopropyl-4-(5-methyl-1H-pyrazol-3-ylamino)-7-(2-morpholin-4-yl-ethoxy)-2H-phthalazin-1-one | (250MHz, D₆-DMSO) 9.09(1H, br s), 8.38(1H, d), 7.69(1H, d), 7.46(1H, dd), 6.33(1H, s), 5.31-5.17(1H, m), 4.27(2H, t), 3.62-3.55(4H, m), 3.41(4H, obscured), 2.75(2H, t), 2.24(3H, s), 1.32(6H, d) | 413.28 |
| G-6 | 7-Hydroxy-2-isopropyl-4-(5-methyl-1H-pyrazol-3-yl-amino)-2H-phthalazin-1-one | (400MHz, D₆-DMSO) 11.84(1H, s), 10.59(1H, s), 8.99(1H, s), 8.27(1H, d), 7.58(1H, d), 7.25(1H, dd), 6.32(1H, s), 5.28-5.16(1H, m), 2.23(3H, s), 1.30(6H, d) | 300.33 |

-continued

| Example No. | Systematic name | $^1$H-NMR | MS (ESI+, M + H) |
|---|---|---|---|
| G-7 | 7-Difluoromethoxy-2-isopropyl-4-(5-methyl-1H-pyrazol-3-yl-amino)-2H-phthalazin-1-one | (400MHz, DMSO), 12.03(1H, br s), 9.31(1H, br s), 8.61(1H, d), 7.62-7.49(1H, m), 7.43(1H, s), 6.41(1H, s), 5.37-5.22(1H, m), 2.29(3H, s), 1.40(6H, d) | 350.13 |
| G-8 | 2-Benzyl-7-methoxy-4-(5-methyl-1H-pyrazol-3-ylamino)-2H-phthalazin-1-one | (400MHz, DMSO) 9.46(1H, s), 8.35(1H, d), 7.84(1H, s), 7.55-7.38(5H, m), 6.24(1H, s), 5.35(2H, s), 4.08(3H, s), 5.85(3H, s) | 362.30 |
| G-9 | 2-Isopropyl-6-methoxy-4-(5-methyl-1H-pyrazol-3-ylamino)-2H-phthalazin-1-one | (400MHz, DMSO) 11.97(1H, br s), 9.16(1H, s), 8.24(1H, d), 7.96(1H, s), 7.42(1H, d), 6.39(1H, s), 5.34-5.28(1H, m), 3.98(3H, s), 2.30(3H, s), 1.37(6H, d) | 314.20 |

Method H:

Example H-1

2-Isopropyl-4-(5-methyl-1H-pyrazol-3-ylamino)-7-methylsulfanyl-2H-phthalazin-1-one 7-Mercapto-2-isopropyl-4-bromo-2H-phthalazin-1-one: Concentrated sulfuric acid (5 ml) was added dropwise to a solution of 7-amino-2-isopropyl-4-bromo-2H-phthalazin-1-one (1.5 g, 5.3 mmol) in HOAc (15 ml) and the solution was cooled to 0° C. A solution of NaNO$_2$ (0.5 g, 7.4 mmol) in water (2.5 ml) was added dropwise and the reaction mixture was stirred at 0° C. for 20 min, after which time urea (0.17 g, 2.8 mmol) was added in one portion. The reaction mixture was then added dropwise to a solution of potassium ethyl xanthate (6 g, 37.7 mmol) in water (7.5 ml) and the mixture was heated to 80° C. for 30 min. After this time, the reaction mixture was cooled to RT and DCM (100 ml) was added. The organic layer was separated, dried (MgSO$_4$), filtered and concentrated under vacuum. The residue was taken up in THF (10 ml), NaOH (4.95 g, 0.12 mmol) was added in one portion and the mixture was heated to reflux for 24 hours. The mixture was then cooled to RT and the suspension was acidified to pH 2 with concentrated HCl. DCM (100 ml) was added, the organic layer was separated and was subsequently washed with HCl (1M, 20 ml) and water (20 ml). The organic layer was extracted with NaOH (1M, 200 ml), the aqueous layer was separated and acidified to pH 1 with concentrated HCl. The mixture was extracted with DCM (2×50 ml), the organic layers were combined, dried (MgSO$_4$), filtered and concentrated under vacuum to give the title compound (0.77 g, 48% yield) as a light brown solid which was taken on directly without further purification.

7-Methylsulfanyl-2-isopropyl-4-bromo-2H-phthalazin-1-one: To a solution of 7-mercap-to-2-isopropyl-4-bromo-2H-phthalazin-1-one (0.77 g, 2.6 mmol) in THF (8 ml), was added NaH (60%, 0.13 g, 3.1 mmol) portion-wise. After stirring for 5 min, methyl iodide (0.44 g, 3.1 mmol) was added dropwise and stirring was continued for four hours. The mixture was concentrated under vacuum and the residue was subjected to flash column chromatography (elution: 90% heptane, 10% EtOAc) to give the title compound (0.44 g, 54% yield) as a white solid. $^1$H-NMR: (400 MHz, D$_6$-DMSO), 8.02 (1H, d), 7.88 (1H, d), 7.75 (1 H, d), 5.26-5.15 (1H, m), 2.59 (3H, s), 1.35 (6H, d).

This material was then used in the Buchwald reaction as described in Method A to give the corresponding 2-Isopropyl-4-(5-methyl-1H-pyrazol-3-ylamino)-7-methylsulfanyl-2H-phthalazin-1-one (Example H-1). $^1$H-NMR: (400 MHz, D$_6$-DMSO), 11.92 (1H, s), 9.16 (1H, s), 8.36 (1 H, d), 8.01 (1H, d), 7.75 (1H, d), 6.35 (1H, s), 5.29-5.19 (1H, m), 2.62 (3H, s), 2.25 (2H, s), 1.32 (6H, d) MS (ESI$^+$)=(M+H)$^+$ 330.26.

Example H-2

2-Isopropyl-7-methanesulfonyl-4-(5-methyl-1H-pyrazol-3-ylamino)-2H-phthalazin-1-one 2-Isopropyl-7-methanesulfonyl-4-(5-methyl-1H-pyrazol-3-ylamino)-2H-phthalazin-1-one: Oxone (0.88 g, 1.4 mmol) was added in one portion to a stirred solution of 2-iso-propyl-4-(5-methyl-1H-pyrazol-3-ylamino)-7-methylsulfanyl-2H-phthalazin-1-one (0.12 g, 0.36 mmol) in a 4:1 mixture of dioxane/water (1.2 ml) and the reaction mixture was stirred at RT for one hour. The reaction mixture was diluted with water (5 ml) and the solution was extracted with EtOAc (3×75 ml), the organic layers were combined, dried (MgSO$_4$), filtered and concentrated under vacuum to give a dark brown solid. Flash column chromatography (elution: 96% DCM, 4% MeOH) gave the title compound (0.032 g, 25% yield) as a light yellow solid (Example H-2). $^1$H-NMR: (400 MHz, D$_6$-DMSO) 11.99 (1H, br s), 9.44 (1H, s), 8.76-8.68 (2H, m), 8.39 (1H, d), 6.36 (1H, s), 5.32-5.18 (1H, m), 3.36 (3H, s), 2.25 (3H, s), 1.34 (6H, d) MS (ESI$^+$)=(M+H)$^+$ 362.16.

Using the experimental conditions reported above (Method H, Example H-1 or H-2) and the appropriate starting materials, the following derivatives were prepared:

| Example No. | Systematic name | $^1$H-NMR | MS (ESI+, M + H) |
|---|---|---|---|
| H-3 | 2-Isopropyl-4-(5-methyl-1H-pyrazol-3-yl- | (250MHz, D$_6$-DMSO) 9.15(1H, s), 8.35(1H, d), 8.08(1H, d), 7.79(1H, | 429.16 |

-continued

| Example No. | Systematic name | $^1$H-NMR | MS (ESI+, M + H) |
|---|---|---|---|
| | amino)-7-(2-morpholin-4-yl-ethylsulfanyl)-2H-phthalazin-1-one | dd), 6.34(1H, s), 5.31-5.16(1H, m), 3.61-3.54(4H, m), 3.33-3.24(2H, m), 2.62(2H, t), 2.48-2.40(4H, m), 2.24(3H, s), 1.32(6H, d) | |

Method I:

Example I-1

2-Isopropyl-7-[methyl-(2-morpholin-4-yl-ethyl)-amino]-4-(5-methyl-1H-pyrazol-3-ylamino)-2H-phthalazin-1-one Bromo-3-isopropyl-4-oxo-3,4-dihydro-phthalazin-6-yl)-carbamic acid tert-butyl ester: 7-Amino-2-Isopropyl-4-bromo-2H-phthalazin-1-one (1.88 g, 6.7 mmol) was dissolved in dimethylformamide (DMF) (20 ml). To this was added NaH (60%, 0.8 g, 20.1 mmol) as a suspension in DMF (5 ml). The mixture was stirred at RT for 30 min then di-tert-butyl dicarbonate (Boc$_2$O) (4.36 g, 20.1 mmol) was added in one portion as a solution in DMF (5 ml) and the reaction mixture was heated at 70° C. for 3 hours. After this time, the reaction mixture was cooled to RT and water (20 ml) was added cautiously, the mixture was extracted with EtOAc (3×50 ml), the organic layers were combined, dried (MgSO$_4$), filtered and concentrated under vacuum.

The residue was dissolved in a 1:1 mixture of THF/EtOH (10 ml) and aqueous NaOH (50% by weight solution, 10 ml) was added in one portion, the reaction mixture was stirred vigorously for 30 min. After this time, the mixture was partitioned between water (20 ml) and EtOAc (50 ml). The organic layer was dried (MgSO$_4$), filtered and concentrated to give the title compound (2.2 g, 88% yield) as a light brown solid.

$^1$H-NMR: (400 MHz, D$_6$-DMSO), 8.32 (1H, d), 8.19 (1H, s), 7.88 (1 H, d), 7.41 (1H, s), 5.46-5.31 (1H, m), 1.52 (9H, s), 1.41 (6H, d) MS (ESI$^+$)=(M+H)$^+$ 382.22.

4-Bromo-2-isopropyl-7-methylamino-2H-phthalazin-1-one: Bromo-3-isopropyl-4-oxo-3,4-dihydro-phthalazin-6-yl)-carbamic acid tert-butyl ester (2.2 g, 5.7 mmol) was dissolved in THF (10 ml). To this was added NaH (60%, 0.34 g, 8.6 mmol) as a suspension in THF (5 ml). The mixture was stirred at RT for 30 min then methyl iodide (1.4 ml, 23.0 mmol) was added in one portion as a solution in THF (5 ml) and the reaction mixture was stirred at RT for 3 hours. After this time, the reaction mixture was cooled to RT and water (20 ml) was added cautiously, the mixture was extracted with EtOAc (3×50 ml), the organic layers were combined, dried (MgSO$_4$), filtered and concentrated under vacuum.

The residue was dissolved in a 20% TFA/ DCM solution (10 ml) and the reaction mixture was stirred at RT for 2 hours. After this time, the reaction mixture was concentrated under vacuum to afford a brown oil. Heptane (20 ml) was added, and the mixture was concentrated under vacuum. Diethyl ether (10 ml) was added to the residue and the resulting precipitate was filtered and dried under vacuum to afford the title compound (1.14 g, 68% yield) as a light brown solid MS (ESI$^+$) =(M+H)$^+$ 296.16.

4-Bromo-2-isopropyl-7-[methyl-(2-morpholin-4-yl-ethyl)-amino]-2H-phthalazin-1-one:

4-Bromo-2-isopropyl-7-methylamino-2H-phthalazin-1-one (0.13 g, 0.44 mmol) was dissolved in DMF (5 ml). To this was added NaH (60%, 0.053 g, 1.3 mmol) as a suspension in DMF (2 ml). The mixture was stirred at RT for 30 min then 4-(2-chloro-ethyl)-morpholine (0.12 g, 0.66 mmol) was added in one portion as a solution in DMF (I ml) and the reaction mixture was heated to 70° C. for 24 hours. After this time, the reaction mixture was cooled to RT and water (10 ml) was added cautiously, the mixture was extracted with EtOAc (3×10 ml), the organic layers were combined, dried (MgSO$_4$), filtered and concentrated under vacuum. Flash column chromatography (elution: 95% EtOAc, 5% MeOH) gave the title compound (0.051 g, 30% yield) as a white solid. $^1$H-NMR: (400 MHz, CDCl$_3$), 7.72 (1H, d), 7.49 (1H, s), 7.16 (1 H, d), 5.42-5.29 (1H, m), 3.73-3.67 (4H, m), 3.66-3.59 (2H, t), 3.15 (3H, s), 2.61-2.54 (2H, m), 2.53-2.46 (4H, m), 1.41 (6H, d).

This material was then used in the Buchwald reaction as described in Method A to give the corresponding 2-Isopropyl-7-[methyl-(2-morpholin-4-yl-ethyl)-amino]-4-(5-methyl-1H-pyrazol-3-ylamino)-2H-phthalazin-1-one (example I-1).

Using the experimental conditions reported above (Method I) and the appropriate starting materials, the following derivatives were prepared:

| Example No. | Systematic name | $^1$H-NMR | MS (ESI+, M + H) |
|---|---|---|---|
| I-1 | 2-Isopropyl-7-[methyl-(2-morpholin-4-yl-ethyl)-amino]-4-(5-methyl-1H-pyrazol-3-ylamino)-2H-phthalazin-1-one | (400MHz, D$_6$-DMSO), 11.81(1H, br s), 8.89(1H, br s), 8.19(1H, d), 7.33(1H, d), 7.23(1H, dd), 6.31(1H, s), 5.28-5.19(1H, m), 3.61(2H, t), 3.57-3.53(4H, m), 3.05(3H, s), 2.48-2.45(2H, m), 2.44-2.40(4H, m), 2.22(3H, s), 1.29(6H, d) | 426.24 |
| I-2 | 2-Isopropyl-4-(5-methyl-1H-pyrazol-3-ylamino)-7-(methyl-pyridin-4-ylmethyl-amino)-2H-phthalazin-1-one | (250MHz, CD$_3$OD), 8.46(2H, d), 7.96(1H, d), 7.51(1H, d), 7.34-7.22(4H, m), 6.32(1H, s), 5.43-5.23(1H, m), 4.83(2H, s), 3.28(3H, s), 2.29(3H, s), 1.40(6H, d) | 404.28 |

-continued

| Example No. | Systematic name | ¹H-NMR | MS (ESI+, M + H) |
|---|---|---|---|
| I-3 | 2-Isopropyl-4-(5-methyl-1H-pyrazol-3-ylamino)-7-(methyl-pyridin-3-ylmethyl-amino)-2H-phthalazin-1-one | (400MHz, $D_6$-DMSO), 9.29(1H, br s), 8.73-8.67(2H, m), 8.18(1H, d), 8.10(1H, d), 7.78(1H, dd), 7.41-7.33(2H, m), 6.36(1H, s), 5.27-5.16(1H, m), 4.95(2H, s), 3.24(3H, s), 2.26(3H, s), 1.30(6H, d) | 404.33 |
| I-4 | 2-Isopropyl-4-(5-methyl-1H-pyrazol-3-ylamino)-7-(methyl-pyridin-2-ylmethyl-amino)-2H-phthalazin-1-one | (400MHz, $D_6$-DMSO), 9.24(1H, br s), 8.63(1H, d), 8.15(1H, d), 7.91(1H, t), 7.46-7.40(1H, m), 7.36(1H, d), 7.34-7.28(2H, m), 6.35(1H, s), 5.25-5.15(1H, m), 4.92(2H, s), 3.26(3H, s), 2.26(3H, s), 1.29(6H, d) | 404.32 |
| I-5 | N-[3-Isopropyl-1-(5-methyl-1H-pyrazol-3-ylamino)-4-oxo-3,4-dihydro-phthalazin-6-yl]-N-methyl-acetamide | (400MHz, $D_6$-DMSO), 11.92(1H, s), 9.23(1H, s), 8.48(1H, d), 8.13(1H, d), 7.87(1H, dd), 6.35(1H, s), 5.31-5.16(1H, m), 3.28(3H, s), 2.24(3H, s), 1.94(3H, s), 1.32(6H, d) | 355.33 |
| I-6 | 3-Isopropyl-1-[3-isopropyl-1-(5-methyl-1H-pyrazol-3-yl-amino)-4-oxo-3,4-dihydro-phthalazin-6-yl]-1-methyl-urea | (400MHz, $D_6$-DMSO), 11.88(1H, br s), 9.15(1H, s), 8.36(1H, d), 8.03(1H, d), 7.78(1H, dd), 6.48(1H, d), 6.34(1H, s), 5.32-5.18(1H, m), 3.91-3.76(1H, m), 3.28(3H, s), 2.24(3H, s), 1.32(6H, d), 1.10(6H, d) | 398.34 |
| I-7 | [3-Isopropyl-1-(5-methyl-1H-pyrazol-3-ylamino)-4-oxo-3,4-dihydro-phthalazin-6-yl]-methyl-carbamic acid ethyl ester | (400MHz, $D_6$-DMSO) 12.16-11.60(1H, m), 9.23(1H, s), 8.49(1H, d), 8.23(1H, s), 7.95(1H, d), 6.43(1H, s), 5.48-5.13(1H, m), 4.21(2H, q), 3.42(3H, s), 2.31(3H, s), 1.39(6H, d), 1.27(3H, t) | 385.13 |
| I-8 | N-[3-Isopropyl-1-(5-methyl-1H-pyrazol-3-ylamino)-4-oxo-3,4-dihydro-phthalazin-6-yl]-acetamide | (250MHz, $D_6$-DMSO) 10.50(1H, s), 9.11(1H, s), 8.51(1H, d), 8.37(1H, d), 8.06(1H, dd), 6.34(1H, s), 5.32-5.17(1H, m), 2.25(3H, s), 2.13(3H, s), 1.32(6H, d) | 341.41 |
| I-9 | 7-[(4-Fluoro-benzyl)-methyl-amino]-2-isopropyl-4-(5-methyl-1H-pyrazol-3-ylamino)-2H-phthalazin-1-one | (400MHz, $D_6$-DMSO) 8.99(1H, s), 8.18(1H, d), 7.35(1H, d), 7.28(1H, dd), 7.26-7.20(2H, m), 7.19-7.11(2H, m), 6.32(1H, s), 5.28-5.16(1H, m), 4.76(2H, s), 3.18(3H, s), 2.23(3H, s), 1.29(6H, d) | 421.40 |
| I-10 | N-[3-Isopropyl-1-(5-methyl-1H-pyrazol-3-ylamino)-4-oxo-3,4-dihydro-phthalazin-6-yl]-N-methyl-methanesulfonamide | (400MHz, DMSO) 11.94(1H, br. s.), 9.23(1H, br. s.), 8.48(1H, d), 8.23(1H, d), 7.91(1H, dd), 6.36(1H, s), 5.30-5.21(1H, m), 3.38(3H, s), 3.03(3H, s), 2.25(3H, s), 1.32(6H, d) | 391.35 |
| I-11 | 2-Isopropyl-4-(5-methyl-1H-pyrazol-3-ylamino)-7-(2-morpholin-4-yl-ethylamino)-2H-phthalazin-1-one | (250MHz, $D_6$-DMSO), 9.64(1H, br s), 8.91(1H, s), 8.09(1H, d), 7.27(1H, d), 7.07(1H, d), 6.71(1H, br s), 6.25(1H, s), 5.20-5.13(1H, m), 3.95-3.92(2H, m), 3.29-3.27(4H, m), 3.11-3.08(2H, m), 2.17(3H, s), 1.23(6H, d) | 412.37 |
| I-12 | 2-Isopropyl-7-methylamino-4-(5-methyl-1H-pyrazol-3-ylamino)-2H-phthalazin-1-one | (400MHz, $D_6$-DMSO), 9.04(1H, br s), 8.08(1H, d), 7.19(1H, d), 7.06(1H, dd), 6.33(1H, d), 5.29-5.19(1H, m), 2.80(3H, s), 2.26(3H, s), 1.30(6H, d) | 313.18 |
| I-13 | 1-[3-Isopropyl-1-(5-methyl-1H-pyrazol-3-ylamino)-4-oxo-3,4-dihydro-phthalazin-6-yl]-3-methyl-urea | (400MHz, $D_6$-DMSO), 8.98(1H, s), 8.91(1H, s), 8.06(1H, s), 8.03(1H, s), 7.71(1H, d), 6.12(1H, s), 6.05(1H, s), 5.05-4.97(1H, m), 2.45(3H, s), 2.03(3H, s), 1.10(6H, d) | |
| I-14 | [3-Isopropyl-1-(5-methyl-2H-pyrazol-3-ylamino)-4-oxo-3,4-dihydro-phthalazin-6-yl]-methyl-carbamic acid tert-butyl ester | (250MHz, DMSO), 9.31(1H, br s), 8.37(1H, d), 8.15(1H, d), 7.87(1H, dd), 6.36(1H, s), 5.31-5.15(1H, m), 3.32(3H, s), 2.26(3H, s), 1.44(9H, s), 1.32(6H, d) | 413.18 |

Example I-13 is composed as Example J-1 under Method J.

Method J:

Example J-1

1-[3-Isopropyl-1-(5-methyl-1H-pyrazol-3-ylamino)-4-oxo-3,4-dihydro-phthalazin-6-yl]-3-methyl-urea

1-(1-Bromo-3-isopropyl-4-oxo-3,4-dihydro-phthalazin-6-yl)-3-methyl-urea: 7-Amino-2-Isopropyl-4-bromo-2H-phthalazin-1-one (0.5 g, 1.77 mmol) was dissolved in THF (5 ml). To this was added NaH (60%, 0.14 g, 3.54 mmol) as a suspension in THF (2 ml) and the reaction mixture was stirred for 5 min. After this time methyl isocyanate (0.2 g, 3.55 mmol) was added in one portion and the reaction mixture was stirred at RT for a further 48 hours. After this time, the reaction mixture was partitioned between EtOAc (50 ml) and water (50 ml), the organic layer was separated, dried ($MgSO_4$), filtered and concentrated under vacuum to give the title compound (0.47 g, 78% yield) as a light brown solid.

This material was then used in the Buchwald reaction as described in Method A to give the corresponding 1-[3-Isopropyl-1-(5-methyl-1H-pyrazol-3-ylamino)-4-oxo-3,4-dihydro-phthalazin-6-yl]-3-methyl-urea (example J-1).

Using the experimental conditions reported above (Method J) and the appropriate starting materials, the following derivatives were prepared:

and poured onto ice (1.5 kg) and the resulting precipitate filtered. The solid was washed with water and dried to give the title compound (85 g, 73% yield) as a yellow solid. MS ($ESI^+$)=$(M+H)^+$ 310 & 312

Bromo-4-oxo-3,4-dihydro-phthalazine-6-carboxylic acid ethyl ester: Concentrated sulfuric acid (40 ml) was added to a stirred solution of 1-Bromo-4-oxo-3,4-dihydro-phthalazine-6-carboxylic acid (85 g, 0.32 mol) in EtOH (500 ml) and the mixture was heated to reflux for 48 hours. After this time, the reaction mixture was cooled and the resulting precipitate was filtered. The precipitate was partitioned between EtOAc (1 L) and saturated $NaHCO_3$ (500 ml), the organic layer was separated and washed with water (500 ml) before being dried ($MgSO_4$), filtered and concentrated under vacuum to give the title compound (30 g, 31% yield) as a white solid. MS ($ESI^+$)=$(M+H)^+$ 297 & 299

Bromo-3-isopropyl-4-oxo-3,4-dihydro-phthalazine-6-carboxylic acid ethyl ester: Bromo-4-oxo-3,4-dihydro-phthalazine-6-carboxylic acid ethyl ester (6 g, 0.02 mol) was dissolved in DMF (60 ml). To this was added NaH (60%, 0.97 g, 0.024 mol) as a DMF suspension (5 ml). The mixture was stirred at RT for 30 min then 2-bromo-propanol (3.7 g, 0.03 mol) was added in one portion as a solution in DMF (5 ml). The reaction mixture was stirred for 48 hours whereupon LC-MS showed complete consumption of starting material.

| Example No. | Systematic name | $^1$H-NMR | MS (ESI+, M + H) |
|---|---|---|---|
| J-1 | 1-[3-Isopropyl-1-(5-methyl-1H-pyrazol-3-ylamino)-4-oxo-3,4-dihydro-phthalazin-6-yl]-3-methyl-urea | (400MHz, $D_6$-DMSO), 8.98(1H, s), 8.91(1H, s), 8.04(1H, d), 7.70(1H, dd), 6.12(1H, s), 6.04(1H, s), 5.05-4.97(1H, m), 2.47(3H, d), 2.03(3H, s), 1.09(6H, d) | |
| J-2 | N-[3-Isopropyl-1-(5-methyl-1H-pyrazol-3-ylamino)-4-oxo-3,4-dihydro-phthalazin-6-yl]-methanesulfonamide | (400MHz, $D_6$-DMSO), 10.49(1H, br s), 9.34(1H, s), 8.43(1H, d), 8.11(1H, s), 6.36(1H, s), 5.32-5.19(1H, m), 3.15(3H, s), 2.25(3H, s), 1.33(6H, d) | 377.24 |

Method K:

Example K-1

2-Isopropyl-7-methoxymethyl-4-(5-methyl-1H-pyrazol-3-ylamino)-2H-phthalazin-1-one

1,4-Dioxo-1,2,3,4-tetrahydro-phthalazine-6-carboxylic acid: Hydrazine hydrate (26 g, 0.52 mol) was added in one portion to a stirred mixture of 1,2,4-benzenetricarboxylic anhydride (100 g, 0.52 mol), in HOAc (1.0 L) at RT. The mixture was heated to 120° C. for 2 hours and then allowed to cool to RT. The solid was filtered, washed with water (250 ml) and dried in the vacuum oven at 50° C. for 20 hours to give the title compound (91 g, 85% yield).

Bromo-4-oxo-3,4-dihydro--phthalazine-6-carboxylic acid: 1,4-Dioxo-1,2,3,4-tetrahydrophthalazine-6-carboxylic acid (91.0 g, 0.44 mol) was suspended in DCE (1.0 L) and phosphorus pentabromide (761.0 g, 1.77 mol) was added in three portions and the reaction heated to reflux for 24 hours. The reaction was cooled to RT and poured onto ice (2.50 kg) and the resulting precipitate filtered and washed with water to give the crude product (130 g).

This crude material was suspended in HOAc (1.60 L) and heated to 125° C. for 2 hours. The reaction was cooled to RT The DMF was removed under vacuum and the resulting residue was partitioned between DCM (100 ml) and water (100 ml), the organic layer was dried ($MgSO_4$), filtered and concentrated under vacuum. The resulting yellow oil was recrystallised from MeOH to give the title compound (2.3 g, 34% yield) as a white solid. MS ($ESI^+$)=$(M+H)^+$ 339 & 341

4-Bromo-7-hydroxymethyl-2-isopropyl-2H-phthalazin-1-one: Bromo-3-isopropyl-4-oxo-3,4-dihydro-phthalazine-6-carboxylic acid ethyl ester (2.3 g, 6.8 mmol) was suspended in THF (50 ml) and cooled to 0° C. To the suspension was added $LiBH_4$ (5.1 ml of a 2M solution in THF, 10.2 mmol) dropwise, the suspension was allowed to warm to RT and stirred for 24 hours. After this time, LC-MS showed 50% starting material remained. To this was added $LiBH_4$ (1.7 ml of a 2M solution in THF, 3.4 mmol) and the reaction mixture was stirred for a further 3 hours. The reaction was cooled to 0° C., saturated $NH_4Cl$ (40 ml) was added and the reaction mixture was then partitioned between water (50 ml) and DCM (150 ml). The organic layer was separated, dried ($MgSO_4$), filtered and concentrated under vacuum. The resulting residue was then purified by flash column chromatography (elution: 50% toluene, 30% EtOAc, 20% DCM) to give the title compound (0.9 g, 43% yield) as a white solid. $^1$H-NMR: (400 MHz, $D_6$-DMSO), 8.28 (1H, s), 7.96 (1H, d), 7.88 (1 H, d), 5.64 (1H, t), 5.31-5.18 (1H, m), 4.78 (2H, d), 1.35 (6H, d); MS (ESI+)=(M+H)+ 297 & 299

4-Bromo-2-isopropyl-7-methoxymethyl-2H-phthalazin-1-one: 4-Bromo-7-hydroxymethyl-2-isopropyl-2H-phthalazin-1-one (0.11 g, 0.37 mmol) was dissolved in THF (2 ml). To this was added NaH (60%, 0.019 g, 0.44 mmol) as a THF suspension (2 ml). To this was added methyl iodide (0.063 g, 0.48 mmol) and the reaction mixture was stirred for 20 hours. The reaction mixture was concentrated under vacuum and the residue was purified by flash column chromatography (elution: 80% heptane, 20% EtOAc) to give the title compound (0.08 g, 69% yield) as a white solid.

This material was then used in the Buchwald reaction as described in Method A to give the corresponding 2-Isopropyl-7-methoxymethyl-4-(5-methyl-1H-pyrazol-3-ylamino)-2H-phthalazin-1-one (example K-1).

Using the experimental conditions reported above (Method K) and the appropriate starting materials, the following derivatives were prepared:

mide (TMSBr) (0.9 g, 6.3 mmol) and LiBr (0.41 g, 5 mmol) in MeCN (15 ml). The reaction mixture was heated to 80° C. for 24 hours, after which time the reaction mixture was cooled to RT and the solvent removed under vacuum. The resulting residue was purified by flash column chromatography (elution: 85% heptane, 15% EtOAc) to give the title compound (0.4 g, 44% yield) as a white solid. $^1$H-NMR: (250 MHz, D$_6$-DMSO), 8.37 (1H, s), 8.03 (1H, d), 7.94 (1 H, d), 5.26-5.09 (1H, m), 4.93 (2H, s), 1.35 (6H, d).

4-Bromo-2-isopropyl-7-(4-methyl-piperazin-1-ylmethyl)-2H-phthalazin-1-one: 4-Bromo-7-bromomethyl-2-isopropyl-2H-phthalazin-1-one (0.2 g, 0.56 mmol) was dissolved in THF (1 ml), to this was added N-methyl piperazine (0.14 g, 1.4 mmol) as a solution in THF (1 ml) and the reaction mixture was stirred for 1 hour. Whereupon LC-MS indicated complete consumption of starting material, the solvent was removed under vacuum and the residue was purified by flash

| Example No. | Systematic name | $^1$H-NMR | MS (ESI+, M + H) |
|---|---|---|---|
| K-1 | 2-Isopropyl-7-methoxymethyl-4-(5-methyl-1H-pyrazol-3-ylamino)-2H-phthalazin-1-one | (400MHz, DMSO), 11.88(1H, br s), 9.18(1H, br s), 8.42(1H, d), 8.23(1H, br s), 7.80(1H, d), 6.35(1H, s), 5.30-5.20(1H, m), 4.62(2H, s), 2.24(3H, s), 1.32(6H, d) | 328.31 |
| K-2 | Isopropyl-6-methoxy-methyl-4-(5-methyl-2H-pyrazol-3-yl-amino)-2H-phthalazin-1-one | | 376.30 |
| K-3 | 2-Benzyl-7-methoxy-methyl-4-(5-methyl-1H-pyrazol-3-yl-amino)-2H-phthalazin-1-one | (400MHz, DMSO), 11.93(1H, s), 9.19(1H, s), 8.43(1H, s), 8.27(1H, d), 7.79(1H, d), 6.37(1H, s), 5.30-5.20(1H, m), 4.61(2H, s), 3.37(3H, s), 2.25(3H, s), 1.33(6H, d) | 328.31 |

Method L:

Example L-1

2-Isopropyl-7-(4-methyl-piperazin-1-ylmethyl)-4-(5-methyl-1H-pyrazol-3-ylamino)-2H-phthalazin-1-one 4-Bromo-7-bromomethyl-2-isopropyl-2H-phthalazin-1-one: A solution of 4-bromo-7-hydroxymethyl-2-isopropyl-2H-phthalazin-1-one (0.74 g, 2.5 mmol) in MeCN (5 ml) was added dropwise to a stirred suspension of trimethylsilyl brocolumn chromatography (elution: 90% EtOAC, 10% MeOH) to give the title compound (0.17 g, 84% yield) as a light yellow solid.

This material was then used in the Buchwald reaction as described in Method A to give the corresponding 2-Isopropyl-7-(4-methyl-piperazin-1-ylmethyl)-4-(5-methyl-1H-pyrazol-3-ylamino)-2H-phthalazin-1-one (example L-1).

Using the experimental conditions reported above (Method L) and the appropriate starting materials, the following derivatives were prepared:

| Example No. | Systematic name | $^1$H-NMR | MS (ESI+, M + H) |
|---|---|---|---|
| L-1 | 2-Isopropyl-7-(4-methyl-piperazin-1-yl-methyl)-4-(5-methyl-1H-pyrazol-3-ylamino)-2H-phthalazin-1-one | (250MHz, D$_6$-DMSO), 9.16(1H, br s), 8.40(1H, d), 8.20(1H, d), 7.80(1H, d), 6.36(1H, s), 5.32-5.21(1H, m), 3.65(2H, s), 2.45-2.28(8H, m), 2.25(3H, s), 2.16(3H, s), 1.32(6H, d) | 396.33 |
| L-2 | 2-Isopropyl-4-(5-methyl-1H-pyrazol-3-ylamino)-7-morpholin-4-ylmethyl-2H-phthalazin-1-one | (250MHz, D$_6$-DMSO), 9.20(1H, br s), 8.41(1H, d), 8.23-8.19(1H, m), 7.81(1H, dd), 6.34(1H, s), 5.33-5.17(1H, m), 3.66(2H, s), 3.62-3.54(4H, m), 2.43-2.34(4H, m), 2.24(3H, s), 1.32(6H, d) | 383.31 |

Method M:

Example M-1

3-Isopropyl-1-(5-methyl-1H-pyrazol-3-ylamino)-4-oxo-3,4-dihydro-phthalazine-6-carboxylic acid 3-{tert-Butoxycarbonyl-[6-(tert-butyl-dimethyl-silanyloxymethyl)-3-isopropyl-4-oxo-3,4-dihydro-phthalazin-1-yl]-amino}-5-methyl-pyrazole-1-carboxylic acid tert-butyl ester: 7-(tert-Butyl-dimethyl-silanyloxymethyl)-2-isopropyl-4-(5-methyl-1H-pyrazol-3-ylamino)-2H-phthalazin-1-one (0.68 g, 1.59 mmol) was dissolved in DMF (20 ml). To this was added NaH (60%, 0.22 g, 5.56 mmol) as a suspension in DMF (2 ml). The mixture was stirred at RT for 15 min then di-tert-butyl dicarbonate (Boc$_2$O) (1.05 g, 5.56 mmol) in DMF (2 ml) was added in one portion and the reaction mixture was stirred at RT for 3 hours. After this time, the reaction mixture was concentrated under vacuum and the resulting residue was purified by flash column chromatography (elution: 50% heptane, 50% EtOAc) to give the title compound (0.78 g, 78% yield) as a brown oil. MS (ESI$^+$)=(M+H)$^+$ 628.51.

3-[tert-Butoxycarbonyl-(6-hydroxymethyl-3-isopropyl-4-oxo-3,4-dihydro-phthalazin-1-yl)-amino]-5-methyl-pyrazole-1-carboxylic acid tert-butyl ester: 3-{tert-Butoxycarbonyl-[6-(tert-butyl-dimethyl-silanyloxymethyl)-3-isopropyl-4-oxo-3,4-dihydro-phthalazin-1-yl]-amino}-5-methyl-pyrazole-1-carboxylic acid tert-butyl ester (0.78, 1.25 mmol) was dissolved in THF (3 ml), to this was added a 1M solution of tetrabutylammonium fluoride (TBAF) in THF (1.87 ml, 1.87 mmol) and the mixture was stirred at RT for 24 hours. After this time the reaction mixture was concentrated under vacuum and the residue was purified by flash column chromatography (elution: 50% heptane, 50% EtOAc) to give the title compound (0.39 g, 45% yield) as a brown solid MS (ESI$^+$)=(M+H)$^+$ 514.43.

1-[tert-Butoxycarbonyl-(1-tert-butoxycarbonyl-5-methyl-1H-pyrazol-3-yl)-amino]-3-iso-propyl-4-oxo-3,4-dihydro-phthalazine-6-carboxylic acid: 3-[tert-Butoxycarbonyl-(6-hydroxymethyl-3-isopropyl-4-oxo-3,4-dihydro-phthalazin-1-yl)-amino]-5-methyl-pyrazole-1-carboxylic acid tert-butyl ester (0.2 g, 0.39 mmol) was dissolved in DMSO (3 ml). To this was added 2-iodoxybenzoic acid (IBX) (0.22 g, 0.78 mmol) in one portion and the reaction mixture was stirred at RT for 24 hours. After this time, the reaction mixture was partitioned between EtOAc (20 ml) and water (20 ml), the organic layer was separated and washed with water (3×20 ml) before being dried (MgSO$_4$), filtered and concentrated under vacuum. The resulting orange oil (0.197 g, 0.38 mmol) was dissolved in DCM (3 ml) and water (3 ml). To this was added sulfamic acid (0.037 g, 0.38 mmol) and the reaction mixture was stirred vigorously at 0° C. After 5 min, sodium chlorite (0.034 g, 0.38 mmol) was added in one portion and the mixture stirred for a further hour. After this time, the reaction mixture was diluted with DCM (20 ml) and washed with water (10 ml). The organic layer was separated, dried (MgSO$_4$), filtered and concentrated under vacuum. The resulting residue was purified by flash column chromatography (elution: 50% heptane, 50% EtOAc to 100% EtOAc) to give the title compound (0.088 g, 44% yield) as a white solid. MS (ESI$^+$)=(M+H)$^+$ 528.41.

Isopropyl-1-(5-methyl-1H-pyrazol-3-ylamino)-4-oxo-3,4-dihydro-phthalazine-6-carboxylic acid: 1-[tert-Butoxycarbonyl-(1-tert-butoxycarbonyl-5-methyl-1H-pyrazol-3-yl)-amino]-3-isopropyl-4-oxo-3,4-dihydro-phthalazine-6-carboxylic acid (13.0 mg, 0.02 mmol) was dissolved in a 20% TFA/DCM solution (2 ml) and the reaction mixture was stirred for 48 hours. After this time, the reaction mixture was concentrated and the resulting residue was triturated with diethyl ether to give the title compound (Example M-1) as a white solid. $^1$H-NMR: (400 MHz, D$_6$-DMSO), 9.34(1H, s), 8.73 (1H, s), 8.47 (1H, d), 8.26 (1H, d), 6.28 (1H, s), 5.20-5.17 (1H, m), 2.19 (3H, s), 1.26 (6H, d) MS (ESI$^+$)=(M+H)$^+$ 328.31.

Example M-2

2-Isopropyl-4-(5-methyl-1H-pyrazol-3-ylamino)-7-(morpholine-4-carbonyl)-2H-phthalazin-1-one Isopropyl-4-(5-methyl-1H-pyrazol-3-ylamino)-7-(morpholine-4-carbonyl)-2H-phthalazin-1-one: 1-[tert-Butoxycarbonyl-(1-tert-butoxycarbonyl-5-methyl-1H-pyrazol-3-yl)-amino]-3-isopropyl-4-oxo-3,4-dihydro-phthalazine-6-carboxylic acid (13 mg, 0.025 mmol) was dissolved in DMF (2 ml). To this was added morpholine (6.4 mg, 0.075 mmol) and the reaction mixture was cooled to 0° C., 2-(1H-Benzotriazole-1-yl)-1,1,3,3-tetramethyluronium tetrafluoroborate (TBTU) (15 mg, 0.03 mmol) and TEA (0.014 ml, 0.1 mmol) were added consecutively and the reaction mixture stirred at RT for 24 hours. After this time, the reaction mixture was partitioned between EtOAc (10 ml) and water (10 ml). The organic layer was separated, dried (MgSO$_4$), filtered and concentrated under vacuum. The resulting residue (13.0 mg, 0.02 mmol) was dissolved in a 20% TFA/DCM solution (2 ml) and the reaction mixture was stirred for 48 hours. After this time, the reaction mixture was concentrated and the resulting residue was triturated with diethyl ether to give the corresponding 2-Isopropyl-4-(5-methyl-1H-pyrazol-3-ylamino)-7-(morpholine-4-carbonyl)-2H-phthalazin-1-one (Example M-2). $^1$H-NMR: (400 MHz, D$_6$-DMSO) 9.40 (1H, s), 8.50 (1H, d), 8.23 (1H, s), 7.91 (1H, d), 6.36 (1H, s), 5.28-5.21 (1H, m), 4.12-3.30 (8H, obscured) 2.26 (3H, s), 1.33 (6H, d) MS (ESI$^+$)=(M+H)$^+$ 397.21.

Using the experimental conditions reported above (Method M, Example M-2) and the appropriate starting materials, the following derivatives were prepared:

| Example No. | Systematic name | $^1$H-NMR | MS (ESI+, M + H) |
| --- | --- | --- | --- |
| M-3 | 3-Isopropyl-1-(5-methyl-1H-pyrazol-3-ylamino)-4-oxo-3,4-dihydro-phthalazine-6-carboxylic acid diethylamide | (400MHz, D$_6$-DMSO), 9.46(1H, s), 8.46(1H, d), 8.17(1H, s), 7.88(1H, d), 6.37(1H, s), 5.26-5.23(1H, m), 3.48-3.47(2H, m), 3.18-3.16(2H, m), 2.27(3H, s), 1.34(6H, s), 1.18-1.15(3H, m), 1.08-1.01(3H, m) | 383.16 |
| M-4 | 3-Isopropyl-1-(5-methyl-1H-pyrazol-3-ylamino)-4-oxo-3,4-dihydro-phthalazine-6- | (400MHz, D$_6$-DMSO), 12.16(1H, br s), 9.39(1H, s), 8.66(1H, s), 8.51(1H, d), 8.21(1H, d), 6.36(1H, s), 5.28-5.22(1H, m), 3.75(3H, s), | 357.12 |

-continued

| Example No. | Systematic name | $^1$H-NMR | MS (ESI+, M + H) |
|---|---|---|---|
| | carboxylic acid methoxy-amide | 2.26(3H, s), 1.33(6H, d) | |
| M-5 | 3-Isopropyl-1-(5-methyl-1H-pyrazol-3-ylamino)-4-oxo-3,4-dihydro-phthalazine-6-carboxylic acid isopropylamide | (400MHz, D$_6$-DMSO) 9.43(1H, br. s.), 8.76(1H, d), 8.70(1H, d), 8.49(1H, d), 8.31(1H, dd), 6.38(1H, s), 5.31-5.22(1H, m), 4.21-4.09(1H, m), 2.27(3H, s), 1.34(6H, d), 1.20(6H, d) | 369.37 |
| M-6 | 3-Isopropyl-1-(5-methyl-1H-pyrazol-3-ylamino)-4-oxo-3,4-dihydro-phthalazine-6-carboxylic acid cyclopropylmethyl ester | (400MHz, D$_6$-DMSO) 9.36(1H, s), 8.83(1H, d), 8.60(1H, d), 8.36(1H, dd), 6.35(1H, s), 5.33-5.16(1H, m), 4.21(2H, d), 2.25(3H, s), 1.33(6H, d), 1.25-1.21(1H, m), 0.65-0.56(2H, m), 0.45-0.34(2H, m) | 382.36 |
| M-7 | 7-(4-Acetyl-piperazine-1-carbonyl)-2-isopropyl-4-(5-methyl-1H-pyrazol-3-ylamino)-2H-phthalazin-1-one | (400MHz, D$_6$-DMSO) 9.30(1H, s), 8.51(1H, d), 8.25(1H, d), 7.90(1H, dd), 6.34(1H, s), 5.32-5.16(1H, m), 2.24(3H, s), 2.01(3H, d), 1.32(6H, d) | 438.40 |

Example M-8

3-Isopropyl-1-(5-methyl-1H-pyrazol-3-ylamino)-4-oxo-3,4-dihydro-phthalazine-6-carboxylic acid methyl ester 1-[tert-Butoxycarbonyl-(1-tert-butoxycarbonyl-5-methyl-1H-pyrazol-3-yl)-amino]-3-iso-propyl-4-oxo-3,4-dihydro-phthalazine-6-carboxylic acid (10 mg, 0.019 mmol) (Intermediate of Example M-1) was dissolved in DCM (1 ml). To this was added K$_2$CO$_3$ (3.1 mg, 0.028 mmol) followed by methyl iodide (3.3 mg, 0.028 mmol) and the reaction mixture was stirred at RT for 30 min. After this time the reaction mixture was partitioned between EtOAc (10 ml) and water (1:0 ml). The organic layer was separated, dried (MgSO$_4$), filtered and concentrated under vacuum.

The resulting residue was dissolved in a 20% TFA/DCM solution (2 ml) and the reaction mixture was stirred for 48 hours. After this time, the reaction mixture was concentrated and the resulting residue was triturated with diethyl ether to give the title compound as a white solid. $^1$H-NMR: (400 MHz, D$_6$-DMSO), 12.16 (1H, br s), 9.39 (1H, s), 8.66 (1H, s), 8.51 (1H, d), 8.21 (1H, d), 6.36 (1H, s), 5.28-5.22 (1H, m), 3.75 (3H, s), 2.26 (3H, s), 1.33 (6H, d) MS (ESI$^+$)=(M+H)$^+$ 357.12.

Example M-9

7-Hydroxymethyl-2-isopropyl-4-(5-methyl-1H-pyrazol-3-ylamino)-2H-phthalazin-1-one Bromo-7-hydroxymethyl-2l-isopropyl-2H-phthalazin-1-one (2.0 g, 6.73 mmol) was dissolved in DCM (15 ml). To this was added, TEA (1.4 ml, 10.09 mmol) and DMAP (5 mg). The mixture was stirred at RT for 5 min, after which time a solution of tert-butyldimethylsilyl chloride (TBSCl) (1.22 g, 8.07 mmol) in DCM (5 ml) was added dropwise and the reaction mixture was stirred at RT for 24 hours. The reaction mixture was partitioned between DCM (100 ml) and water (50 ml), the organic layer was separated, dried (MgSO$_4$), filtered and concentrated under vacuum. The resulting residue was purified by flash column chromatography to give 4-Bromo-7-(tert-butyl-dimethyl-silanyloxymethyl)-2-isopropyl-2H-phthalazin-1-one (2.54 g, 92% yield) as a white solid. MS (ESI$^+$)=(M+H)$^+$ 412 & 414

This material was then used in the Buchwald reaction as described in Method A and the residue was dissolved in a 1.1 THF/DCM solution (6 ml). TBAF on silica (0.35 g, 0.35 mmol) was added and the mixture was stirred at RT for 24 hours. After this time the reaction mixture was filtered and the silica washed with DCM (20 ml). The solvent was removed under vacuum to give the corresponding 7-Hydroxymethyl-2-isopropyl-4-(5-methyl-1H-pyrazol-3-ylamino)-2H-phthalazin-1-one (Example M-9). $^1$H-NMR: (400 MHz, D$_6$-DMSO), 9.12 (1H, s), 8.40 (1H, d), 8.26 (1 H, s), 7.79 (1H, d), 6.37 (1H, s), 5.51 (1H, t), 5.30-5.21 (1H, m), 4.69 (2H, d), 2.24 (3H, s), 1.32 (6H, d) MS (ESI$^+$)=(M+H)$^+$ 314.16.

Using the experimental conditions reported above (Method M, Example M-9) and the appropriate starting materials, the following derivatives were prepared:

| Example No. | Systematic name | $^1$H-NMR | MS (ESI+, M + H) |
|---|---|---|---|
| M-10 | 6-Hydroxymethyl-2-isopropyl-4-(5-methyl-1H-pyrazol-3-yl-amino)-2H-phthalazin-1-one | (400MHz, D$_6$-DMSO), 9.44(1H, br s), 8.32(1H, s), 8.26(1H, d), 7.82(1H, d), 6.38(1H, s), 5.29-5.19(1H, m), 4.71(2H, s), 2.28(3H, s), 1.33(6H, d) | 314.24 |

Method N:

Example N-1

3-Isopropyl-1-(5-methyl-1H-pyrazol-3-ylamino)-4-oxo-3,4-dihydro-phthalazine-6-carboxylic acid amide Bromo-3-isopropyl-4-oxo-3,4-dihydro-phthalazine-6-carbonitrile: Concentrated HCl (0.82 ml) was added slowly to a suspension of 7-amino-2-isopropyl-4-bromo-2H-phthalazin-1-one (1.0 g, 3.55 mmol) in water (4 ml). The reaction mixture was cooled to 0° C. and a solution of NaNO$_2$ (0.3 g, 4.30 mmol) in water (1 ml) was added dropwise. The mixture was cooled to −20° C., toluene (4 ml) was added, and the mixture was neutralised with saturated NaHCO$_3$ (5 ml).

At the same time, a solution of KCN (1.5 g, 23.4 mmol) in water (3 ml) was added dropwise to a suspension of Cu(I)Cl in water (4 ml), the mixture was cooled to 0° C. and stirred for 1 hour. After this time, EtOAc (8 ml) was added, followed portionwise by the diazonium species prepared above and, the mixture was stirred for a further hour before being cooled and filtered through celite. The filtrate was washed with water (5 ml), saturated NaHCO$_3$ (5 ml) and brine (5 ml). The organic layer was dried (MgSO$_4$), filtered and concentrated under vacuum. The resulting residue was purified by flash column chromatography (elution: 80% heptane, 20% EtOAc) to give the title compound (0.077 g, 8% yield) as an orange solid. MS (ESI$^+$)=(M+H)$^+$ 292 & 294.

This material was then used in the Buchwald reaction as described in Method A to give the corresponding 3-Isopropyl-1-(5-methyl-1H-pyrazol-3-ylamino)-4-oxo-3,4-dihydro-phthalazine-6-carboxylic acid amide (example N-1).

Example N-1

3-Isopropyl-1-(5-methyl-1H-pyrazol-3-ylamino)-4-oxo-3,4-dihydro-phthalazine-6-carboxylic acid amide $^1$H-NMR: (400 MHz, D$_6$-DMSO), 11.79 (1H, s), 9.12 (1H, s), 8.63 (1 H, s), 8.37 (1H, d), 8.22 (1H, s), 8.16 (1H, d), 7.52 (1H, s), 6.20 (1H, s), 5.21-4.95 (1H, m), 2.10 (3H, s), 1.18 (6H, d); MS (ESI$^+$)=(M+H)$^+$ 327.30.

The mixture was stirred at 5° C. for 30 min then 1-bromo-2methoxyethane (1.67 g, 12 mmol) was added in one portion as a solution in DMF (10 ml). The reaction mixture was stirred for 24 hours at RT, before it was poured into H$_2$O (200 ml). Extraction with EtOAc, subsequent drying of the combined organic phases over Na$_2$SO$_4$, filtration of the solid and stirring of the collected precipitate in diethyl ether:heptane (1:1) gave the title compound (2.4 g, 85% yield) as a white solid. $^1$H-NMR: (400 MHz, D$_6$-DMSO) 8.30 (1H, d), 8.03-8.30 (1H, m), 7.94-7.99 (2H, m), 4.30 (2H, t), 3.71 (2H, t), 3.25 (3H, s).

4-(2-tert-Butyl-5-methyl-2H-pyrazol-3-ylamino)-2-(2-methoxy-ethyl)-2H-phthalazin-1-one (Typical Procedure for Buchwald Reaction): 4-Bromo-2-(2-methoxyethyl)-4-bromo-2H-phthalazin-1-one (0.57 g, 2.0 mmol), 1-(tert-butyl)-3-methyl-1H-pyrazol-5-ylamine (0.46 g, 3.0 mmol), Cs$_2$CO$_3$ (0.98 mg, 3.0 mmol), tris(dibenzylideneacetone)-dipalladium (0) (0.092 g, 0.1 mmol) and 4,5-bis(diphenylphosphino)-9,9-dimethylxanthene (0.17 mg, 0.3 mmol) were dissolved in degassed dioxane (10 ml). The reaction mixture was heated with stirring to 130° C. for 8 hours and then cooled to RT. H$_2$O (100 ml) was added and the precipitated solid was filtered and washed with EtOAc and H$_2$O. The raw product was purified over silica gel (EtOAc:heptane 0%-60% EtOAc) to give the title compound (0.46 g, 65% yield). $^1$H-NMR: (400 MHz, D$_6$-DMSO) 8.22-8.31 (3H, m), 7.95 (1H, t), 7.86 (1H, t), 5.91 (1H, s), 4.05 (1H, t),3.55 (1H, t), 3.17 (3H, s), 2.14 (3H, s), 1.54 (9H, s); MS (ESI$^+$)=356.3 (M+H)$^+$.

2-(2-Methoxyethyl)-4-(5-methyl-2H-pyrazol-3-ylamino)-2H-phthalazin-1-one (Typical procedure for the deprotection of tert-butyl protected pyrazoles): 4-(2-tert-Butyl-5-meth-yl-2H-pyrazol-3-ylamino)-2-(2-methoxy-ethyl)-2H-phthalazin-1-one (0.36 g, 1.0 mmol) was dissolved in formic acid (20 ml) and heated at reflux for 4 h. The resulting raw product was dissolved in H$_2$O and DCM, after evaporation of formic acid. Addition of NaHCO$_3$ resulted in precipitation of a solid, which was collected by filtration. Subsequent washing with H$_2$O, DCM and diethyl ether and drying in vacuum at 40° C. yielded the desired product 2-(2-Methoxyethyl)-4-(5-methyl-2H-pyrazol-3-ylamino)-2H-phthalazin-1-one (example O-1) (0.28 g, 94%). $^1$H-NMR: (400 MHz, D$_6$-DMSO) 9.21 (1H, s), 8.43 (1H, d), 8.29 (1H, d), 8.14 (1H, s), 7.84-7.94 (2H, m), 6.28 (1H, s), 4.23 (2H, t), 3.74 (2H, t), 3.33 (3H, s), 2.23 (3H, s); MS (ESI$^+$)=300.3 (M+H)$^+$ Using the experimental conditions reported above (Method O) and the appropriate starting materials, the following derivatives were prepared:

| Example No. | Systematic name | $^1$H-NMR | MS (API+, M + H$^+$) |
|---|---|---|---|
| O-2 | 2-(2-Methoxy-1-methyl-ethyl)-4-(5-methyl-2H-pyrazol-3-ylamino)-2H-phthalazin-1-one | (400MHz, D$_6$-DMSO) 11.96(1H, s), 9.18(1H, s), 8.43(1H, d), 8.29(1H, d), 7.83-7.91(2H, m), 6.27(1H, s), 5.35(1H, m), 3.76(1H, t), 3.48(1H, m), 3.23(3H, s), 2.25(3H, s), 1.26(3H, d) | 314.1 |

Method O

Example O-1

2-(2-Methoxyethyl)-4-(5-methyl-2H-pyrazol-3-ylamino)-2H-phthalazin-1-one

4-Bromo-2-(2-methoxyethyl)-4-bromo-2H-phthalazin-1-one: 4-Bromo-2H-phthalazin-1-one (see Method E, 2.25 g, 10 mmol) was dissolved in DMF (30 ml). To this was added NaH (60%, 0.27 g, 11 mmol) as a DMF suspension (10 ml).

Example O-3 cis-2-(4-tert-Butyl-cyclohexyl)-4-(5-methyl-2H-pyrazol-3-ylamino)-2H-phthalazin-1-one cis-4-Bromo-2-(4-tert-butyl-cyclohexyl)-2H-phthalazin-1-one: 450 mg 4-Bromo-2H-phthalazin-1-one (see Method E), 469 mg trans-4-tert-butylcyclohexanol and 787 mg triphenylphosphine were dissolved in 50 ml toluene. At 5° C., 1.306 g diethyl azodicarboxylate were added dropwise in 30 min. Stirring was continued for 24 hrs at RT. 50 ml water and 50 ml EtOAc were added and the organic phase separated and washed with water and sodium chloride solution. After drying and evaporating, the residue was chromatographed on silica eluting with a gradient of heptane to heptane /EtOAc 1:1. Yield 435 mg of the title product.

The 4-bromo-phthalazinone obtained above was coupled with 1-(tert-butyl)-3-methyl-1H-pyrazol-5-ylamine and subsequently deprotected by formic acid treatment as described for O-1, to give cis-2-(4-tert-Butyl-cyclohexyl)-4-(5-methyl-2H-pyrazol-3-ylamino)-2H-phthalazin-1-one (example O-3). MS (ESI, M−H) 378.2.

Method P

Example P-1

2-(4-Isopropyl-phenyl)-4-(5-methyl-2H-pyrazol-3-ylamino)-2H-phthalazin-1-one

4-Hydroxy-2-(4-isopropylphenyl)-2H-phthalazin-1-one: 4-Isopropyl phenyl hydrazine hydrochloride (2.77 g, 14.6 mmol) was added in one portion to a stirred mixture of phthalic anhydride (2.0 g, 13 mmol) in HOAc (25 ml) at RT. The reaction mixture was heated to 125° C. for 2 hours, and then allowed to cool to RT. The resultant suspension was poured into $H_2O$ (100 ml), $NaHCO_3$ solution (1M) was added and the resulting solid was removed by filtration. The mother liquor was acidified with conc. HCl. The resulting solid was collected by filtration and dried in vacuum to give the title compound (1.62 g, 45% yield) as a white solid. $^1$H-NMR: (400 MHz, $D_6$-DMSO) 11.80 (1H, s), 8.30 (1H, d), 7.92-8.01 (3H, m), 7.92 (2H, d), 7.35 (2H, d), 2.96 (1H, m), 1.25 (6H, d); MS (ESI$^+$)=345.12 (M+H)$^+$.

4-Bromo-2-(4-isopropylphenyl)-2H-phthalazin-1-one: 4-Hydroxy-2-(4-isopropylphenyl)-2H-phthalazin-1-one (0.10 g, 0.36 mmol), phosphorus oxybromide (0.41 g, 1.4 mmol) and 2,6-di-tert-butyl-4-methylphenol (0.02 g, 0.09 mmol) were stirred at 150° C. for 30 min. $H_2O$ (100 ml) was added after cooling to RT. Extraction with DCM, drying of the combined organic phases over $Na_2SO_4$ and evaporation of the solvent yielded the desired compound (0.05 g, 41%) which was used without any further characterization.

This material was then used in the Buchwald reaction with 1-(tert-butyl)-3-methyl-1H-pyrazol-5-ylamine followed by acid catalyzed deprotection of the tert-butyl group as described in Method O to give the corresponding 2-(4-Isopropyl-phenyl)-4-(5-methyl-2H-pyrazol-3-ylamino)-2H-phthalazin-1-one (example P-1).

2-(4-Isopropyl-phenyl)-4-(5-methyl-2H-pyrazol-3-ylamino)-2H-phthalazin-1-one: Yield (0.004 g, 21%); $^1$H-NMR: (400 MHz, CDCl$_3$/MeOD), 8.50 (1H, d), 8.22 (1H, d), 7.97 (1H, t), 7.91 (1H, t), 7.63 (2H, d), 7.38 (2H, d), 6.25 (1H, s), 3.01 (1H, m), 2.26 (3H, s), 1.28 (6H, d).

Using the experimental conditions reported above (Method P) and the appropriate starting materials, the following derivatives were prepared:

| Example No. | Systematic name | $^1$H-NMR | MS (API+, M + H$^+$) |
|---|---|---|---|
| P-2 | 2-(4-sec-Butyl-phenyl)-4-(5-methyl-2H-pyrazol-3-ylamino)-2H-phthalazin-1-one | (400MHz, D$_6$-DMSO) 9.29(1H, s), 8.50(1H, d), 8.36(1H, d), 7.89-7.98(2H, m), 7.64(2H, d), 7.32(2H, d), 6.22(1H, s), 2.67(1H, m), 2.19(3H, s), 1.62(2H, m), 1.24(3H, d), 0.84(3H, t) | 374.13 |

Method Q-Suzuki Coupling with 2-(iodophenyl)-phthalazinones

Example Q-1

2-Biphenyl-4-yl-4-(5-methyl-1H-pyrazol-3-ylamino)-2H-phthalazin-1-one

4-Hydroxy-2-(4-iodophenyl)-2H-phthalazin-1-one: 4-Iodo phenyl hydrazine (8.97 g, 36.4 mmol) was added in one portion to a stirred mixture of phthalic anhydride (5.0 g, 33 mmol) in HOAc (40 ml) at RT. The reaction mixture was heated to 125° C. for 2 hours, and then allowed to cool to RT. The suspension was poured into $H_2O$ (100 ml) and the resulting solid was removed by filtration. The mother liquor was acidified with conc. HCl. The resulting solid was collected by filtration and dried in vacuum to give the title compound (1.0 g, 8% yield) as a white solid. $^1$H-NMR: (400 MHz, D$_6$-DMSO) 11.91 (1H, br. s), 8.30 (1H, d), 7.91-8.03 (3H, m), 7.83 (2H, d), 7.51 (2H, d); MS (ESI$^+$)=365.0 (M+H)$^+$.

2-Biphenyl-4-yl-4-hydroxy-2H-phtalazin-1-one: 4-Hydroxy-2-(4-iodophenyl)-2H-phthalazin-1-one (0.1 g, 0.3 mmol), phenyl boronic acid (0.04 g, 3 mmol), palladium black (0.02 g, 0.2 mmol) and KF (0.1 g, 18 mmol) were dissolved in MeOH (2 ml) and heated at reflux for 7 h. Removal of supernatant palladium by filtration, extraction with $H_2O$ and subsequent filtration of the precipitated solid yielded the desired title compound (0.07 g, 78% yield) as a white solid. $^1$H-NMR: (400 MHz, D$_6$-DMSO) 11.88 (1H, s), 8.33 (1H, d), 7.89-8.03 (3H, m), 7.78-7.86 (6H, m), 7.50 (2H, t), 7.39 (1H, t),; MS (ESI$^+$)=315.3 (M+H)$^+$.

This material was then brominated with neat phosphorus oxybromide as described in Method R and subsequently used in the Buchwald reaction as described in Method A to give the corresponding 2-Biphenyl-4-yl-4-(5-methyl-1H-pyrazol-3-ylamino)-2H-phthalazin-1-one (example Q-1).

2-Biphenyl-4-yl-4-(5-methyl-1H-pyrazol-3-ylamino)-2H-phthalazin-1-one: Yield (0.03 g, 29%); $^1$H-NMR: (400 MHz, D$_6$-DMSO), 9.36 (1H, s), 8.58 (1H, d), 8.45 (1H, d), 7.95 (3H, m), 7.87-7.92 (6H, m), 7.56 (2H, t), 7.46 (1H, t) 6.35 (1H, s), 2.26 (3H, s); MS (ESI$^+$)=394.6 (M+H)$^+$.

Example Q-2

2-(2'-Methyl-biphenyl-4-yl)-4-(5-methyl-1H-pyrazol-3-ylamino)-2H-phthalazin-1-one 4-(1-tert-Butyl-5-methyl-1H-pyrazol-3-ylamino)-2-(2'-methyl-biphenyl-4-yl)-2H-phtalazin-1-one: 4-Bromo-2-(2'- methyl-biphenyl-4-yl)-2H-phtalazin-1-one (prepared from the appropriate starting materials in analogy to Method Q-1) was coupled with 1-tert-butyl-5-methyl-1H-pyrazol-3-ylamine in a Buchwald reaction as described in Method O to give the title compound (0.049 g, 31% yield). $^1$H-NMR: (400 MHz, D$_6$-DMSO) 8.44 (1H, s), 8.40 (1H, d), 8.33 (1H, d), 8.05 (1 H, t), 7.97 (1H, t), 7.62 (2H, d), 7.40 (2H, d), 7.30 (2H, d), 7.24 (2H, d), 6.00 (1H, s), 2.28 (3H, s), 2.12 (3H, s), 1.57 (9H, s); MS (ESI$^+$)=464.36 (M+H)$^+$.

2-(2'-Methyl-biphenyl-4-yl)-4-(5-methyl-1H-pyrazol-3-ylamino)-2H-phthalazin-1-one: 4-(1-tert-Butyl-5-methyl-1H-pyrazol-3-ylamino)-2-(2'-methyl-biphenyl-4-yl)-2H-phtalazin-1-one was deprotected with formic acid as described in Method O to give the title compound (0.036 g, 83% yield). $^1$H-NMR: (400 MHz, D$_6$-DMSO) 9.29 (1H, s), 8.52 (1H, d), 8.40 (1H, d), 8.17 (1H, s), 7.97 (1H, t), 7.93 (1H, t), 7.82 (2H, d), 7.48 (2H, d), 7.30 (4H, m), 6.29 (1H, s), 2.33 (3H, s), 2.20 (3H, s); MS (ESI$^+$)=408.16 (M+H)$^+$.

Method R-bromination in Neat POBr$_3$

Example R-1

4-(5-Methyl-1H-pyrazol-3-ylamino)-2-(3-trifluoromethyl-phenyl)-2H-phthalazin-1-one 4-Hydroxy-2-(3-trifluoromethylphenyl)-2H-phthalazin-1-one: 4-Hydroxy-2-(3-trifluoro-methylphenyl)-2H-phthalazin-1-one was prepared from 3-trifluoromethyl phenyl hydrazine as described in method B. $^1$H-NMR: (400 MHz, D$_6$-DMSO) 11.95 (1H, s), 8.31 (1H, d), 7.91-8.10 (5H, m), 7.74 (2H, d); MS (ESI$^+$)=307.14 (M+H)$^+$.

4-Bromo-2-(3-trifluoromethylphenyl)-2H-phthalazin-1-one: 4-Hydroxy-2-(3-trifluoro-methylphenyl)-2H-phthalazin-1-one (0.50 g, 1.6 mmol) and phosphorus oxybromide (1.9 g, 6.5 mmol) were stirred at 150° C. for 2 h. H$_2$O (100 ml) was added after cooling to RT. The precipitated solid was collected by filtration and washed with H$_2$O. Drying of the solid in vacuum gave the title compound (0.4 g, 66% yield). $^1$H-NMR: (400 MHz, D$_6$-DMSO) 8.39 (1H, d), 7.95-8.12 (5H, m), 7.79-7.99 (2H, m); MS (ESI$^+$)=370.98 (M+H)$^+$.

This material was then used in the Buchwald reaction as described in Method A to give the corresponding 4-(5-Methyl-1H-pyrazol-3-ylamino)-2-(3-trifluoromethyl-phenyl)-2H-phthalazin-1-one (example R-1).

4-(5-Methyl-1H-pyrazol-3-ylamino)-2-(3-trifluoromethyl-phenyl)-2H-phthalazin-1-one: Yield (0.078 g, 19%); $^1$H-NMR: (400 MHz, D$_6$-DMSO) 11.95 (1H, s), 9.38 (1H, s), 8.53 (1H, d), 8.41 (1H, d), 8.20 (2H, s), 7.98 (2H, t), 7.94 (2H, t), 7.69-7.74 (2H, m), 6.27 (1H, s), 2.19 (3H, s).

Using the experimental conditions reported above (Method R and Buchwald reaction as in method A) and the appropriate starting materials, the following derivatives were prepared:

| Example No. | Systematic name | $^1$H-NMR | MS (API+, M + H$^+$) |
| --- | --- | --- | --- |
| R-2 | 4-(5-Methyl-1H-pyrazol-3-ylamino)-2-(4-phenoxy-phenyl)-2H-phthalazin-1-one | (400MHz, D$_6$-DMSO) 11.95(1H, s), 9.26(1H, s), 8.50(1H, d), 7.98(1H, d), 7.88-7.99(2H, m), 7.73(2H, d), 7.44(2H, t), 7.19(1H, t), 7.11(4H, d), 6.24(1H, s), 2.19(3H, s) | 410.17 |
| R-3 | 4-(5-Methyl-1H-pyrazol-3-ylamino)-2-naphthalen-2-yl-2H-phthalazin-1-one | (400MHz, D$_6$-DMSO) 11.96(1H, s), 9.33(1H, s), 8.55(1H, d), 8.41(1H, d), 8.30(1H, s), 7.87-8.05(6H, m), 7.58(2H, m), 6.31(1H, s), 2.17(3H, s) | 368.3 |
| R-4 | 2-(2-Chloro-phenyl)-4-(5-methyl-1H-pyrazol-3-ylamino)-2H-phthalazin-1-one | (400MHz, D$_6$-DMSO) 11.98(1H, s), 9.27(1H, s), 8.51(1H, d), 8.33(1H, d), 7.99(1H, t), 7.91(1H, t), 7.61-7.68(2H, m), 7.50-7.53(2H, m), 6.06(1H, s), 2.13(3H, s) | 352.3 |

Method S

Example S-1

N-Methyl-4-[4-(5-methyl-1H-pyrazol-3-ylamino)-1-oxo-1H-phthalazin-2-yl]-benzamide 4-(4-Bromo-1-oxo-1H-phthalazin-2-yl)benzoic acid: The title compound was obtained from the appropriate starting materials using the experimental conditions reported above (Method R).Yield (0.65 g, 33%); $^1$H-NMR: (400 MHz, D$_6$-DMSO) 13.10 (1H, s), 8.39 (1H, d), 8.01-8.12 (5H, m), 7.80 (2H, d); MS (ESI$^+$)=345.13 (M+H)$^+$.

4-(4-Bromo-1-oxo-1H-phthalazin-2-yl)-N-methyl-benzamide: 4-(4-Bromo-1-oxo-1H-phthalazin-2-yl)benzoic acid (0.15 g, 0.43 mmol) and 1,1'-carbonyldiimidazol (0.10 g, 0.65 mmol) were dissolved in DMF (10 ml) at RT. Methyl amine (0.33 ml of a 2M solution in THF, 0.65 mmol) were added and stirring was continued for 4 h. Evaporation of the solvent under reduced pressure, dilution with DCM, extraction with a saturated aqueous NaHCO$_3$ solution and evaporation of the solvent in vacuum gave the title compound (0.12 g, 77% yield) $^1$H-NMR: (400 MHz, D$_6$-DMSO) 8.55 (1H, d), 8.38 (1H, d), 8.10 (1H, t), 8.03 (2H, d), 8.02 (2H, d), 7.73 (2H, d), 2.82 (3H, d).

This material was then used in the Buchwald reaction as described in Method A to give the corresponding N-Methyl-4-[4-(5-methyl-1H-pyrazol-3-ylamino)-1-oxo-1H-phthalazin-2-yl]-benzamide (example S-1).

N-Methyl-4-[4-(5-methyl-1H-pyrazol-3-ylamino)-1-oxo-1H-phthalazin-2-yl]-benzamide: Yield (0.005 g, 10%); $^1$H-NMR: (400 MHz, D$_6$-DMSO) 11.95 (1H, s), 9.33 (1H, s), 8.52 (2H, d), 8.50 (1H, d), 7.84-8.03 (6H, m), 6.27 (1H, s), 2.74 (3H, s), 2.20 (3H, s).

Method T

Example T-1

N-{4-[4-(5-Methyl-1H-pyrazol-3-ylamino)-1-oxo-1H-phthalazin-2-yl]-phenyl}-acetamide

2-(4-Amino-phenyl)-4-(5-methyl-1H-pyrazol-3-ylamino)-2H-phthalazin-1-one (C-2, 0.050 g, 0.15 mmol) was dissolved in pyridine (1 ml) at 0° C. Acetylchloride (0.024 ml, 0.33 mmol) was added and stirring was continued for 30 min at 0° C. before the mixture was allowed to warm to RT. The solvent was evaporated after 2 h stirring at RT. The residue was diluted in MeOH (1 ml) and treated with conc. NH$_3$ (1 ml). The title compound was obtained after stirring at RT for 24 h and evaporation of the solvents in vacuum (0.016 g, 29%). $^1$H-NMR: (400 MHz, D$_6$-DMSO) 11.93 (1H, s), 10.08 (1H, s), 9.26 (1H, s), 8.49 (1H, d), 8.36 (1H, d), 7.88-7.98 (2H, m), 7.61-7.69 (4H, m), 6.24 (1H, s), 2.19 (3H, s), 2.08 (3H, s); MS (API$^+$)=375 (M+H)$^+$.

Using the experimental conditions reported above and the appropriate starting materials, the following derivatives were prepared:

Method U

Example U-1

4-(5-Methyl-1H-pyrazol-3-ylamino)-2-(4-phenylamino-phenyl)-2H-phthalazin-1-one

2-(4-Chloro-phenyl)-4-(5-methyl-1H-pyrazol-3-ylamino)-2H-phthalazin-1-one (B-1, 0.10 g, 0.28 mmol), aniline (0.034 g, 0.37 mmol), NaOtBu (0.041 g, 0.43 mmol), tris-(dibenzylideneacetone)-dipalladium (0.026 g, 0.028 mmol) and 2-(di-t-butylphosphino)-biphenyl (0.017 g, 0.057 mmol) under argon were heated to 100° C. for 17 hours, and then allowed to cool to RT. The solvent was evaporated in vacuum, the residue was diluted in H$_2$O (50 ml) and the resulting solid was collected by filtration. Purification of the raw product by chromatography over silica gel with DCM:MeOH (20:1) gave the title compound (0.002 g, 2% yield) as a white solid (example U-1). $^1$H-NMR: (400 MHz, D$_6$-DMSO) 12.0 (1H, s), 9.23 (1H, s), 8.49 (1H, d), 8.33-8.37 (2H, m), 7.88-7.97 (2H, m), 7.54 (2H, d), 7.28 (2H, t), 7.15 (4H, m), 6.86 (1H, t), 6.25 (1H, s), 2.19 (3H, s); MS (API$^+$)=409.0 (M+H)$^+$.

Using the experimental conditions reported above (Method U) and the appropriate starting materials, the following derivatives were prepared:

| Example No. | Systematic name | $^1$H-NMR | MS (API+, M + H$^+$) |
|---|---|---|---|
| T-2 | 2-Methoxy-N-{4-[4-(5-methyl-1H-pyrazol-3-ylamino)-1-oxo-1H-phthalazin-2-yl]-phenyl}-acetamide | (400MHz, D$_6$-DMSO) 11.93(1H, s), 9.90(1H, s), 9.26(1H, s), 8.50(1H, d), 8.36(1H, d), 7.88-7.98(2H, m), 7.77(2H, d), 7.64(2H, d), 6.24(1H, s), 4.04(2H, s), 3.41(3H, s), 2.19(3H, s) | 405.35 |
| T-3 | 2,2-Dimethyl-N-{4-[4-(5-methyl-1H-pyrazol-3-ylamino)-1-oxo-1H-phthalazin-2-yl]-phenyl}-propionamide | (400MHz, D$_6$-DMSO) 9.33(1H, s), 9.27(1H, s), 8.55(1H, d), 8.36(1H, d), 7.87-8.01(2H, m), 7.75(2H, d), 7.63(2H, d), 6.28(1H, s), 2.21(3H, s), 1.26(9H, s) | 417.4 |
| T-4 | N-{4-[4-(5-Methyl-1H-pyrazol-3-ylamino)-1-oxo-1H-phthalazin-2-yl]-phenyl}-benzamide | (400MHz, D$_6$-DMSO) 10.40(1H, d), 9.28(1H, s), 8.53(1H, d), 8.37(1H, t), 7.30-8.10(12H, m), 6.27(1H, s), 2.21(3H, s) | 437.55 |
| T-5 | N-{4-[4-(5-Methyl-1H-pyrazol-3-ylamino)-1-oxo-1H-phthalazin-2-yl]-phenyl}-methanesulfonamide | (400MHz, D$_6$-DMSO) 9.85(1H, d), 9.25(1H, s), 8.50(1H, d), 8.36(1H, d), 7.92-7.99(2H, m), 7.68(2H, d), 7.31(2H, d), 6.23(1H, s), 3.07(3H, s), 2.19(3H, s) | 411.19 |

| Example No. | Systematic name | ¹H-NMR | MS (API+, M + H⁺) |
|---|---|---|---|
| U-2 | 4-(5-Methyl-1H-pyrazol-3-ylamino)-2-(4-morpholin-4-yl-phenyl)-2H-phthalazin-1-one | (400MHz, $D_6$-DMSO) 9.21(1H, s), 8.49(1H, d), 8.35(1H, d), 7.82-7.96(2H, m), 7.55(2H, d), 7.04(2H, d), 6.26(1H, s), 3.77(4H, t), 3.18(4H, t), 2.19(3H, s) | 403.54 |
| U-3 | 4-(5-Methyl-1H-pyrazol-3-ylamino)-2-(4-pyrrolidin-1-yl-phenyl)-2H-phthalazin-1-one | (400MHz, $D_6$-DMSO) 9.21(1H, s), 8.47(1H, d), 8.33(1H, d), 7.82-7.99(2H, m), 7.45(2H, d), 6.61(2H, d), 6.21(1H, s), 3.28(4H, s), 2.17(3H, s), 1.98(4H, s) | 387.54 |

Method V

Example V-1

4-(5-Methyl-2H-pyrazol-3-ylamino)-2-(4-piperidin-1-yl-phenyl)-2H-phthalazin-1-one 4-(2-tert-Butyl-5-methyl-2H-pyrazol-3-ylamino)-2-(4-chloro-phenyl)-2H-phthalazin-1-one: 200 mg 4-Bromo-2-(4-chloro-phenyl)-2H-phthalazin-1-one (prepared as described in Method R), 91 mg 1-tert.-butyl-3-methyl-1H-pyrazol-5-ylamine, 310 mg cesium carbonate, 21 mg 4,5-bis(diphenylphosphino)-9,9-dimethylxanthene and 16.4 mg tris-(di-benzylideneacetone)-dipalladium in 2 ml dry dioxane were stirred under nitrogen at 100° C. for 18 hrs. The solvent was removed under vacuum and the residue stirred with 50 ml water. The crude product was isolated by filtration, washed with water and purified by chromatography on silica, eluting sequentially with heptane, DCM and finally DCM/MeOH 60:1. Yield 180 mg (74%) of the title product.

4-(2-tert-Butyl-5-methyl-2H-pyrazol-3-ylamino)-2-(4-piperidin-1-yl-phenyl)-2H-phthalazin-1-one: 4-(2-tert-Butyl-5-methyl-2H-pyrazol-3-ylamino)-2-(4-chlorophenyl)-2H-phthalazin-1-one (0.10 g, 0.25 mmol), piperidine (0.025 g, 0.29 mmol), NaOtBu (0.033 g, 0.34 mmol), tris-(dibenzylideneacetone)-dipalladium (0.06 g, 0.008 mmol) and 2-(di-t-butylphosphino)-biphenyl (0.004 g, 0.014 mmol) under argon were heated to 100° C. for 19 hours, and then allowed to cool to RT. The solvent was evaporated in vacuum, the residue was diluted in $H_2O$ (30 ml) and the resulting solid was collected by filtration. Purification of the raw product by preparative HPLC gave the title compound (0.014 g, 13% yield). ¹H-NMR: (400 MHz, $D_6$-DMSO) 8.35 (1H, d), superimposed by 8.34 (1H, s), 8.29 (1H, d), 8.01 (1H, t), 7.92 (1H, t), 7.31 (2H, d), 6.92 (2H, d), 5.94 (1H, s), 3.16 (4H, m), 1.61 (4H, m), 1.55 (9H, s), superimposes 1.54 (2H, m); MS (ESI⁺)=457.16 (M+H)⁺.

4-(5-Methyl-2H-pyrazol-3-ylamino)-2-(4-piperidin-1-yl-phenyl)-2H-phthalazin-1-one: 4-(2-tert-Butyl-5-methyl-2H-pyrazol-3-ylamino)-2-(4-piperidin-1-yl-phenyl)-2H-phthalazin-1-one (0.012 g, 0.026 mmol) was dissolved in formic acid (1 ml) and heated at 95° C. for 4 h. The resulting raw product was dissolved in DCM, after evaporation of formic acid. Extraction with a saturated aqueous $NaHCO_3$ solution, combining of the organic phases, evaporation of the solvent in vacuum and purification by chromatography over silica gel with DCM:MeOH (20:1) yielded the title compound (0.006 g, 57%). ¹H-NMR: (400 MHz, $D_6$-DMSO) 11.81 (1H, s), 9.21 (1H, s), 8.48 (1H, d), 8.35 (1H, d), 7.87-7.96 (2H, m), 7.50 (2H, d), 7.01 (2H, d), 6.25 (1H, s), 3.21 (4H, m), 2.19 (3H, s), 1.64 (4H, m), 1.60 (2H, m); MS (ESI⁺)=401.29 (M+H)⁺.

Method W—Buchwald Coupling with Boc-protected Aminopyrazole

Example W-1

2-(2-Chloro-4-trifluoromethyl-phenyl)-4-(5-methyl-1H-pyrazol-3-yl-amino)-2H-phthalazin-1-one 2-(2-Chloro-4-trifluoromethyl-phenyl)-2,3-dihydro-phthalazine-1,4-dione: 1.74 g 2-(2-Chloro-4-trifluoromethyl-phenylamino)-isoindole-1,3-dione (prepared from 2-chloro-4-trifluoromethyl-phenylhydrazine analogously to method A) in 80 ml dry EtOH were treated with 347 mg sodium ethoxide and the mixture was stirred at 85° C. for 2 hrs. After cooling, the mixture was evaporated and dissolved in water. Precipitate was filtered off and washed several times with water. The combined filtrates was acidified by addition of conc. HCl whereupon the product precipitated. It was isolated by filtration and purified by chromatography on silica eluting with a gradient from heptane/EtOAc (50:50) to pure EtOAc. Yield 250 mg (40%)

3-Amino-5-methyl-pyrazole-1-carboxylic acid tert-butyl ester: NaH (95%, 0.57 g, 22.7 mmol) was added slowly to a 0° C. solution of 3-amino-5-methylpyrazole (2.0 g, 20.6 mmol) in THF (40 ml). $Boc_2O$ (4.94 g, 22.7 mmol) was added after 30 min and the mixture was allowed to warm to RT. After stirring for 2 h at RT, the mixture was poured into a saturated aqueous solution of $NaHCO_3$. The aqueous phase was extracted with $CHCl_3$. The combined organic phases were dried over $Na_2SO_4$. Removal of the solvent in vacuum gave a crude mixture of the title compound and its 2-carboxylic acid tert.-butyl ester isomer, which were separated by chromatography on silica in EtOAc/heptane 2:1. Yield 2.4 g, 59%. ¹H-NMR: (400 MHz, $D_6$-DMSO) 5.60 (1H, s), 5.27 (2H, s), 2.34 (3H, s), 1.51 (9H, s); MS (ESI⁺)=198.26 (M+H)⁺.

Typical procedure for the Buchwald reaction with tert-butoxycarbonyl protected pyrazole:

2-(2-Chloro-4-trifluoromethyl-phenyl)-4-(5-methyl-1H-pyrazol-3-ylamino)-2H-phthalazin-1-one: 4-Bromo-2-(2-chloro-4-trifluoromethyl-phenyl)-2H-phthalazin-1-one (obtained from the above phthalazine-1,4-dione by bromination with $POBr_3$ in analogy to Method R, as reported above) (0.15 g, 0.37 mmol), 3-amino-5-methyl-pyrazole-1-carboxylic acid tert-butyl ester (0.080 g, 0.41 mmol), $Cs_2CO_3$ (0.033 g, 0.34 mmol), tris-(dibenzylideneacetone)-dipalladium (0.017 g, 0.019 mmol) and 4,5-bis(diphenylphosphino)-9,9-dimethylxanthene (0.022 g, 0.037 mmol) in 2 ml dry dioxane under nitrogen were heated to 100° C. for 18 hours, and then allowed to cool to RT. H$_2$O was added and the solvent was evaporated in vacuum. The resulting solid was collected by filtration. Purification of the raw product by preparative HPLC gave the title compound (0.069 g, 44% yield). $^1$H-NMR: (400 MHz, D$_6$-DMSO) 11.92 (1H, s), 9.34 (1H, s), 8.54 (1H, d), 8.35 (1H, d), 8.14 (1H, s), 8.01 (1H, t), 7.92 (3H, m), 6.06 (1H, s), 2.14 (3H, s); MS (ESI$^+$)=420.23 (M+H)$^+$.

Analogously, 4-Bromo-2-(4-trifluoromethoxy-phenyl)-2H-phthalazin-1-one, 4-Bromo-2-(4-nitrophenyl)-2H-phthalazin-1-one and 4-Bromo-2-(4-cyclohexyl-phenyl)-2H-phthalazin-1-one (obtained from the corresponding phenyl hydrazines following method R) were coupled with 3-amino-5-methyl-pyrazole-1-carboxylic acid tert-butyl ester to give:

fication of the raw product by chromatography over silica gel gave the title compound (0.015 g, 7% yield). $^1$H-NMR: (400 MHz, D$_6$-DMSO) 12.0 (1H, s), 9.38 (1H, s), 8.67 (2H, d), 8.53 (1H, d), 8.40 (1H, d), 7.91-8.02 (4H, m), 6.31 (1H, s), 2.24 (3H, s); MS (ESI$^+$)=319.2 (M+H)$^+$.

Example X-2

2-(3- tert-Butyl-phenyl)-4-(5-methyl-1H-pyrazol-3-ylamino)-2H-phthalazin-1-one

4-Bromo-2-(3-tert-butylphenyl)-2H-phthalazin-1-one (obtained from the appropriate starting materials in analogy

| Example No. | Systematic name | $^1$H-NMR | MS (API+, M + H$^+$) |
|---|---|---|---|
| W-2 | 4-(5-Methyl-1H-pyrazol-3-ylamino)-2-(4-trifluoromethoxy-phenyl)-2H-phthalazin-1-one | (400MHz, D$_6$-DMSO) 11.97(1H, s), 9.30(1H, s), 8.53(1H, d), 8.38(1H, d), 8.01-7.88(m) and 7.90(d, together 4H), 7.51(2H, d), 6.25(1H, s), 2.20(3H, s). | 402.21 |
| W-3 | 4-(5-Methyl-1H-pyrazol-3-ylamino)-2-(4-nitro-phenyl)-2H-phthalazin-1-one | (400MHz, D$_6$-DMSO), 12.05(1H, s) 9.42(1H, s), 8.54(1H, d), 8.36-8.42(3H, m), 8.15-8.17(2H, m), 7.91-8.02(2H, m), 6.30(1H, s), 2.23(3H, s) | 363.3 |
| W-4 | 2-(4-Cyclohexyl-phenyl)-4-(5-methyl-1H-pyrazol-3-ylamino)-2H-phthalazin-1-one | (400MHz, D$_6$-DMSO), 9.22(1H, s), 8.50(1H, d), 8.35(1H, d), 8.03-7.84(2H, m), 7.62(2H, d), 7.35(2H, d), 6.24(1H, s), 2.59(1H, m), 2.19(3H, s), 1.90-1.78(4H, m), 1.78-1.61(1H, m), 1.55-1.20(5H, m). | 400.20 |

Method X—Buchwald Coupling with Aminopyrazole and 4,5-bis(diphenylphosphino)-9,9-dimethylxanthene (Xantphos)

Example X-1

4-(5-Methyl-1H-pyrazol-3-ylamino)-2-pyridin-4-yl-2H-phthalazin-1-one

4-Bromo-2-pyridin-4-yl-2H-phthalazin-1-one (obtained from the appropriate starting materials in analogy to Method R, as reported above) (0.20 g, 0.66 mmol), 3-amino-5-methyl-pyrazole (0.093 g, 0.93 mmol), Cs$_2$CO$_3$ (0.30 g, 0.93 mmol), tris-(dibenzylideneacetone)-dipalladium (0.030 g, 0.033 mmol) and 4,5-bis(diphenylphosphino)-9,9-dimethylxanthene (Xanthphos) (0.039 g, 0.066 mmol) under nitrogen were heated to 100° C. for 20 hours, and then allowed to cool to RT: H$_2$O was added and the solvent was evaporated in vacuum. The resulting solid was collected by filtration. Purito Method R, as reported above) (0.10 g, 0.28 mmol), 3-amino-5-methyl-pyrazole (0.038 g, 0.39 mmol), Cs$_2$CO$_3$ (0.13 g, 0.39 mmol), tris-(dibenzylidene-acetone)-dipalladium (0.013 g, 0.014 mmol) and 4,5-bis(diphenylphosphino)-9,9-dimethyl-xanthene (0.016 g, 0.028 mmol) under nitrogen were heated to 100° C. for 10 hours, and then allowed to cool to RT. H$_2$O was added and the solvent was evaporated in vacuum. The resulting solid was collected by filtration. Purification of the raw product by chromatography over silica gel gave the title compound (0.020 g, 19% yield). $^1$H-NMR: (400 MHz, D$_6$-DMSO) 9.32 (1H, s), 8.50 (1H, d), 8.38 (1H, d), 7.95 (1H, t), 7.90 (1H, t), 7.78 (1H, s), 7.63 (1H, d), 7.37-7.40 (2H, m), 6.38 (1H, s), 2.18 (3H, s), 1.22 (9H, s); MS (ESI$^+$)=374.27 (M+H)$^+$.

Analogously to the examples described above, 4-Bromo-2-(4-tert-butyl-phenyl)-2H-phthalazin-1-one (obtained as in method R) was coupled with the appropriate amino-pyrazoles to give:

| Example No. | Systematic name | $^1$H-NMR | MS (API+, M + H$^+$) |
|---|---|---|---|
| X-3 | 2-(4-tert-butyl-phenyl)-4-(5-cyclopropyl-1H-pyrazol-3-ylamino)-2H-phthalazin-1-one | (400MHz, D$_6$-DMSO) 11.95(1H, s), 9.23(1H, s), 8.50(1H, d), 8.37(1H, d), 8.03-7.88(2H, m), 7.66(2H, d), 7.50(2H, d), 6.21(1H, s), 1.88(1H, m), 1.35(9H, s), 0.91(2H, m), 0.64(2H, m). | 400.21 |

-continued

| Example No. | Systematic name | $^1$H-NMR | MS (API+, M + H$^+$) |
|---|---|---|---|
| X-4 | 2-(4-tert-Butyl-phenyl)-4-(1H-pyrazol-3-ylamino)-2H-phthalazin-1-one | (400MHz, D$_6$-DMSO), 12.29(1H, s), 9.39(1H, s), 8.54(1H, d), 8.38(1H, d), 7.96(1H, m), 7.91(1H, m), 7.64(3H, m), 7.51(2H, d), 6.53(1H, s), 1.35(9H, s). | 360.19 |

Method Y

Example Y-1

N-Ethyl-N-{4-[4-(5-methyl-1H-pyrazol-3-ylamino)-1-oxo-1H-phthalazin-2-yl]-phenyl}-acetamide 2-(4-Amino-phenyl)-4-bromo-2H-phthalazin-1-one: 4-Bromo-2-(4-nitro-phenyl)-2H-phthalazin-1-one (see Method B) (1.0 g, 2.9 mmol) and PtO$_2$ (0.13 g, 0.58 mmol) were dissolved in EtOAc (40 ml) at RT. The mixture was hydrogenated at ambient pressure for 2 h, before the catalyst was filtered off to yield title compound (0.61 g, 67% yield). $^1$H-NMR: (400 MHz, D$_6$-DMSO) 8.34 (1H, d), 8.07 (1H, t), 7.99 (2H, t), 7.18 (2H, d), 6.63 (2H, d), 5.35 (2H, s); MS (ESI$^+$)=318.42 (M+H)$^+$.

N-[4-(4-Bromo-1-oxo-1H-1phthalazin-2-yl)-phenyl]ac-etamide: Acetyl chloride (0.15 g, 1.90 mmol) was added at RT to a stirred solution of 2-(4-amino-phenyl)-4-bromo-2H-phthalazin-1-one (0.30 g, 0.95 mmol) in pyridine (3 ml). Stirring was continued for 12 h before the solvent was evaporated in vacuum. The resulting raw product was dissolved in H$_2$O and the title compound was collected by filtration (0.22 g, 65% yield). $^1$H-NMR: (400 MHz, D$_6$-DMSO) 10.16 (1H, s), 8.37 (1H, d), 8.08 (1H, t), 8.00-8.03 (2H, m), 7.72 (2H, d), 7.52 (2H, d), 2.05 (3H, s); MS (ESI$^+$)=358.15 (M+H)$^+$.

N-[4-(4-Bromo-1-oxo-1H-phthalazin-2-yl)-phenyl]-N-ethyl-acetamide: NaH (95%, 0.005 g, 0.21 mmol) was added slowly at RT to a solution of N-[4-(4-Bromo-1-oxo-1H-phthalazin-2-yl)-phenyl]acetamide (0.070 g, 0.20 mmol) in DMF (2 ml). Stirring was continued for 1 h before ethyl iodide (0.046 g, 0.29 mmol) was added. Stirring was continued for 12 h before the solvent was evaporated in vacuum. The resulting raw product was purified by chromatography over silica gel with heptane:EtOAc (3:1 up to 1:1) to give the title compound (0.010 g, 14% yield). MS (ESI$^+$)=388.22 (M+H)$^+$.

N-Ethyl-N-{4-[4-(5-methyl-1H-pyrazol-3-ylamino)-1-oxo-1H-phthalazin-2-yl]-phenyl}-acetamide: N-[4-(4-Bromo-1-oxo-1H-phthalazin-2-yl)-phenyl]-N-ethyl-acetamide (0.10 g, 0.027 mmol), 3-amino-5-methyl-pyrazole-1-carboxylic acid tert-butyl ester (0.006 g, 0.03 mmol), Cs$_2$CO$_3$ (0.01 g, 0.03 mmol), tris-(dibenzylideneacetone)-dipalladium (0.001 g, 0.001 mmol) and 4,5-bis(diphenylphosphino)-9,9-dimethylxanthene (0.002 g, 0.003 mmol) under nitrogen were heated to 100° C. for 18 hours, and then allowed to cool to RT. H$_2$O was added and the solvent was evaporated in vacuum. Purification via chromatography gave the title compound (0.003 g, 23% yield). $^1$H-NMR: (400 MHz, D$_6$-DMSO) 9.28 (1H, s), 8.51 (1H, d), 8.38 (1H, d), 7.99 (1H, t), 7.91 (1H, t), 7.87 (2H, d), 7.41 (2H, d), 6.25 (1H, s), 3.69 (2H, q), 2.20 (3H, s), 1.81 (3H, s), 1.07 (3H, t); MS (ESI$^+$)=403.34 (M+H)$^+$.

Analogous to example Y-1,2-(4-amino-phenyl)-4-bromo-2H-phthalazin-1-one was acylated with appropriate chloroformates to yield the corresponding carbamates. These were used directly for coupling with Boc-protected amino-pyrazole under Buchwald conditions as described for Y-1, or were first alkylated and then used for the Buchwald coupling, as described for Y-1. Thus, the following analogs were obtained:

| Example No. | Systematic name | $^1$H-NMR | MS (API+, M + H$^+$) |
|---|---|---|---|
| Y-2 | {4-[4-(5-Methyl-1H-pyrazol-3-ylamino)-1-oxo-1H-phthalazin-2-yl]-phenyl}-carbamic acid ethyl ester | (400MHz, D$_6$-DMSO) 9.76(1H, s), 9.25(1H, s), 8.49(1H, d), 8.36(1H, d), 7.97(1H, t), 7.89(1H, t), 7.58(4H, dd), 6.23(1H, s), 4.16(2H, q), 2.19(3H, s), 1.27(3H, t). | 405.36 |
| Y-3 | methyl-{4-[4-(5-methyl-1H-pyrazol-3-yl-amino)-1-oxo-1H-phthalazin-2-yl]-phenyl}-carbamic acid ethyl ester | (400MHz, D$_6$-DMSO) 11.95(1H, s), 9.22(1H, s), 8.50(1H, d), 8.34(1H, d), 7.98-7.91(2H, m), 7.73(2H, d), 7.43(2H, d), 6.23(1H, s), 4.12(2H, q), 2.20(3H, s), 1.21(3H, t). | 419.30 |
| Y-4 | Methyl-{4-[4-(5-methyl-1H-pyrazol-3-ylamino)-1-oxo-1H-phthalazin-2-yl]-phenyl}-carbamic acid isopropyl ester | (400MHz, D$_6$-DMSO) 9.27(1H, s), 8.52(1H, d), 8.37(1H, d), 7.98-7.90(2H, m), 7.71(2H, d), 7.42(2H, d), 6.28(1H, s), 4.86(1H, m), 2.20(3H, s), 1.21(6H, d). | 433.33 |
| Y-5 | {4-[4-(5-Methyl-1H-pyrazol-3-ylamino)-1-oxo-1H-phthalazin-2-yl]-phenyl}-carbamic acid isopropyl ester | (400MHz, D$_6$-DMSO) 11.92(1H, br s), 9.70(1H, s), 9.26(1H, s), 8.49(1H, d), 8.35(1H, d), 8.01-7.85(2H, m), 7.59(4H, dd), 6.23(1H, s), 4.93(1H, hep), 2.18(3H, s), 1.28(6H, d). | 419.26 |

Method Z:

According to an analogous procedure described under Method ZB, using the appropriate starting material, the following examples can be prepared.

| Example No. | Systematic name | $^1$H-NMR | MS (API+, M + H$^+$) |
|---|---|---|---|
| Z-1 | 6-Amino-4-(5-methyl-1H-pyrazol-3-ylamino)-2-phenyl-2H-phthalazin-1-one | | |

Method ZA—Sulfanyl Substituted 2-phenylphthalazinones from 2-(iodophenyl)phthal-azinones Example ZA-1

2-[4-(2-Methyl-propane-2-sulfonyl)-phenyl]-4-(5-methyl-1H-pyrazol-3-ylamino)-2H-phthalazin-1-one 2-(4-tert-Butylsulfanyl-phenyl)-2,3-dihydro-phthalazine-1,4-dione: 4-Hydroxy-2-(4-iodo-phenyl)-2H-phthalazin-1-one (see Method Q) (0.30 g, 0.8 mmol), sodium 2-methyl-propane-2-thiolate (0.094 g, 0.8 mmol), CuI (0.011 g, 0.06 mmol) and ethylene glycol (0.10 g, 1.6 mmol) were dissolved in N-methyl-pyrrolidinone (NMP) (0.5 ml) under argon and heated to 150° C. Stirring at this temperature was continued for 4 d before the mixture was allowed to warm to RT. H$_2$O (50 ml) was added and the precipitated solid was collected by filtration. The title compound was obtained after purification of the raw product by chromatography over silica gel with DCM (0.21 g, 78%). $^1$H-NMR: (400 MHz, D$_6$-DMSO) 12.35 (1H, s), 8.73 (1H, d), 8.33-8.41 (3H, m), 8.14 (2H, d), 8.01 (2H, d), 1.70 (9H, s); MS (ESI$^+$)=327.14 (M+H)$^+$.

2-[4-(2-Methyl-propane-2-sulfonyl)-phenyl]-2,3-dihydro-phthalazine-1,4-dione: 2-(4-tert-Butylsulfanyl-phenyl)-2,3-dihydro-phthalazine-1,4-dione (0.20 g, 0.61 mmol) and MCPBA (0.28 g, 1.2 mmol) were stirred at RT in DCM (3 ml) for 4 h. The title compound was obtained after evaporation of the solvent in vacuum and subsequent purification of the raw product by chromatography over silica gel with heptane:DCM (1:1 until 0:1) (0.21 g, 98%). $^1$H-NMR: (400 MHz, D$_6$-DMSO) 13.30 (1H, s), 8.34 (1H, d), 7.85-8.12 (3H, m), 7.72 (2H, d), 7.55 (2H, t), 1.28 (9H, s); MS (ESI$^+$)=359.16 (M+H)$^+$.

4-Bromo-2-[4-(2-methyl-propane-2-sulfonyl)-phenyl]-2H-phthalazin-1-one: 2-[4-(2-methyl-propane-2-sulfonyl)-phenyl]-2,3-dihydro-phthalazine-1,4-dione (0.20 g, 0.56 mmol) and phosphorus oxybromide (0.48 g, 1.7 mmol) were stirred at 150° C. for 1 h. H$_2$O (50 ml) was added after cooling to RT. Extraction with DCM, drying of the combined organic phases over Na$_2$SO$_4$, evaporation of the solvent and purification of the raw product by preparative HPLC yielded the desired compound (0.06 g, 18%). $^1$H-NMR: (400 MHz, D$_6$-DMSO) 8.41 (1H, d), 8.07 (1H, d), 8.03-8.10 (4H, m), 7.80 (2H, d), 1.30 (9H, s); MS (API$^+$)=423.0 (M+H)$^+$.

This material was then used in the Buchwald reaction as described in Method A to give the corresponding 2-[4-(2-Methyl-propane-2-sulfonyl)-phenyl]-4-(5-methyl-1H-pyrazol-3-ylamino)-2H-phthalazin-1-one (example ZA-1).

2-[4-(2-Methyl-propane-2-sulfonyl)-phenyl]-4-(5-methyl-1H-pyrazol-3-ylamino)-2H-phthalazin-1-one: Yield (0.003 g, 8%); $^1$H-NMR: (400 MHz, D$_6$-DMSO) 9.40 (1H, s), 8.52 (1H, d), 8.39 (1H, d), 8.13 (2H, d), 7.99 (1H, t), 7.92 (2H, d), superimposes 7.91 (1H, t), 6.29 (1H, s), 1.30 (9H, s); MS (API$^+$)=438.3 (M+H)$^+$.

Example ZA-2

2-(4-Benzenesulfinyl-phenyl)-4-(5-methyl-1H-pyrazol-3-ylamino)-2H-phthalazin-1-one 2-(4-Phenylsulfanyl-phenyl)-2,3-dihydro-phthalazine-1,4-dione: 4-Hydroxy-2-(4-iodo-phenyl)-2H-phthalazin-1-one (see Method Q) (0.20 g, 0.55 mmol), thiophenol (0.061 g, 0.55 mmol), CuI (0.006 g, 0.03 mmol) and ethylene glycol (0.070 g, 1.1 mmol) were dissolved in N-methyl-pyrrolidinone (NMP) (1 ml) under argon and heated to 90° C. Stirring at this temperature was continued for 26 h before the mixture was allowed to warm to RT. H$_2$O (50 ml) was added and the resulting solution was extracted with DCM. The title compound was obtained after purification of the raw product by chromatography over silica gel with DCM (0.10 g, 54%). $^1$H-NMR: (400 MHz, D$_6$-DMSO) 11.91 (1H, s), 8.30 (1H, s), 7.91-8.06 (3H, m), 7.69 (2H, d), 7.34-7.45 (7H, m); MS (ESI$^+$)=347.26 (M+H)$^+$.

4-Bromo-2-(4-phenylsulfanyl-phenyl)-2H-phthalazin-1-one: 2-(4-Phenylsulfanyl-phenyl)-2,3-dihydro-phthalazine-1,4-dione (0.10 g, 0.29 mmol) and phosphorus oxybromide (0.33 g, 12 mmol) were stirred at 150° C. for 40 min. H$_2$O (50 ml) was added after cooling to RT. Extraction with DCM, drying of the combined organic phases over Na$_2$SO$_4$, evaporation of the solvent and purification of the raw product by chromatography over silica gel with heptane:DCM (2:1 to 0:1) gave the desired compound (0.10 g, 86%). $^1$H-NMR: (400 MHz, D$_6$-DMSO) 8.36 (1H, d), 8.11 (1H, d), 8.00 (2H, m), 7.65 (2H, d), 7.44 (7H, m); MS (ESI$^+$)=411.2 (M+H)$^+$.

2-(4-Benzensulfinyl-phenyl)-4-bromo-2H-phthalazin-1-one: 4-Bromo-2-(4-phenylsulfanyl-phenyl)-2H-phthalazin-1-one (0.095 g, 0.23 mmol) and MCPBA (0.052 g, 0.23 mmol) were stirred at RT in DCM (1 ml) for 1 h. The title compound was obtained after evaporation of the solvent in vacuum and subsequent purification of the raw product by chromatography over silica gel with heptane:DCM (1:1 until 0:1) (0.031 g, 31% yield). $^1$H-NMR: (400 MHz, CDCl$_3$) 8.49 (1H, d), 7.80-7.99 (5H, m), 7.76 (2H, d), 7.69 (2H, d), 7.48 (3H, m); MS (ESI$^+$)=427.22 (M+H)$^+$.

This material was then used in the Buchwald reaction as described in Method A to give the corresponding 2-(4-Benzenesulfinyl-phenyl)-4-(5-methyl-1H-pyrazol-3-ylamino)-2H-phthalazin-1-one (example ZA-2).

2-(4-Benzenesulfinyl-phenyl)-4-(5-methyl-1H-pyrazol-3-ylamino)-2H-phthalazin-1-one: Yield (0.003 g, 9%); $^1$H-NMR: (400 MHz, D$_6$-DMSO) 9.31 (1H, s), 8.50 (1H, d), 8.36 (1H, d), 7.89-8.00 (4H, m), 7.83 (2H, d), 7.80 (2H, d), 7.54 (3H, m), 6.22 (1H, s), 2.20 (3H, s); MS (ESI$^+$)=440.33 (M−H)$^+$.

Method ZB: 6- and 7-substituted 2-phenyl-4-pyrazolylamino-phthalazinones

Example ZB-1

N-[3-(4-tert-Butyl-phenyl)-1-(5-methyl-2H-pyrazol-3-ylamino)-4-oxo-3,4-dihydro-phthalazin-6-yl]-formamide 4-Bromo-2-(4-tert-butyl-phenyl)-6-nitro-2H-phthalazin-1-one and 4-bromo-2-(4-tert-butyl-phenyl)-7-nitro-2H-phthalazin-1-one and 4,6-dibromo-2-(4-tert-butyl-phenyl)-2H- phthalazin-1-one: 4-Nitrophthalic anhydride and 4-tert.-butylphenylhydrazine were reacted analogously to method B and gave a 1:1 mixture of 2-(4-tert-butyl-phenyl)-6-nitro-2,3-dihydro-phthalazine-1,4-dione and 2-(4-tert-Butyl-phenyl)-7-nitro-2,3-dihydro-phthalazine-1,4-dione. To 1.60 g of this mixture were added 6.47 g phosphorus oxy-bromide and it was heated to 150 C with stirring. After 1 hr HPLC indicated complete conversion, and the mixture was cooled to RT, diluted with 100 ml water and stirred for 15 min. The crude product was isolated by filtration and purified by chromatography on silica, eluting first with heptane and subsequently with heptane/EtOAc 1:1. The first eluting material was 4,6-dibromo-2-(4-tert-butyl-phenyl)-2H-phthalazin-1-one (121 mg), the second a 1:1 mixture of 4-bromo-2-(4-tert-butyl-phenyl)-6-nitro-2H-phthalazin-1-one and 4-Bromo-2-(4-tert-butyl-phenyl)-7-nitro-2H-phthalazin-1-one (720 mg).

6-Nitro-4-(2-tert-butyl-5-methyl-2H-pyrazol-3-ylamino)-2-(4-tert-butyl-phenyl)-2H-phthalazin-1-one and 7-Nitro-4-(2-tert-butyl-5-methyl-2H-pyrazol-3-ylamino)-2-(4-tert-butyl-phenyl)-2H-phthalazin-1-one: 4.56 g of a 1:1 mixture of 4-Bromo-2-(4-tert-butyl-phenyl)-6-nitro-2H-phthalazin-1-one and 4-Bromo-2-(4-tert-butyl-phenyl)-7-nitro-2H-phthalazin-1-one in 45 ml dry dioxane were reacted with 2.605 g 1-(tert.butyl)-3-methyl-1H-pyrazole-5-ylamine, 5.526 g cesium carbonate, 311 mg tris-(dibenzylideneacetone)-dipalladium and 393 mg 4,5-bis(diphenylphosphino)-9,9-dimethylxanthene under nitrogen at 80 C. After 2 hrs HPLC indicated complete conversion and the mixture was cooled to RT, diluted with 150 ml DCM and washed twice with diluted HCl. The organic phase was dried and evaporated and the residue chromatographed on silica eluting first heptane and subsequently with heptane/EtOAc 8:2. The first eluting product was the 6-nitro isomer (1.82 g), the second eluting product was the 7-nitro isomer (2.05 g).

7-Amino-4-(2-tert-butyl-5-methyl-2H-pyrazol-3-ylamino)-2-(4-tert-butyl-phenyl)-2H-phthalazin-1-one: 2.00 g of 7-Nitro-4-(2-tert-butyl-5-methyl-2H-pyrazol-3-ylamino)-2-(4-tert-butyl-phenyl)-2H-phthalazin-1-one were hydrogenated over palladium on charcoal in MeOH/THF 1:1 at RT. After completion of the reaction the catalyst was filtered off and the filtrate evaporated. The residue was dissolved in 50 ml DCM and extracted three times with a 3:1 mixture of water/conc. HCl. The combined aqueous phases were brought to pH 8 by addition of sodium bicarbonate and extracted with DCM. Removal of the solvent yielded 1.25 g of the title product.

N-[3-(4-tert-Butyl-phenyl)-1-(5-methyl-2H-pyrazol-3-ylamino)-4-oxo-3,4-dihydro-phthalazin-6-yl]-formamide: 15 mg of the above tert.-butyl protected pyrazole were heated in 1 ml formic acid to 90° C. for 6 hrs. Excess formic acid was removed under vacuum and the residue dissolved in DCM and washed with sodium bicarbonate solution. Evaporation of the DCM yielded 12 mg of the title product. $^1$H-NMR: (400 MHz, D$_6$-DMSO) 12.00 (1H, s), 10.77 (1H, s), 9.17 (1H, s), 8.61 (1H, s), 8.50 (2H, m), 8.10 (1H, m), 7.63 (2H, d), 7.51 (2H, d), 6.22 (1H, s), 2.19 (3H, s), 1.35 (9H, s); MS (ESI$^+$)=417.25 (M+H)$^+$.

Example ZB-2

7-Amino-2-(4-tert-butyl-phenyl)-4-(5-methyl-2H-pyrazol-3-ylamino)-2H-phthalazin-1-one 9 mg of N-[3-(4-tert-Butyl-phenyl)-1-(5-methyl-2H-pyrazol-3-ylamino)-4-oxo-3,4-dihydro-phthalazin-6-yl]-formamide (ZB-1) in a mixture of 0.5 ml MeOH and 0.5 ml conc. HCl were stirred at 50° C. for 2 hrs. The mixture was evaporated under vacuum and the residue dissolved in DCM. The DCM solution was washed with sodium bicarbonate solution and evaporated to yield 4 mg of the title product. $^1$H-NMR: (400 MHz, D$_6$-DMSO) 11.8 (1H, br s), 8.81 (1H, s), 8.02 (1H, d), 7.52 (2H, d), 7.40 (2H, d), 7.34 (1H, d), 6.99 (1H, dd), 6.10 (br s, 2H), 2.10 (3H, s), 1.27 (9H, s); MS (ESI$^+$)=389.21 (M+H)$^+$.

Example ZB-3

2-(4-tert-Butyl-phenyl)-4-(5-methyl-2H-pyrazol-3-ylamino)-7-nitro-2H-phthalazin-1-one 15 mg 7-Nitro-4-(2-tert-butyl-5-methyl-2H-pyrazol-3-ylamino)-2-(4-tert-butyl-phenyl)-2H-phthalazin-1-one (preparation see ZB-1) were deprotected by heating in formic acid as described for ZA-1. Evaporation of excess formic acid and chromatography of the residue on silica, eluting with DCM and then with DCM/MeOH 20:1 gave 7 mg of the title product. $^1$H-NMR: (400 MHz, D$_6$-DMSO) 11.9 (1H, br s), 9.53 (1H, br s), 8.98 (1H, s), 8.80 (1H, d), 8.71 (1H, d), 7.65 (2H, d), 7.54 (2H, d), 6.25 (1H, s), 2.20 (3H, s), 1.35 (9H, s); MS (ESI$^+$)=418.31 (M+H)$^+$.

Example ZB-4

2-(4-tert-Butyl-phenyl)-4-(5-methyl-2H-pyrazol-3-ylamino)-6-nitro-2H-phthalazin-1-one 12 mg 6-Nitro-4-(2-tert-butyl-5-methyl-2H-pyrazol-3-ylamino)-2-(4-tert-butyl-phenyl)-2H-phthalazin-1-one (preparation see ZB-1) were deprotected by heating in formic acid as described for ZB-1. Evaporation of excess formic acid and chromatography of the residue on silica, eluting with DCM and then with DCM/MeOH 20:1 gave 5 mg of the title product. $^1$H-NMR: (400 MHz, D$_6$-DMSO) 11.9 (1H, br s), 9.78 (1H, s), 9.52 (1H, s), 8.65-8.56 (2H, m), 7.65 (2H, d), 7.53 (2H, d), 6.26 (1H, s), 2.20 (3H, s), 1.35 (9H, s); MS (ESI$^+$)=418.32 (M+H)$^+$.

Example ZB-5

6-Amino-2-(4-tert-butyl-phenyl)-4-(5-methyl-2H-pyrazol-3-ylamino)-2H-phthalazin-1-one 6-Amino-4-(2-tert-butyl-5-methyl-2H-pyrazol-3-ylamino)-2-(4-tert-butyl-phenyl)-2H-phthalazin-1-one: 1.80 g 6-Nitro-4-(2-tert-butyl-5-methyl-2H-pyrazol-3-ylamino)-2-(4-tert-butyl-phenyl)-2H-phthalazin-1-one (preparation see ZB-1) were hydrogenated as described for the 7-nitro isomer under ZB-1, to give 1.11 g of the 6-aminophthalazinone.

6-Amino-2-(4-tert-butyl-phenyl)-4-(5-methyl-2H-pyrazol-3-ylamino)-2H-phthalazin-1-one: 30 mg 6-amino-4-(2-tert-butyl-5-methyl-2H-pyrazol-3-ylamino)-2-(4-tert-butyl-phenyl)-2H-phthalazin-1-one were dissolved in 0.5 ml MeOH. 2 ml conc. HCl were added and the mixture was heated to 80° C. for 7 hrs. The mixture was evaporated under vacuum, the residue dissolved in DCM and washed with sodium bicarbonate solution. Removal of the DCM yielded 12 mg of the title product. $^1$H-NMR: (400 MHz, D$_6$-DMSO) 11.75 (1H, br s), 8.75 (1H, br s), 8.00 (1H, d), 7.59 (2H, d), 7.46 (2H, d), 7.27 (1H, s), 7.05 (1H, d), 6.16 (br s, 2H), 2.17 (3H, s), 1.33 (9H, s); MS (ESI$^+$)=389.22 (M+H)$^+$.

Example ZB-6

6-Bromo-2-(4-tert-butyl-phenyl)-4-(5-methyl-2H-pyrazol-3-ylamino)-2H-phthalazin-1-one 6-Bromo-4-(2-tert-butyl-5-methyl-2H-pyrazol-3-ylamino)-2-(4-tert-butyl-phenyl)-2H-phthalazin-1-one: 11 mg 4,6-Dibromo-2-(4-tert-butyl-phenyl)-2H-phthalazin-1-one (preparation see ZA-1) were reacted with 39.0 mg 1-tert.-butyl-3-methyl-1H-pyrazol-5-ylamine, 132 mg cesium carbonate, 7.0 mg tris-(dibenzylideneacetone)-dipalladium and 8.8 mg 4,5-bis(diphenylphosphino)-9,9-dimethylxanthene were stirred under argon at 100° C. for 20 hrs until HPLC indicated complete conversion. The solvent was removed under vacuum, the residue was taken up in DCM and washed dilute HCl. Removal of the DCM and chromatography on silica in first heptane and then heptan/EtOAc 8:2 yielded 25 mg of the title product.

6-Bromo-2-(4-tert-butyl-phenyl)-4-(5-methyl-2H-pyrazol-3-ylamino)-2H-phthalazin-1-one: 15 mg of 6-Bromo-4-(2-tert-butyl-5-methyl-2H-pyrazol-3-ylamino)-2-(4-tert-butyl-phenyl)-2H-phthalazin-1-one were heated in formic acid for 5 hrs at 90° C., then evaporated and chromatographed on silica (DCM, then DCM/MeOH 40:1). Yield 10 mg. 1H-NMR: (400 MHz, D$_6$-DMSO) 9.33 (1H, br s), 8.86 (1H, br s), 8.26 (1H, d), 8.80 (1H, d) 7.62 (2H, d), 7.51 (2H, d),.6.26 (1H, s), 2.20 (3H, s), 1.35 (9H, s); MS (ESI$^+$)=452.35 (M+H)$^+$.

Method ZC

Example ZC-1

2-(4-tert-Butyl-2-chloro-phenyl)-4-(5-methyl-1H-pyrazol-3-ylamino)-2H-phthalazin-1-one 4-Bromo-2-(4-tert-butyl-2-chloro-phenyl)-2H--phthalazin-1-one: 54 mg 4-Bromo-2-(4-tert-butyl-phenyl)-2H-phthalazin-1-one (prepared following method R) were dissolved in 5 ml MeOH. At RT chlorine gas was bubbled through the solution for 2 min. Chlorine addition was stopped and the mixture was stirred for 3 days. 29 mg of the title product were isolated by filtration of the resulting suspension. From the filtrate another 11 mg were obtained after evaporation and preparative HPLC/MS chromatography.

2-(4-tert-Butyl-2-chloro-phenyl)-4-(5-methyl-1H-pyrazol-3-ylamino)-2H-phthalazin-1-one: 2-(4-tert-Butyl-2-chloro-phenyl)-4-(5-methyl-1H-pyrazol-3-ylamino)-2H-phthalazin-1-one was obtained by Buchwald reaction of 4-Bromo-2-(4-tert-butyl-2-chloro-phenyl)-2H-phthalazin-1-one with 1-tert.-butyl-3-methyl-1H-pyrazol-5-ylamine and subsequent cleavage of the N-tert.-butyl group as described in method O. $^1$H-NMR: (400 MHz, CDCl$_3$/CD$_3$OD) 8.53 (1H, d), 8.13 (1H, d), 7.94 (1H, t), 7.88 (1H, t) 7.58 (1H, s), 7.46 (2H, s), 6.17 (1H, s), 2.24 (3H, s), 1.39 (9H, s); MS (ESI$^+$)=408.4 (M+H)$^+$.

Example ZD-1

2-Isopropyl-4-(5-methyl-1H-pyrazol-3-ylamino)-7-(2-methylsulfanyl-ethoxy)-2H-phthalazin-1-one 7-Nitro-2,3-dihydro-phthalazine-1,4-dione: Hydrazine hydrate (26.6 g, 0.53 mol) was added in one portion to a stirred mixture of 4-nitrophthalic anhydride (100 g, 0.52 mol), in HOAc (1.0 L) at RT. The mixture was heated to 120° C. for 2 hours and then allowed to cool to RT. The solid was filtered, washed with water (250 ml) and dried under vacuum at 50° C. for 20 hours to give the nitrophthalazinone (95 g, 88% yield). Tr=0.85 min m/z (ES$^+$) (M+H$^+$) 208

6-Nitro-4-bromo-2H-phthalazin-1-one and 7-Nitro-4-bromo-2H-phthalazin-1-one: 7-Nitro-2,3-dihydro-phthalazine-1,4-dione (95.0 g, 0.46 mol) was suspended in DCE (1.0 L) and phosphorus pentabromide (789.0 g, 1.83 mol) was added in three portions and the reaction heated to reflux for 24 hours. The reaction was cooled to RT and poured onto ice (2.5 kg) and the resulting precipitate filtered and washed with water to give the crude product (160.0 g).

This crude material was suspended in HOAc (1.60 L) and heated to 125° C. for 2 hours. The reaction was cooled to RT and poured onto ice (1.5 kg) and the resulting precipitate filtered. The solid was washed with water and dried to give the title compounds (84 g, 68% yield, 1:1 mixture of isomers) as a yellow solid. 7-Nitro: $\delta_H$ (400 MHz, DMSO), 13.29 (1H), 8.83 (1H, d), 8.79 (1H, dd), 8.61 (1H, dd), 8.54 (1H, d), 8.46 (1H, d), 8.16 (d) Tr=1.11 min, m/z (ES$^+$) (M+H)$^+$ 269 & 271

7-Nitro-2-isopropyl-4-bromo-2H-phthalazin-1-one: A mixture of 6-nitro-4-bromo-2H-phthalazin-1-one and 7-nitro-4-bromo-2H-phthalazin-1-one (84 g, 0.31 mol) was dissolved in DMF (400 ml). To this was added NaH (60%, 7.5 g, 0.31 mol) as a DMF suspension (200 ml). The mixture was stirred at RT for 30 min then 2-bromo-propane (7.7 g, 62 mmol) was added in one portion as a solution in DMF (250 ml). The reaction mixture was stirred for 24 hours whereupon LC-MS showed 40% starting material remaining. To this was added NaH (3.75 g, 0.15 mol) and the reaction stirred for a further 24 hours. The DMF was removed under vacuum and the resulting crude material purified by successive column chromatography (elution: 92% heptane, 8% EtOAc) to give the title compound (38.8 g, 40% yield) as a light yellow solid. $\delta_H$ (400 MHz, DMSO), 8.88 (1H, d), 8.87 (1H, dd), 8.16 (1 H, d), 5.19 (1H, m), 1.13 (6H, d).

7-Amino-2-isopropyl-4-bromo-2H-phthalazin-1-one: 7-Nitro-2-isopropyl-4-bromo-2H-phthalazin-1-one (4.6 g, 0.015 mol) was dissolved in a 5:1 mixture of EtOH and water (150 ml). To this solution was added iron powder (2.14 g, 0.039 mol) and concentrated HCl (1 ml), the mixture was heated to 80° C. for 3 hours. After this time, the reaction mixture was cooled to RT and filtered through a pad of celite, the celite was washed with EtOH (100 ml), and the solution was concentrated under vacuum to give the title compound (4.2 g, 98% yield) as a white solid. $\delta_H$ (400 MHz, DMSO), 7.56 (1H, d), 7.28 (1H, s), 7.13 (1 H, d), 6.47 (2H, s), 5.24-5.09 (1H, m), 1.23 (6H, d) Tr=1.34 min m/z (ES$^+$) (M+H)$^+$ 282, 284

7-Hydroxy-2-Isopropyl-4-bromo-2H-phthalazin-1-one: Concentrated sulfuric acid (17 ml) was added slowly to a solution of 7-amino-2-isopropyl-4-bromo-2H-phthalazin-1-one (4.6 g, 0.016 mol) in HOAc (50 ml). The reaction mixture was cooled to 0° C. and a solution of sodium nitrite (1.52 g, 0.022 mol) in water (10 ml) was added dropwise. The reaction mixture was stirred for a further 20 min at 0° C. prior to the addition of urea (0.55 g, 0.009 mol) and cold water (50 ml). The reaction mixture was then added carefully to a refluxing mixture of sulfuric acid (28 ml) in water (115 ml) and the reaction was stirred for a further 10 min at reflux before being allowed to cool to RT. Upon standing, an orange precipitate was observed, which was collected by filtration and washed with water to give the title compound (4.22 g, 93% yield) as an orange powder. $\delta_H$ (400 MHz, DMSO), 11.18 (1H, br s), 7.93 (1H, d), 7.71 (1 H, d), 7.53 (1H, dd), 5.34-5.26 (1H, m), 1.42 (6H, d)

4-Bromo-2-isopropyl-7-(2-methylsulfanyl-ethoxy)-2H-phthalazin-1-one: To a solution of 7-hydroxy-2-isopropyl-4-bromo-2H-phthalazin-1-one (0.8 g, 0.0028 mol) in DMF (8 ml), was added potassium carbonate (2 g, 0.014 mol). After 5 min, 2-chloroethyl methyl sulfide (0.34 g, 0.0028 mol) was added and the solution was heated to 100° C. for 24 hours. After this time LC-MS indicated the complete consumption of starting material and the mixture was cooled, concentrated under vacuum and purified by flash column chromatography (elution: 70% heptane, 30% EtOAc) to give the title compound (0.3 g, 24% yield) as a white solid.

2-Isopropyl-4-(5-methyl-1H-pyrazol-3-ylamino)-7-(2-methylsulfanyl-ethoxy)-2H-phthalazin-1-one (ZD-1): Degassed toluene (6 ml) and EtOH (3 ml) were added in one portion to a mixture of 4-bromo-2-isopropyl-7-(2-methylsulfanyl-ethoxy)-2H-phthalazin-1-one (0.3 g, 0.8 mmol), sodium t-butoxide (0.112 g, 1.2 mmol), 3-amino-5-methyl pyrazole (0.107 g, 1.2 mmol), tris-(dibenzylideneacetone)-dipalladium (0.038 g, 0.042 mmol) and 2-(di-t-butylphosphino)-biphenyl (0.025 g, 0.084 mmol) under nitrogen. The reaction mixture was heated to 100° C. for 20 hours with stirring and then cooled to RT. Diethyl ether (10 ml) was added and the precipitated solid was filtered to give the crude product as a grey solid. Flash column chromatography (elution: 95% EtOAc, 5% MeOH) afforded the title compound as a white solid (0.070 g, 7% yield).

Example ZD-1

2-Isopropyl-4-(5-methyl-1H-pyrazol-3-ylamino)-7-(2-methylsulfanyl-ethoxy)-2H-phthalazin-1-one $\delta_H$ (400 MHz, DMSO) 11.95-11.83 (1H, m), 9.10 (1H, s), 8.39 (1H, d), 7.68 (1H, d), 7.46 (1H, dd), 6.33 (1H, s), 5.29-5.20 (1H, m), 4.33 (2H, t), 2.91 (2H, t), 2.24 (3H, s), 2.18 (3H, s), 1.32 (6H, d) Tr=1.77 min, m/z (ES$^+$) (M+H)$^+$ 374.26.

Example ZD-2

2-Isopropyl-7-(2-methoxy-ethoxy)-4-(5-methyl-1H-pyrazol-3-ylamino)-2H-phthalazin-1-one $\delta_H$ (400 MHz, DMSO) 9.18 (1H, s), 8.36 (1H, d), 7.68 (1H, d), 7.47 (1H, dd), 6.34 (1H, s), 5.30-5.18 (1H, m), 4.28 (2H, t), 3.72 (2H, t), 3.33 (3H, s), 2.25 (3H, s), 1.32 (6H, d) Tr=1.12 min, m/z (ES$^+$) (M+H4)$^+$ 358.39.

Example ZD-3

3-[3-Isopropyl-1-(5-methyl-1H-pyrazol-3-ylamino)-4-oxo-3,4-dihydro-phthalazin-6-yloxy]-propane-1-sulfonic acid dimethylamide $\delta_H$ (400 MHz, DMSO) 11.89 (1H, br s), 9.10 (1H, s), 8.39 (1H, d), 7.68 (1H, d), 7.47 (1H, dd), 6.33 (1H, s), 5.29-5.19 (1H, m), 4.27 (2H, t), 3.27-3.21 (2H, m), 2.80 (6H, s), 2.24 (3H, s), 2.21-2.14 (2H, m), 1.31 (6H, d) Tr=1.23 min, m/z (ES$^+$) (M+H)$^+$ 449.19.

Example ZD-4

2-Isopropyl-4-(5-methyl-1H-pyrazol-3-ylamino)-7-[3-(morpholine-4-sulfonyl)-propoxy]-2H-phthalazin-1-one.

$\delta_H$ (400 MHz, DMSO) 11.88 (1H, br s), 9.10 (1H, s), 8.39 (1H, d), 7.68 (1H, d), 7.47 (1H, dd), 6.33 (1H, s), 5.30-5.18, (1H, m), 4.27 (2H, t), 3.66-3.62 (4H, m), 3.31-3.25 (2H, m), 2.24 (3H, s), 2.22-2.15 (2H, m), 1.32 (6H, d) Tr=1.60 min, m/z (ES$^+$) (M+H)$^+$ 491.22.

Example ZD-5

7-(2-Dimethylamino-ethoxy)-2-isopropyl-4-(5-methyl-1H-pyrazol-3-ylamino)-2H-phthalazin-1-one $\delta_H$ (400 MHz, DMSO) 8.41 (1H, d), 7.67 (1H, d), 7.45 (1H, dd), 6.32 (1H, s), 5.32-5.16 (1H, m), 4.23 (2H, t), 2.68 (2H, t), 2.23 (9H, s), 1.32 (6H, d) Tr=1.38 min, m/z (ES$^+$) (M+H)$^+$ 371.28.

Example ZD-6

2-Isopropyl-7-(2-methanesulfinyl-ethoxy)-4-(5-methyl-1H-pyrazol-3-ylamino)-2H-phthalazin-1-one To a solution of 2-isopropyl-4-(5-methyl-1H-pyrazol-3-ylamino)-7-(2-methylsulfanyl-ethoxy)-2H-phthalazin-1-one (0.077 g, 0.23 mmol) in DCM (2 ml), was added m-chloroperoxybenzoic acid (0.040 g, 0.23 mmol) portion wise. The solution was stirred at RT for 1 hour. After this time LC-MS indicated complete consumption of starting material and the solvent was removed under vacuum. Preparative thin layer chromatography (elution: 50% EtOAc, 50% EtOH) afforded the title compound (0.015 g, 14% yield) as a pale yellow solid.

$\delta_H$ (400 MHz, DMSO) 11.93 (1H, br s), 9.16 (1H, br s), 8.42 (1H, d), 7.72 (1H, d), 7.50 (1H, dd), 6.33 (1H, s), 5.29-5.20 (1H, m), 4.62-4.55 (1H, m), 4.52-4.43 (1H, m), 3.17-3.09 (2H, m), 2.67 (3H, s), 2.23 (3H, s), 1.32 (6H, d) Tr=1.02 min, m/z (ES$^+$) (M+H)$^+$ 390.26.

Example ZD-7

2-Isopropyl-7-(2-methanesulfonyl-ethoxy)-4-(5-methyl-1H-pyrazol-3-ylamino)-2H-phthalazin-1-one To a solution of 2-isopropyl-4-(5-methyl-1H-pyrazol-3-ylamino)-7-(2-methylsulfanyl-ethoxy)-2H-phthalazin-1-one (0.077 g, 0.23 mmol) in DCM (2 ml), was added m-chloroperoxybenzoic acid (0.080 g, 0.46 mmol) portion wise. The solution was stirred at RT overnight. After this time LC-MS indicated complete consumption of starting material and the solvent was removed in vacuo. Preparative thin layer chromatography (elution: 50% EtOAc, 50% EtOH) afforded the title compound (0.010 g, 9% yield) as a white solid.

$\delta_H$ (400 MHz, DMSO) 11.90 (1H, s), 9.12 (1H, s), 8.42 (1H, d), 7.72 (1H, d), 7.53 (1H, dd), 6.35 (1H, s), 5.31-5.16 (1H, m), 4.54 (2H, t), 3.70 (2H, t), 3.11 (3H, s), 2.24 (3H, s), 1.32 (6H, d) Tr=1.59 min, m/z (ES$^+$) (M+H)$^+$ 406.22.

Method ZE:

Example ZE-1

2-Isopropyl-7-[methyl-(2-methylsulfanyl-ethyl)-amino]-4-(5-methyl-1H-pyrazol-3-ylamino)-2H-phtalazin-1-one (1-Bromo-3-isopropyl-4-oxo-3,4-dihydro-phthalazin-6-yl)-carbamic acid tert-butyl ester: 7-Amino-2-isopropyl-4-bromo-2H-phthalazin-1-one (1.88 g, 6.7 mmol) was dissolved in DMF (20 ml). To this was added NaH (60%, 0.8 g, 20.1 mmol) as a suspension in DMF (5 ml). The mixture was stirred at RT for 30 min then Boc$_2$O (4.36 g, 20.1 mmol) was added in one portion as a solution in DMF (5 ml) and the reaction mixture was heated to 70° C. for 3 hours. After this time, the reaction mixture was cooled to RT and water (20 ml) was added cautiously, the mixture was extracted with EtOAc (3×50 ml), the organic layers were combined, dried (MgSO$_4$), filtered and concentrated under vacuum. The residue was dissolved in a 1:1 mixture of THF/EtOH (10 ml) and aqueous NaOH (50% by weight solution, 10 ml) was added in one portion, the reaction mixture was stirred vigorously for 30 min. After this time, the mixture was partitioned between water (20 ml) and EtOAc (50 ml). The organic layer was dried (MgSO$_4$), filtered and concentrated to give the title compound (2.2 g, 88% yield) as a light brown solid. $\delta_H$ (400 MHz, DMSO), 8.32 (1H, d), 8.19 (1H, s), 7.88 (1 H, d), 7.41 (1H, s), 5.46-5.31 (1H, m), 1.52 (9H, s), 1.41 (6H, d) Tr=1.73 min, m/z (ES$^+$) (M+H)$^+$ 382.22.

4-Bromo-2-isopropyl-7-methylamino-2H-phthalazin-1-one: (1-Bromo-3-isopropyl-4-oxo-3,4-dihydro-phthalazin-6-yl)-carbamic acid tert-butyl ester (2.2 g, 5.7 mmol) was dissolved in THF (10 ml). To this was added NaH (60%, 0.34 g, 8.6 mmol) as a suspension in THF (5 ml). The mixture was stirred at RT for 30 min then methyl iodide (1.4 ml, 23.0 mmol) was added in one portion as a solution in THF (5 ml) and the reaction mixture was stirred at RT for 3 hours. After this time, the reaction mixture was cooled to RT and water (20 ml) was added cautiously, the mixture was extracted with EtOAc (3×50 ml), the organic layers were combined, dried (MgSO$_4$), filtered and concentrated under vacuum.

The residue was dissolved in a 20% TFA/DCM solution (10 ml) and the reaction mixture was stirred at RT for 2 hours. After this time, the reaction mixture was concentrated under vacuum to afford a brown oil. Heptane (20 ml) was added, and the mixture was concentrated under vacuum. Ether (10 ml) was added to the residue and the resulting precipitate was filtered and dried under vacuum to afford the title compound (1.14 g, 68% yield) as a light brown solid. Tr=1.50 min, m/z (ES$^+$) (M+H)$^+$ 296.16.

4-Bromo-2-isopropyl-7-[methyl-(2-methylsulfanyl-ethyl)-amino]-2H-phthalazin-1-one: 4-Bromo-2-isopropyl-7-methylamino-2H-phthalazin-1-one (0.095 g, 0.32 mmol) was dissolved in DMF (5 ml). To this was added NaH (60%, 0.015 g, 0.38 mmol) as a suspension in DMF (2 ml). The mixture was stirred at RT for 30 min then chloroethyl methyl sulfide (0.042 g, 0.38 mmol) was added in one portion as a solution in DMF (1 ml) and the reaction mixture was heated to 70° C. for 24 hours. After this time, the reaction mixture was cooled to RT and water (10 ml) was added cautiously, the mixture was extracted with EtOAc (3×10 ml), the organic layers were combined, dried (MgSO$_4$), filtered and concentrated under vacuum. Flash column chromatography (elution: 70% hexane, 30% EtOAc) gave the title compound (0.021 g, 18% yield) as a white solid. $\delta_H$ (400 MHz, CDCl$_3$), 7.73 (1H, d), 7.48 (1H, d), 7.13 (1 H, d), 5.41-5.29 (1H, m), 3.71 (2H, t), 3.18 (3H, s), 3.15 (3H, s), 2.73 (2H, t), 1.41 (6H, d).

This material was then used in the Buchwald reaction as described in Method ZD to give the corresponding 2-Isopropyl-7-[methyl-(2-methylsulfanyl-ethyl)-amino]-4-(5-methyl-1H-pyrazol-3-ylamino)-2H-phtalazin-1-one (B-1).

Example ZE-1

2-Isopropyl-7-[methyl-(2-methylsulfanyl-ethyl)-amino]-4-(5-methyl-1H-pyrazol-3-ylamino)-2H-phtalazin-1-one $\delta_H$ (400 MHz, DMSO), 9.11 (1H, s), 8.19 (1H, d), 7.35 (1H, d), 7.28 (1H, dd), 6.34 (1H, s), 5.29-5.19 (1H, m), 3.71 (2H, t), 3.09 (3H, s), 2.69 (2H, t), 2.25 (3H, s), 2.14 (3H, s), 1.31 (6H, d) Tr=1.80 min, m/z (ES$^+$) (M+H)$^+$ 387.26.

Example ZE-2

2-Isopropyl-7-[(2-methoxy-ethyl)-methyl-amino]-4-(5-methyl-1H-pyrazol-3-ylamino)-2H-phthalazin-1-one $\delta_H$ (400 MHz, DMSO), 11.83 (1H, s), 8.87 (1H, s), 8.21 (1H, d), 7.34 (1H, d), 7.25 (1H, d), 6.34 (1H, s), 5.30-5.18 (1H, m), 3.66 (2H, t), 3.53 (2H, t), 3.25 (3H, s), 3.06 (3H, s), 2.23 (3H, s), 1.30 (6H, d) Tr=1.69 min, m/z (ES$^+$) (M+H)$^+$ 371.32.

Example ZE-3

7-[(2-Dimethylamino-ethyl)-methyl-amino]-2-isopropyl-4-(5-methyl-1H-pyrazol-3-ylamino)-2H-phthalazin-1-one $\delta_H$ (400 MHz, DMSO), 11.83 (1H, br s), 8.90 (1H, br s), 8.21 (1H, d), 7.33 (1H, d), 7.22 (1H, d), 6.33 (1H, br s), 5.29-5.17 (1H, m), 3.61-3.52 (2H, m), 3.05 (3H, t), 2.41 (2H, t), 2.23 (3H, s), 2.20 (6H, s), 1.30 (6H, d) Tr=1.01 min, m/z (ES$^+$) (M+H)$^+$ 384.22.

Method ZF:

Example ZF-1

2-Isopropyl-4-(5-methyl-1H-pyrazol-3-ylamino)-7-(2-methylsulfanyl-ethylsulfanyl)-2H-phthalazin-1-one 7-Mercapto-2-isopropyl-4-bromo-2H-phthalazin-1-one: Concentrated sulfuric acid (5 ml) was added dropwise to a solution of 7-amino-2-isopropyl-4-bromo-2H-phthalazin-1-one (1.5 g, 5.3 mmol) in HOAc (15 ml) and the solution was cooled to 0° C. A solution of sodium nitrite (0.5 g, 7.4 mmol) in water (2.5 ml) was added dropwise and the reaction mixture was stirred at 0° C. for 20 min, after which time urea (0.17 g, 2.8 mmol) was added in one portion. The reaction mixture was then added dropwise to a solution of potassium ethyl xanthate (6 g, 37.7 mmol) in water (7.5 ml) and the mixture was heated to 80° C. for 30 min. After this time, the reaction mixture was cooled to RT and DCM (100 ml) was added. The organic layer was separated, dried (MgSO$_4$), filtered and concentrated under vacuum. The residue was taken up in THF (10 ml), NaOH (4.95 g, 0.12 mmol) was added in one portion and the mixture was heated to reflux for 24 hours. The mixture was then cooled to RT and the suspension was acidified to pH 2 with concentrated HCl. DCM (100 ml) was added, the organic layer was separated and was subsequently washed with HCl (1M, 20 ml) and water (20 ml). The organic layer was extracted with NaOH (1M, 200 ml), the aqueous layer was separated and acidified to pH 1 with concentrated HCl. The mixture was extracted with DCM (2×50 ml), the organic layers were combined, dried (MgSO$_4$), filtered and concentrated under vacuum to give the title compound (0.77 g, 48% yield) as a light brown solid which was taken on directly without further purification.

4-Bromo-2-isopropyl-7-(2-methylsulfanyl-ethylsulfanyl)-2H-phthalazin-1-one: To a solution of crude 7-mercapto-2-isopropyl-4-bromo-2H-phthalazin-1-one (0.40 g, 1.3 mmol) in DMF (8 ml), was added NaH (60%, 0.064 g, 1.6 mmol) portion-wise. After stirring for 5 min, chloroethyl methylsulfide (0.17 g, 1.6 mmol) was added dropwise. The mixture was heated to 60° C. for two hours, after which time the mixture was concentrated under vacuum and the residue was subjected to flash column chromatography (elution: 90% heptane, 10% EtOAc) to give the title compound (0.44 g, 54% yield) as a white solid. $\delta_H$ (400 MHz, DMSO), 8.03 (1H, d), 7.92 (1H, d), 7.81 (1 H, d), 5.26-5.15 (1H, m), 3.41 (2H, t), 2.78 (2H, t), 2.15 (3H, s), 1.36 (6H, d).

This material was then used in the Buchwald reaction as described in Method ZD to give the corresponding 2-isopropyl-4-(5-methyl-1H-pyrazol-3-ylamino)-7-(2-methylsulfanyl-ethylsulfanyl)-2H-phthalazin-1-one (ZF-1).

Example ZF-1

2-Isopropyl-4-(5-methyl-1H-pyrazol-3-ylamino)-7-(2-methylsulfanyl-ethylsulfanyl)-2H-phthalazin-1-one Tr=1.33 min, m/z (ES+) (M+H)+ 390.23.

Example ZF-2

2-Isopropyl-7-(2-methanesulfonyl-ethanesulfonyl)-4-(5-methyl-1H-pyrazol-3-ylamino)-2H-phthalazin-1-one Oxone (0.12 g, 0.07 mmol) was added in one portion to a stirred solution of 2-isopropyl-4-(5-methyl-1H-pyrazol-3-ylamino)-7-(2-methylsulfanyl-ethylsulfanyl)-2H-phthalazin-1-one (0.013 g, 0.03 mmol) in a 4:1 mixture of dioxane/water (1.2 ml) and the reaction mixture was stirred at RT for 1 hour. The reaction mixture was diluted with water (5 ml) and the solution was extracted with EtOAc (3×75 ml), the organic layers were combined, dried (MgSO$_4$), filtered and concentrated under vacuum to give the title compound (0.008 g, 57% yield) as a white solid. $\delta_H$ (400 MHz, DMSO) 9.69 (1H, br s), 8.75 (1H, d), 8.71 (1H, d), 8.47 (1H, dd), 6.40 (1H, s), 5.31-5.22 (1H, m), 3.95-3.89 (2H, m), 3.48-3.42 (2H, m), 3.06 (3H, s), 2.29 (3H, s), 1.36 (6H, d) Tr=1.61 min, m/z (ES+) (M+H)+ 454.10.

Method ZG:

Example ZG-1

7-(2-Dimethylamino-ethoxy)-2-isopropyl-4-(5-methyl-1H-pyrazol-3-ylamino)-2H-phthalazin-1-one (1-Bromo-3-isopropyl-4-oxo-3,4-dihydro-phthalazin-6-yl)-carbamic acid tert-butyl ester: 7-Amino-2-isopropyl-4-bromo-2H-phthalazin-1-one (1.88 g, 6.7 mmol) was dissolved in DMF (20 ml). To this was added NaH (60%, 0.8 g, 20.1 mmol) as a suspension in DMF (5 ml). The mixture was stirred at RT for 30 min then Boc$_2$O (4.36 g, 20.1 mmol) was added in one portion as a solution in DMF (5 ml) and the reaction mixture was heated to 70° C. for 3 hours. After this time, the reaction mixture was cooled to RT and water (20 ml) was added cautiously, the mixture was extracted with EtOAc (3×50 ml), the organic layers were combined, dried (MgSO$_4$), filtered and concentrated under vacuum. The residue was dissolved in a 1:1 mixture of THF/EtOH (10 ml) and aqueous NaOH (50% by weight solution, 10 ml) was added in one portion, the reaction mixture was stirred vigorously for 30 min. After this time, the mixture was partitioned between water (20 ml) and EtOH (50 ml). The organic layer was dried (MgSO$_4$), filtered and concentrated to give the title compound (2.2 g, 88% yield) as a light brown solid. $\delta_H$ (400 MHz, DMSO), 8.32 (1H, d), 8.19 (1H, s), 7.88 (1 H, d), 7.41 (1H, s), 5.46-5.31 (1H, m), 1.52 (9H, s), 1.41 (6H, d) Tr=1.73 min, m/z (ES+) (M+H)+ 382.22.

7-(2-Dimethylamino-ethoxy)-2-isopropyl-4-(5-methyl-1H-pyrazol-3-ylamino)-2H-phthalazin-1-one: (1-Bromo-3-isopropyl-4-oxo-3,4-dihydro-phthalazin-6-yl)-carbamic acid tert-butyl ester (0.75 g, 1.96 mmol) was dissolved in DMF (10 ml). To this was added NaH (60%, 0.2 g, 4.9 mmol) as a suspension in DMF (5 ml). The mixture was stirred at RT for 30 min then 1-bromo-2-methoxyethane (0.4 g, 2.9 mmol) was added in one portion as a solution in DMF (5 ml) and the reaction mixture was stirred at RT for 3 hours. After this time, the reaction mixture was cooled to RT and water (20 ml) was added cautiously, the mixture was extracted with EtOAc (3×50 ml), the organic layers were combined, dried (MgSO$_4$), filtered, concentrated under vacuum and the residue subjected to flash column chromatography (elution: 60% heptane, 40% EtOAc) to afford (1-bromo-3-isopropyl-4-oxo-3,4-dihydro-phthalazin-6-yl)-(2-dimethylamino-ethyl)-carbamic acid tert-butyl ester (0.2 g, 23% yield) as a white solid.

This material was then used in the Buchwald reaction as described in Method ZD to give the corresponding 2-isopropyl-7-[methyl-(2-methylsulfanyl-ethyl)-amino]-4-(5-methyl-1H-pyrazol-3-ylamino)-2H-phthalazin-1-one.

The residue was dissolved in a 20% TFA/DCM solution (5 ml) and the reaction mixture was stirred at RT for 2 hours. After this time, the reaction mixture was concentrated under vacuum to afford a brown oil. Heptane (2 ml) was added, and the mixture was concentrated under vacuum. Ether (1 ml) was added to the residue and the resulting precipitate was filtered and dried under vacuum to afford the title compound (0.061 g, 6% yield) as a pale yellow solid.

Example ZG-1

7-(2-Dimethylamino-ethoxy)-2-isopropyl-4-(5-methyl-1H-pyrazol-3-ylamino)-2H-phthalazin-1-one $\delta_H$ (400 MHz, DMSO), 9.41 (1H, br s), 8.95 (1H, s), 8.18 (1H, d), 7.35 (1H, d), 7.14 (1H, dd), 6.33 (1H, s), 5.29-5.17 (1H, m), 3.60-3.53 (2H, m), 3.33-3.26 (2H, m), 2.88-2.84 (6H, m), 2.24 (3H, s), 1.31 (6H, d) Tr=1.50 min, m/z (ES+) (M+H)+ 370.38.

Method ZH:

Example ZH-1

7-Cyclopropylmethoxymethyl-2-isopropyl-4-(5-methyl-1H-pyrazol-3-yl-amino)-2H-phthalazin-1-one 1,4-Dioxo-1,2,3,4-tetrahydro-phthalazine-6-carboxylic acid: Hydrazine hydrate (26 g, 0.52 mol) was added in one portion to a stirred mixture of 1,2,4-benzenetricarboxylic anhydride (100 g, 0.52 mol), in HOAc (1.0 L) at RT. The mixture was heated to 120° C. for 2 h and then allowed to cool to RT. The solid was filtered, washed with water (250 ml) and dried in the under vacuum at 50° C. for 20 hours to give the title compound (91 g, 85% yield).

1-Bromo-4-oxo-3,4-dihydro-phthalazine-6-carboxylic acid: 1,4-Dioxo-1,2,3,4-tetrahydro-phthalazine-6-carboxylic acid (91.0 g, 0.44 mol) was suspended in DCE (1.0 L) and phosphorus pentabromide (761.0 g, 1.77 mol) was added in three portions and the reaction heated to reflux for 24 hours. The reaction was cooled to RT and poured onto ice (2.5 kg)

and the resulting precipitate filtered and washed with water to give the crude product (130.0 g). This crude material was suspended in HOAc (1.6 L) and heated to 125° C. for 2 h. The reaction was cooled to RT and poured onto ice (1.5 kg) and the resulting precipitate filtered. The solid was washed with water and dried to give the title compound (85 g, 73% yield) as a yellow solid. Tr=0.94 min, m/z (ES$^+$) (M+H)$^+$ 310 & 312

1-Bromo-4-oxo-3,4-dihydro-phthalazine-6-carboxylic acid ethyl ester: Concentrated sulfuric acid (40 ml) was added to a stirred solution of 1-bromo-4-oxo-3,4-dihydro-phthalazine-6-carboxylic acid (85 g, 0.32 mol) in EtOH (500 ml) and the mixture was heated to reflux for 48 hours. After this time, the reaction mixture was cooled and the resulting precipitate was filtered. The precipitate was partitioned between EtOAc (1 L) and saturated NaHCO$_3$ (500 ml), the organic layer was separated and washed with water (500 ml) before being dried (MgSO$_4$), filtered and concentrated under vacuum to give the title compound (30 g, 31% yield) as a white solid. Tr=1.23 min, m/z (ES$^+$) (M+H)$^+$ 297 & 299

1-Bromo-3-isopropyl-4-oxo-3,4-dihydro-phthalazine-6-carboxylic acid ethyl ester: 1-bromo-4-oxo-3,4-dihydro-phthalazine-6-carboxylic acid ethyl ester (6 g, 0.02 mol) was dissolved in DMF (60 ml). To this was added NaH (60%, 0.97 g, 0.024 mol) as a DMF suspension (5 ml). The mixture was stirred at RT for 30 min then 2-bromo-propanol (3.7 g, 0.03 mol) was added in one portion as a solution in DMF (5 ml). The reaction mixture was stirred for 48 hours whereupon LC-MS showed complete consumption of starting material. The DMF was removed under vacuum and the resulting residue was partitioned between DCM (100 ml) and water (100 ml), the organic layer was dried (MgSO$_4$), filtered and concentrated under vacuum. The resulting yellow oil was recrystallised from MeOH to give the title compound (2.3 g, 34% yield) as a white solid. Tr=1.75 min, m/z (ES$^+$) (M+H)$^+$ 339 & 341

4-Bromo-7-hydroxymethyl-2-isopropyl-2H-phthalazin-1-one: 1-Bromo-3-isopropyl-4-oxo-3,4-dihydro-phthalazine-6-carboxylic acid ethyl ester (2.3 g, 6.8 mmol) was suspended in THF (50 ml) and cooled to 0° C. To the suspension was added LiBH$_4$ (5.1 ml of a 2M solution in THF, 10.2 mmol) dropwise, the suspension was allowed to warm to RT and stirred for 24 hours. After this time, LC-MS showed 50% starting material remained. To this was added LiBH$_4$ (1.7 ml of a 2M solution in THF, 3.4 mmol) and the reaction mixture was stirred for a further 3 hours. The reaction was cooled to 0° C., saturated NH$_4$Cl (40 ml) was added and the reaction mixture was then partitioned between water (50 ml) and DCM (150 ml). The organic layer was separated, dried (MgSO$_4$), filtered and concentrated under vacuum. The resulting residue was then purified by flash column chromatography (elution: 50% toluene, 30% EtOAc, 20% DCM) to give the title compound (0.9 g, 43% yield) as a white solid. $\delta_H$ (400 MHz, DMSO), 8.28 (1H, s), 7.96 (1H, d), 7.88 (1 H, d), 5.64 (1H, t), 5.31-5.18 (1H, m), 4.78 (2H, d), 1.35 (6H, d) Tr=1.31 min, m/z (ES$^+$) (M+H)$^+$ 297 & 299

4-Bromo-7-bromomethyl-2-isopropyl-2H-phthalazin-1-one: A solution of 4-bromo-7-hydroxymethyl-2-isopropyl-2H-phthalazin-1-one (0.74 g, 2.5 mmol) in MeCN (5 ml) was added dropwise to a stirred suspension of TMSBr (0.9 g, 6.3 mmol) and LiBr (0.41 g, 5 mmol) in MeCN (15 ml). The reaction mixture was heated to 80° C. for 24 h, after which time the reaction mixture was cooled to RT and the solvent removed under vacuum. The resulting residue was purified by flash column chromatography (elution: 85% heptane, 15% EtOAc) to give the title compound (0.4 g, 44% yield) as a white solid. $\delta_H$ (250 MHz, DMSO), 8.37 (1H, s), 8.03 (1H, d), 7.94 (1 H, d), 5.26-5.09 (1H, m), 4.93 (2H, s), 1.35 (6H, d).

4-Bromo-7-cyclopropylmethoxymethyl-2-isopropyl-2H-phthalazin-1-one: Cyclopropyl-methanol (0.05 ml, 0.67 mmol) was dissolved in THF (1 ml). To this was added NaH (60%, 0.028 g, 0.72 mmol) in a single portion. The mixture was stirred at RT for 5 min then 4-bromo-7-bromomethyl-2-isopropyl-2H-phthalazin-1-one (0.2 g, 0.56 mmol) in THF (1 ml) was added in one portion and the reaction mixture was stirred for 1 hour. Whereupon LC-MS indicated complete consumption of starting material, the solvent was removed under vacuum and the residue was purified by flash column chromatography (elution: 80% heptane, 20% EtOAc) to give the title compound (0.17 g, 87% yield) as a light yellow oil. Tr=1.80 min, m/z (ES$^+$) (M+H)$^+$ 351 & 353

This material was then used in the Buchwald reaction as described in Method ZD to give the corresponding 7-cyclopropylmethoxymethyl-2-isopropyl-4-(5-methyl-1H-pyrazol-3-ylamino)-2H-phthalazin-1-one (E-1).

Example ZH-1

7-Cyclopropylmethoxymethyl-2-isopropyl-4-(5-methyl-1H-pyrazol-3-ylamino)-2H-phthalazin-1-one $\delta_H$ (400 MHz, DMSO), 11.92 (1H, br s), 9.15 (1H, s), 8.42 (1 H, d), 8.24 (1H, s), 7.80 (1H, d), 6.36 (1H, s), 5.29-5.21 (1H, m), 4.68 (2H, s), 2.25 (2H, s), 1.32 (6H, d), 1.12-1.03 (1H, m), 0.53-0.47 (2H, m) Tr=1.80 min, m/z (ES$^+$) (M+H)$^+$ 368.35.

Example ZH-2

2-Isopropyl-4-(5-methyl-1H-pyrazol-3-ylamino)-7-(pyridin-3-ylmethoxymethyl)-2 H-phthalazin-1-one $\delta_H$ (400 MHz, DMSO), 11.92 (1H, s), 9.17 (1H, s), 8.55-8.53 (1H, m), 8.45 (1H, d), 8.31-8.29 (1H, m), 7.89-7.81 (2H, m), 7.52 (1H, d), 7.34-7.30 (1H, m), 6.37 (1H, s), 5.29-5.21 (1H, m), 4.83 (2H, s), 4.68 (2H, s), 2.25 (3H, s), 1.32 (6H, d) Tr=1.55 min, m/z (ES$^+$) (M+H)$^+$ 405.31.

Method ZI:

Example ZI-1

2-Isopropyl-4-(5-methyl-1H-pyrazol-3-ylamino)-7-methylsulfanyl-methyl-2H-phthalazin-1-one 4-Bromo-2-isopropyl-7-methylsulfanylmethyl-2H-phthalazin-1-one: Sodium methanethiolate (0.23 g, 3.33 mmol) was dissolved in THF (1 ml) and added dropwise to a solution of 4-bromo-7-bromomethyl-2-isopropyl-2H-phthalazin-1-one (0.4 g, 1.11 mmol) in THF (10 ml). The mixture was stirred at RT for 3 hours whereupon LC-MS indicated complete consumption of starting material. The reaction mixture was diluted with water (20 ml) and extracted with EtOAc (50 ml). The organic layer was separated, dried (MgSO$_4$), filtered and concentrated under vacuum. The residue was subjected to flash column chromatography (elution: 80% heptane, 20% EtOAc) to give the title compound (0.29 g, 79% yield) as a white solid.

This material was then used in the Buchwald reaction as described in Method ZD to give the corresponding 2-isopropyl-4-(5-methyl-1H-pyrazol-3-ylamino)-7-methylsulfanyl-methyl-2H-phthalazin-1-one (F-1).

Example ZI-1

2-Isopropyl-4-(5-methyl-1H-pyrazol-3-ylamino)-7-methylsulfanyl-methyl-2H-phthalazin-1-one $\delta_H$ (400 MHz, DMSO), 9.15 (1H, s), 8.41 (1 H, d), 8.20 (1H, d), 7.82 (1H, d), 6.36 (1H, s), 5.31-5.19 (1H, m), 3.90 (2H, s), 2.24 (3H, s), 1.95-1.93 (3H, m), 1.32 (6H, d) Tr=1.75 min, m/z (ES$^+$) (M+H)$^+$ 344.29.

Example ZI-2

2-Isopropyl-7-methanesulfonylmethyl-4-(5-methyl-1H-pyrazol-3-yl-amino)-2H-phthalazin-1-one Oxone (0.43 g, 0.7 mmol) was added in one portion to a stirred solution of 2-isopropyl-4-(5-methyl-1H-pyrazol-3-ylamino)-7-methylsulfanylmethyl-2H-phthalazin-1-one (0.06 g, 0.17 mmol) in a 4:1 mixture of dioxane/water (1.2 ml) and the reaction mixture was stirred at RT for 1 hour. The reaction mixture was diluted with water (5 ml) and the solution was extracted with EtOAc (3×75 ml), the organic layers were combined, dried (MgSO$_4$), filtered and concentrated under vacuum to give the title compound (0.013 g, 20% yield) as a white solid. $\delta_H$ (400 MHz, DMSO) 9.23 (1H, s), 8.48 (1H, d), 8.38 (1H, d), 7.89 (1H, dd), 6.36 (1H, s), 5.33-5.20 (1H, m), 4.77 (2H, s), 2.96 (3H, s), 2.25 (3H, s), 1.33 (6H, d) Tr=1.58 min, m/z (ES$^+$) (M+H)$^+$ 376.24.

Method ZJ:

Example ZJ-1

N-[3-Isopropyl-1-(5-methyl-1H-pyrazol-3-ylamino)-4-oxo-3,4-dihydro-phthalazin-6-yl] -2-methoxy-N-methyl-acetamide N-(1-Bromo-3-isopropyl-4-oxo-3,4-dihydro-phthalazin-6-yl)-2-methoxy-N-methyl-acetamide: 4-Bromo-2-isopropyl-7-methylamino-2H-phthalazin-1-one (0.5 g, 1.69 mmol) was dissolved in DMF (5 ml). To this was added NaH (60%, 0.19 g, 5.1 mmol) as a suspension in DMF (2 ml). The mixture was stirred at RT for 30 min then methoxyacetyl chloride (0.27 g, 2.5 mmol) was added dropwise and the reaction mixture was stirred at RT for 24 hours. After this time, water (10 ml) was added cautiously, the mixture was extracted with EtOAc (3×10 ml), the organic layers were combined, dried (MgSO$_4$), filtered and concentrated under vacuum. Flash column chromatography (elution: 50% hexane, 50% EtOAc) gave the title compound (0.47 g, 76% yield) as a white solid.

This material was then used in the Buchwald reaction as described in Method ZC to give the corresponding 2-isopropyl-7-methylamino-4-(5-methyl-1H-pyrazol-3-ylamino)-2H-phthalazin-1-one.

2-Isopropyl-7-methylamino-4-(5-methyl-1H-pyrazol-3-ylamino)-2H-phthalazin-1-one (0.4 g, 1.3 mmol) was dissolved in DMF (5 ml). To this was added NaH (60%, 0.1 g, 2.6 mmol) as a suspension in DMF (2 ml). The mixture was stirred at RT for 5 min then methoxyacetyl chloride (0.28 g, 2.6 mmol) was added dropwise and the reaction mixture was stirred at RT for 2 hours. After this time, water (10 ml) was added cautiously, the mixture was extracted with EtOAc (3×10 ml), the organic layers were combined, dried (MgSO$_4$), filtered and concentrated under vacuum. The residue was dissolved in THF (5 ml) and heated to 60° C. in the presence of solid sodium hydroxide (100 mg) for 2 hours. After this time the mixture was concentrated under vacuum and subjected to flash column chromatography (elution: 95% EtOAc, 5% MeOH) to give N-[3-isopropyl-1-(5-methyl-1H-pyrazol-3-ylamino)-4-oxo-3,4-dihydro-phthalazin-6-yl]-2-methoxy-N-methyl-acetamide (0.06 g, 12% yield) as a white solid.

Example ZJ-1

N-[3-Isopropyl-1-(5-methyl-1H-pyrazol-3-ylamino)-4-oxo-3,4-dihydro-phthalazin-6-yl]-2-methoxy-N-methyl-acetamide $\delta_H$ (400 MHz, DMSO), 9.25 (1H, s), 8.48 (1H, d), 8.17 (1H, d), 7.89 (1H, dd), 6.35 (1H, s), 5.32-5.17 (1H, m), 4.05-3.92 (2H, m), 3.28 (3H, s), 3.22 (3H, s), 2.25 (3H, s), 1.32 (6H, d) Tr=1.56 min, m/z (ES$^+$) (M+H)$^+$ 385.29.

Example ZJ-2

N-[3-(3,5-Difluoro-benzyl)-1-(5-methyl-1H-pyrazol-3-ylamino)-4-oxo-3,4-dihydro-phthalazin-6-yl]-2-methoxy-N-methyl-acetamide $\delta_H$ (400 MHz, DMSO), 9.32 (1H, br s), 8.49 (1H, d), 8.20 (1H, d), 7.92 (1H, dd), 7.22-7.02 (3H, m), 6.06 (1H, br s), 5.26 (2H, s), 4.01 (2H, br s), 3.29 (3H, s), 3.22 (3H, s), 2.17 (1H, s) Tr=1.80 min, m/z (ES$^+$) (M+H)$^+$ 468.95.

Example ZJ-3

N-[3-Isopropyl-1-(5-methyl-1H-pyrazol-3-ylamino)-4-oxo-3,4-dihydro-phthalazin-6-yl]-N-methyl-2-phenoxy-acetamide $\delta_H$ (400 MHz, DMSO), 9.41 (1H, s), 8.50 (1H, d), 8.26 (1H, s), 7.99 (1H, d), 7.31-7.13 (4H, m), 7.10-7.05 (1H, m), 6.91 (1H, t), 6.87-6.78 (2H, m), 6.08 (1H, s), 5.28 (2H, s), 4.78 (2H, br s), 2.19 (3H, s) Tr=2.07 min, m/z (ES$^+$) (M+H)$^+$ 530.97.

Method ZK:

Example ZK-1

4-[3-Isopropyl-1-(5-methyl-1H-pyrazol-3-ylamino)-4-oxo-3,4-dihydro-phthalazin-6-ylamino]-butyric acid 4-Bromo-2-isopropyl-7-(2-oxo-pyrrolidin-1-yl)-2H-phthalazin-1-one: To a solution of 7-amino-2-isopropyl-4-bromo-2H-phthalazin-1-one (0.5 g, 1.8 mmol) in DMF (8 ml), was added TEA (0.28 ml, 1.98 mmol). After 5 min, 4-chlorobutyryl chloride (0.22 ml, 2.0 mmol) was added and the solution was stirred at RT for 2 hours. After this time LC-MS indicated the complete consumption of starting material and the mixture was diluted with DCM (30 ml) and washed with HCl (1M, 20 ml). The organic layer was separated, dried (MgSO$_4$) and concentrated under vacuum. The residue was subjected to flash column chromatography (elution: 60% heptane, 40% EtOAc) to give N-(1-bromo-3-isopropyl-4-oxo-3,4-dihydro-phthalazin-6-yl)-4-chloro-butyramide (0.46 g, 67% yield) as a white solid.

This material was dissolved in DMF (5 ml). To this was added NaH (60%, 0.05 g, 1.3 mmol) as a suspension in DMF (2 ml). The mixture was stirred at RT for 2 hours. After this time, water (10 ml) was added cautiously, the mixture was extracted with EtOAc (3×10 ml) and the organic layers were combined, dried (MgSO$_4$), filtered and concentrated under vacuum. The residue was subjected to flash column chromatography (elution: 60% heptane, 40% EtOAc) to give the title compound (0.15 g, 36% yield) as a pale yellow solid.

This material was then used in the Buchwald reaction as described in Method ZD. to give the corresponding 4-[3-Isopropyl-1-(5-methyl-1H-pyrazol-3-ylamino)-4-oxo-3,4-dihydro-phthalazin-6-ylamino]-butyric acid (H-1)

Example ZK-1

4-[3-Isopropyl-1-(5-methyl-1H-pyrazol-3-ylamino)-4-oxo-3,4-dihydro-phthalazin-6-ylamino]-butyric acid $\delta_H$ (400 MHz, DMSO) 8.10 (1H, s), 7.08 (1H, d), 7.02-6.83 (2H, m), 6.16 (1H, s), 5.27-5.01 (1H, m), 3.02 (2H, d), 2.08 (3H, s), 1.99 (2H, t), 1.78-1.54 (2H, m), 1.19 (6H, d) Tr=1.60 min, m/z (ES$^+$) (M+H)$^+$ 385.43.

The features disclosed in the foregoing description, or the following claims expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A method of treating rheumatoid arthritis comprising administering to a patient in need thereof a therapeutically effective amount of a compound according to formula I

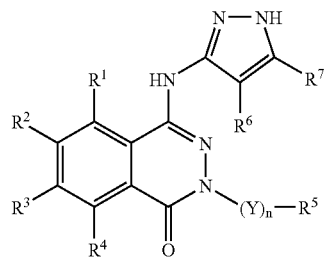

wherein $R^1$, $R^2$ and $R^4$ independently represent $R^8$—X—, $C_{3-7}$cycloalkyl-$T^1$-, heterocyclyl-$T^2$-, -hydrogen, halogen, nitro, cyano, —OH, —NH$_2$, —NH—C(O)H, —C(O)OH, —C(O)NH$_2$, —S(O)$_2$NH$_2$, —NHC(O)NH$_2$, —C(O)NH—O—C$_{1-6}$alkyl, —C(O)N(C$_{1-6}$alkyl)—O—C$_{1-6}$alkyl, —NHC(O)NH—O—C$_{1-6}$alkyl, —NHC(O)N(C$_{1-6}$alkyl)—O—C$_{1-6}$ alkyl, —S(O)$_2$NH—O—C$_{1-6}$alkyl, —S(O)$_2$N(C$_{1-6}$alkyl)—O—C$_{1-6}$alkyl, or C$_{1-6}$alkyl optionally substituted one or three times by halogen, hydroxy or alkoxy;

$R^3$ is $R^8$—X—, $R^9$—X$^1$—, $R^8$—X$^1$(CH$_2$)$_m$—, $R^9$—X$^1$(CH$_2$)$_m$—, $C_{3-7}$cycloalkyl-$T^1$-, heterocyclyl-$T^2$-, hydrogen, halogen, nitro, cyano, —OH, —NH$_2$, —NH—C(O)H, —C(O)OH, —C(O)NH$_2$, —S(O)$_2$NH$_2$, —NHC(O)NH$_2$, —C(O)NH—O—C$_{1-6}$alkyl, —C(O)N(C$_{1-6}$alkyl)—O—C$_{1-6}$alkyl, —NHC(O)NH—O—C$_{1-6}$alkyl, —NHC(O)N(C$_{1-6}$alkyl)—O—C$_{1-6}$alkyl, —S(O)$_2$NH—O—C$_{1-6}$alkyl, —S(O)$_2$N(C$_{1-6}$alkyl)—O—C$_{1-6}$ alkyl, or C$_{1-6}$alkyl optionally substituted one or three times by halogen, hydroxy or alkoxy;

$R^8$ is $C_{3-7}$cycloalkyl-$T^1$-, heterocyclyl-$T^2$-, aryl-$T^3$-, heteroaryl-$T^4$-, or C$_{1-6}$alkyl optionally substituted one to five times by halogen;

$R^9$ is $C_{1-6}$ alkyl wherein said alkyl is substituted one to three times hydroxy, alkoxy, amino, C$_{1-6}$alkylamino, C$_{1-6}$dialkylamino, C$_{1-6}$alkylsulfanyl, C$_{1-6}$alkylsulfinyl, C$_{1-6}$alkylsulfonyl, C$_{1-6}$alkylsulfamoyl, C$_{1-6}$dialkylsulfamoyl, C$_{1-6}$alkylsulfonylamino or heterocyclylsulfonyl;

X is —C(O)NH—, —C(O)N(C$_{1-6}$alkyl)-, —N(C$_{1-6}$alkyl)C(O)—, —NHC(O)—, —NHC(O)NH—, —NHC(O)N(C$_{1-6}$alkyl)-, —OC(O)N(C$_{1-6}$alkyl)-, —NHS(O)$_2$—, —S(O)$_2$NH—, —S(O)$_2$N(C$_{1-6}$alkyl)-, —S(O)$_2$—, —S(O)—, —C(O)O—, —OC(O)—, —C(O)—, —NH—, —N(C$_{1-6}$alkyl)-, —O— or —S—;

$X^1$ is —S(O)$_2$—, —S(O)—, —OC(O)—, —C(O)—, NH—, —N(C$_{1-6}$alkyl)-, —O— or —S—;

$T^1$, $T^2$, $T^3$ and $T^4$ independently represent a single bond or alkylene optionally substituted one or two times by hydroxy;

$R^5$ is hydrogen, C$_{1-6}$alkyl being optionally substituted one or several times by halogen or alkoxy, heteroaryl, or phenyl, which is optionally substituted one or two times by halogen, —NO$_2$, —OH, —C(O)OH, —C(O)NH-aryl, —C(O)NH$_2$, —C(O)NH—C$_{1-6}$alkyl, —C(O)N(C$_{1-6}$alkyl)$_2$, —C(O)-heterocyclyl, —NH$_2$, —NHC(O)-aryl, —NHC(O)—C$_{3-7}$cycloalkyl, —NHC(O)—C$_{1-6}$alkyl, —N(C$_{1-6}$alkyl)C(O)—C$_{1-6}$alkyl, —NHC(O)O—C$_{1-6}$alkyl, —N(C$_{1-6}$alkyl)C(O)O—C$_{1-6}$alkyl, —NHC(O)—C$_{1-6}$alkoxyalkyl, —NH—S(O)$_2$-aryl, —NH—S(O)$_2$—C$_{1-6}$alkyl, —C(O)NH—S(O)$_2$-aryl, —C(O)NH—S(O)$_2$—C$_{1-6}$alkyl, —S(O)$_2$-alkyl, —NH-aryl, —O-aryl, —S(O)-aryl, aryl, heterocyclyl, C$_{3-7}$cycloalkyl, C$_{1-6}$alkyl, C$_{1-6}$alkoxy or C$_{1-6}$alkylsulfanyl, said alkyl, alkoxy and alkylsulfanyl groups being optionally substituted one or three times by halogen; naphthyl optionally independently substituted with one to three halogens, phenyl independently substituted with three halogens; 1,3-dihydro-isobenzofuranyl, benzo[1,3]dioxol-5-yl, C$_{3-7}$cycloalkyl or C$_{1-6}$alkenyl;

Y is alkylene, alkylene—C(O)— or alkylene—CH(OH)—;

m is 1 to 5;

n is 0 or 1;

$R^6$ is hydrogen, C$_{1-6}$alkyl, cyano or halogen; and $R^7$ is hydrogen, C$_{1-6}$alkyl or C$_{3-7}$cycloalkyl;

or a pharmaceutically acceptable salt thereof.

* * * * *